United States Patent
Paik et al.

(10) Patent No.: US 9,315,869 B2
(45) Date of Patent: Apr. 19, 2016

(54) MARKER FOR PREDICTING GASTRIC CANCER PROGNOSIS AND METHOD FOR PREDICTING GASTRIC CANCER PROGNOSIS USING THE SAME

(75) Inventors: Soon Myung Paik, Pittsburgh, PA (US); Sung Kim, Gyeonggi-do (KR); Won Ki Kang, Seoul (KR); Jee Yun Lee, Seoul (KR); Jae Moon Bae, Seoul (KR); Tae Sung Sohn, Seoul (KR); Jae Hyung Noh, Seoul (KR); Min Gew Choi, Seoul (KR); Young Suk Park, Seoul (KR); Joon Oh Park, Gyeonggi-do (KR); Se Hoon Park, Seoul (KR); Ho Yeong Lim, Gyeonggi-do (KR); Sin Ho Jung, Chapel Hill, NC (US)

(73) Assignee: Samsung Life Public Welfare Foundation, Seoul (KR)

( * ) Notice: Subject to any disclaimer, the term of this patent is extended or adjusted under 35 U.S.C. 154(b) by 106 days.

(21) Appl. No.: 13/994,072

(22) PCT Filed: Dec. 13, 2011

(86) PCT No.: PCT/KR2011/009603
§ 371 (c)(1),
(2), (4) Date: Aug. 26, 2013

(87) PCT Pub. No.: WO2012/081898
PCT Pub. Date: Jun. 21, 2012

(65) Prior Publication Data
US 2013/0337449 A1 Dec. 19, 2013

(30) Foreign Application Priority Data
Dec. 13, 2010 (KR) .................. 10-2010-0127197

(51) Int. Cl.
C12Q 1/68 (2006.01)
G01N 33/53 (2006.01)
G01N 33/574 (2006.01)
G06F 19/00 (2011.01)

(52) U.S. Cl.
CPC ........ C12Q 1/6886 (2013.01); G01N 33/57446 (2013.01); C12Q 2600/118 (2013.01); C12Q 2600/158 (2013.01); G01N 2800/52 (2013.01); G06F 19/34 (2013.01)

(58) Field of Classification Search
None
See application file for complete search history.

(56) References Cited
U.S. PATENT DOCUMENTS
2007/0092529 A1 4/2007 Be et al.

FOREIGN PATENT DOCUMENTS

| KR | 1020070084488 A | 8/2007 |
| KR | 1020070088979 A | 8/2007 |
| KR | 1020080073745 A | 8/2008 |
| WO | 2006/060265 A2 | 6/2006 |
| WO | 2007/059094 A2 | 5/2007 |

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Bair et al., "Semi-Supervised Methods to Predict Patient Survival from Gene Expression Data," PLoS Biology 2(4):0511-0522, 2004.
Cho et al., "Expression and prognostic significance of human growth and transformation-dependent protein in gastric carcinoma and gastric adenoma," Human Pathology 40:975-981, 2009.
Chu et al., "Matrix metalloproteinase-9 is associated with disease-free survival and overall survival in patients with gastric cancer," Int. J. Cancer 129:887-895, 2011.
Kim et al., "An observational study suggesting clinical benefit for adjuvant postoperative chemoradiation in a population of over 500 cases after gastric resection with D2 nodal dissection for adenocarcinoma of the stomach," Int. J. Radiation Oncology Biol. Phys. 63(5):1279-1285, 2005.
Simon et al., "Analysis of Gene Expression Data using BRB-Array Tools," Cancer Informatics 2:11-17, 2007.
Sohn et al., "Gradient lasso for Cox proportional hazards model," Bioinformatics 25(14):1775-1781, 2009.
Takeno et al., "Gene Expression Profile Prospectively Predicts Peritoneal Relapse After Curative Surgery of Gastric Cancer," Ann. Surg. Oncol. 17:1033-1042, 2010.
Xu et al., "Gene expression profile towards the prediction of patient survival of gastric cancer," Biomedicine & Pharmacotherapy 64:133-139, 2010.

* cited by examiner

Primary Examiner — James Martinell
(74) Attorney, Agent, or Firm — Seed IP Law Group PLLC

(57) ABSTRACT

The present invention relates to a marker for predicting a gastric cancer prognosis, a composition and a kit for predicting gastric cancer prognosis comprising an agent for measuring the expression level thereof, and a method for predicting gastric cancer prognosis using the marker. According to the present invention, gastric cancer prognosis may be predicted promptly and accurately, and an appropriate treatment plan can be determined based on the predicted prognosis, which has an advantage of contributing to significant reduction of death caused by gastric cancer. Particularly, according to the present invention, the survival rate can be remarkably increased by using the treatment method for a stage III gastric cancer patient to a patient who has been predicted to have a negative prognosis among stage Ib/II gastric cancer patients.

4 Claims, 47 Drawing Sheets

MARKER FOR PREDICTING GASTRIC CANCER PROGNOSIS AND METHOD FOR PREDICTING GASTRIC CANCER PROGNOSIS USING THE SAME

BACKGROUND OF THE INVENTION

1. Field of the Invention

The present invention relates to a marker for predicting gastric cancer prognosis, a composition and a kit for predicting gastric cancer prognosis comprising an agent for measuring the expression level thereof, and a method for predicting gastric cancer prognosis using the marker.

2. Description of the Related Art

In 2005, a total of 65,479 people, which is 26.7% of all deaths, died of cancer. Cancer which causes the most deaths is lung cancer, of which 28.4 patients per 100,000 populations died (21.1%), the next is gastric cancer of 22.6 patients (16.8%), liver cancer of 22.5 patients (16.7%), colorectal cancer of 12.5 patients (9.3%) in order. Gastric cancer is known as the factor that causes the second most deaths worldwide among the deaths caused by cancer.

The symptoms of gastric cancer show various aspects, ranging from no symptoms to severe pain. In addition, the symptoms of gastric cancer appear common digestive symptoms without any specific characteristics. In general, in the early stage of gastric cancer, most cases have no symptom, even if any, little as a little indigestion or upper abdominal discomfort, which causes most people to overlook and therefore can increase the mortality of gastric cancer.

Most of examination methods for gastric cancer up to the present have been physical ones. First is stomach X-ray, which includes double contrast method, compression x-ray, mucosagraphy, and the next is gastroscopy which increases the diagnostic yield by finding a very small lesion that does not appear in the X-ray inspection through inspection of the stomach with the naked eyes and allowing the stomach biopsy in a suspicious place. However, this method has the disadvantages of hygienic problem and patients suffering from the pain during the inspection. Therefore, in recent years, the researches for diagnosing gastric cancer by measuring the expression level of the marker genes that are specifically expressed in the stomach have been carried out, but the researches on genetic markers for predicting the prognosis of gastric cancer patients are relatively less.

The survival rate of patients with gastric cancer depends on the pathologic stage at the time of diagnosis. According to the data of Samsung Medical Center, the 5-year survival rate of patients with gastric cancer is as follows (Kim S et al., Int J Radiat Oncol Biol Phys 2005; 63:1279-85).

stage II: 76.2%, stage IIIA: 57.6%,
stage IIIB: 39.6%, stage IV: 26.3%

The results show that early detection of gastric cancer can contribute significantly to the increase of survival rate. However, since the gastric cancer which has been diagnosed with the same stage shows the difference in the prognosis according to the patient, the accurate prediction of the prognosis of gastric cancer as well as the early detection of gastric cancer are the most important factors for effective treatment of gastric cancer.

On the other hand, the diagnosis of gastric cancer, the doctor is set up to conduct the necessary inspections and to patients that are deemed the most appropriate treatment plan. There are methods for treatment of cancer such as surgery, endoscopic therapy, chemotherapy, and radiation therapy. The method for treatment is typically determined by considering the treatment for gastric cancer, gastric cancer of the size, location, and scope of, the patient's general health status, and many other factors.

In the case of the treatment of IB/II stage gastric cancer only with the surgery, it is known that approximately 30% of patients relapse within 5 years. In this case, since it is unable to predict in which patients the gastric cancer is recurrent, the different treatments are applied according to the doctor. Therefore, if the prognosis of gastric cancer patients can be accurately predicted, appropriate treatment methods, such as surgery or chemotherapy, can be determined based on the prognosis, which can contribute greatly to the survival of gastric cancer patients, and therefore the technique that can accurately predict the prognosis of gastric cancer patients is required.

Conventionally, anatomical observations (the degree of cancer cell invasion and the number of metastasized lymph nodes) have been used in order to predict the prognosis of gastric cancer patients, but there have been the possible intervention of physician's subjective judgment and the limitation of accurate prediction of the prognosis.

Under such a background, the present inventors, as the result of the researches for the method which can increase the survival rate of gastric cancer patients by predicting the gastric cancer prognosis accurately and determining the appropriate treatment direction according to the predicted prognosis, identified that the gastric cancer prognosis can be accurately predicted by identifying a marker for predicting the gastric cancer prognosis and measuring the expression level of the marker, to complete the present invention.

SUMMARY OF THE INVENTION

The objective of the present invention is to provide the marker for predicting gastric cancer prognosis comprising the one or more genes selected from the group consisting of C20orf103, COL10A1, MATN3, FMO2, FOXS1, COL8A1, THBS4, CDC25B, CDK1, CLIP4, LTB4R2, NOX4, TFDP1, ADRA2C, CSK, FZD9, GALR1, GRM6, INSP, LPHN1, LYN, MRGPRX3, ALAS1, CASP8, CLYBL, CST2, HSPC159, MADCAM1, MAF, REG3A, RNF152, UCHL1, ZBED5, GPNMB, H1ST1H2AJ, RPL9, DPP6, ARL10, ISLR2, GPBAR1, CPS1, BCL11B and PCDHGA8 genes.

Another objective of the present invention is to provide a composition for predicting gastric cancer prognosis comprising an agent for measuring the expression level of mRNA or protein of the marker for predicting gastric cancer prognosis.

Another objective of the present invention is to provide a kit for predicting gastric cancer prognosis comprising an agent for measuring the expression level of mRNA or protein of the marker for predicting gastric cancer prognosis.

Another objective of the present invention is to provide a method for predicting gastric cancer prognosis comprising a) obtaining the expression level or expression pattern of mRNA or protein of the marker for predicting gastric cancer prognosis in a sample collected from a gastric cancer patient; and b) comparing the expression level or expression pattern obtained from step a) with the expression level or expression pattern of mRNA or protein of the corresponding genes in a gastric cancer patient with known prognosis.

Another objective of the present invention is to provide a method for predicting gastric cancer prognosis comprising a) measuring the expression level of mRNA or protein of the marker for predicting gastric cancer prognosis in a sample collected from a gastric cancer patient to obtain the quantified expression value; b) applying the expression value obtained in step a) to the prognosis prediction model to obtain the gastric cancer prognostic score; and c) comparing the gastric cancer prognostic score obtained in step b) with the reference value to determine prognosis of patient.

The p-values of FIGS. 2a to 15b are the result values of classifying the expression level of the genes by high expression or low expression and level of gene expression and performing the log-rank tests.

Figure 16:
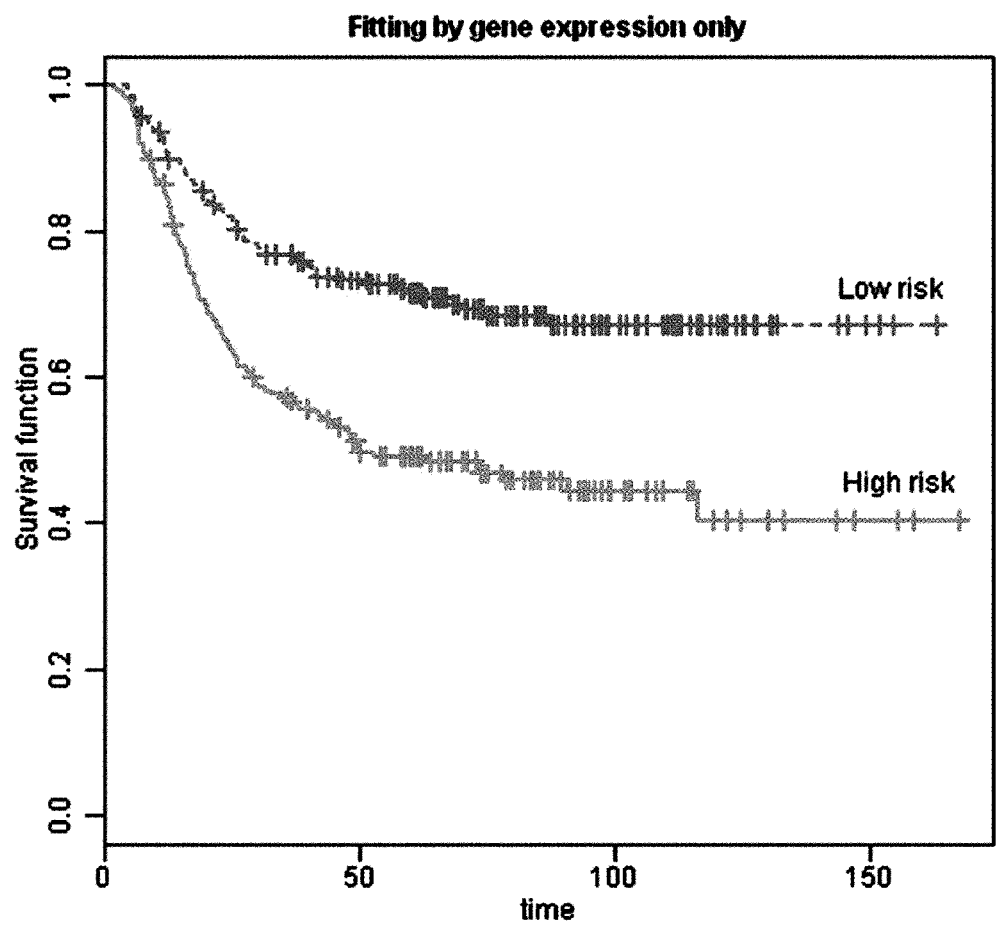

FIG. 16 is the Kaplan-Meier plot showing the disease-free survival rate of positive prognosis group (low risk) or negative prognosis group (high risk) classified according to the prognosis prediction model using the genes listed in Table 5.

Figure 17:
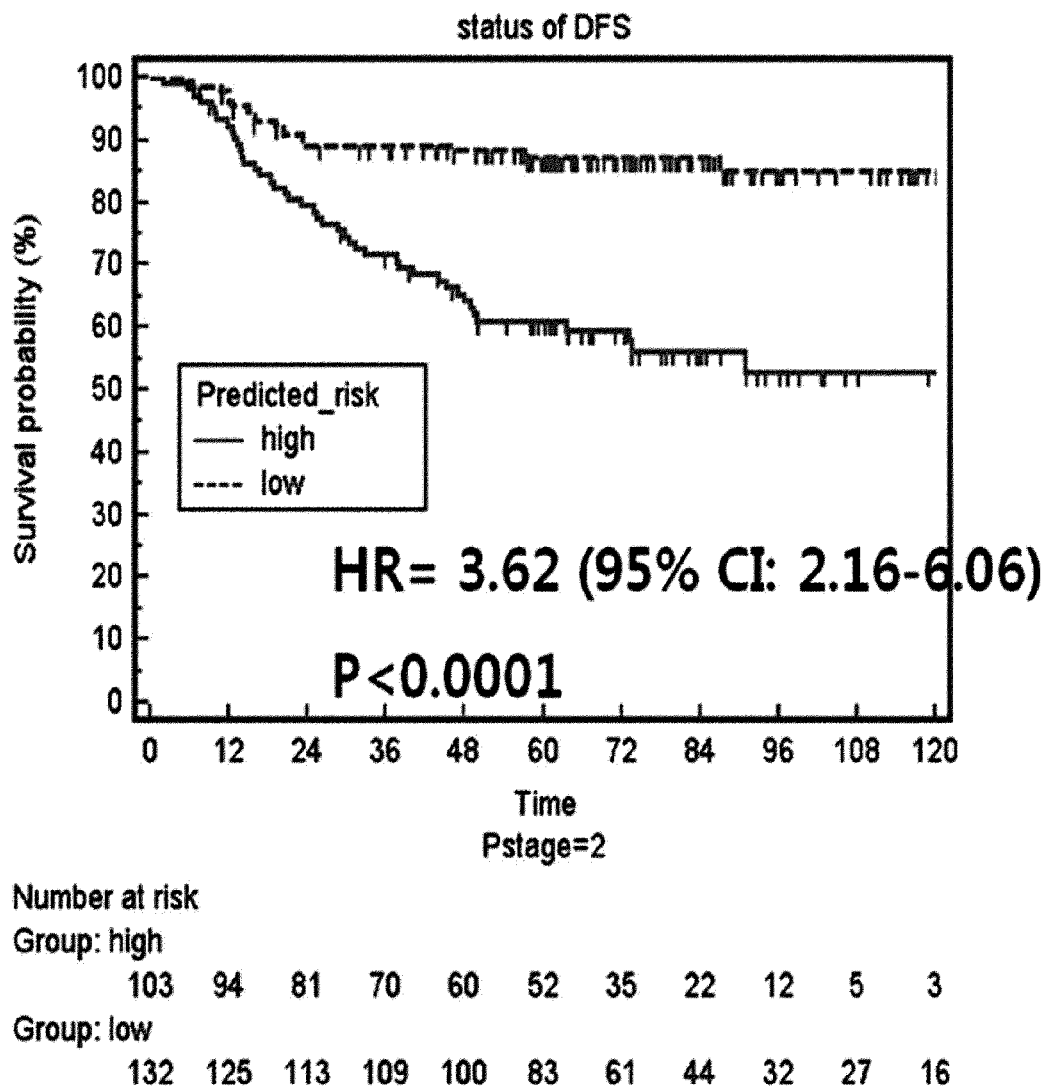

FIG. 17 is the Kaplan-Meier plot showing the disease-free survival rate of stage Ib/II gastric cancer patients classified to positive prognosis group or negative prognosis group according to the prognosis prediction model using the genes listed in Table 5.

Figure 18:
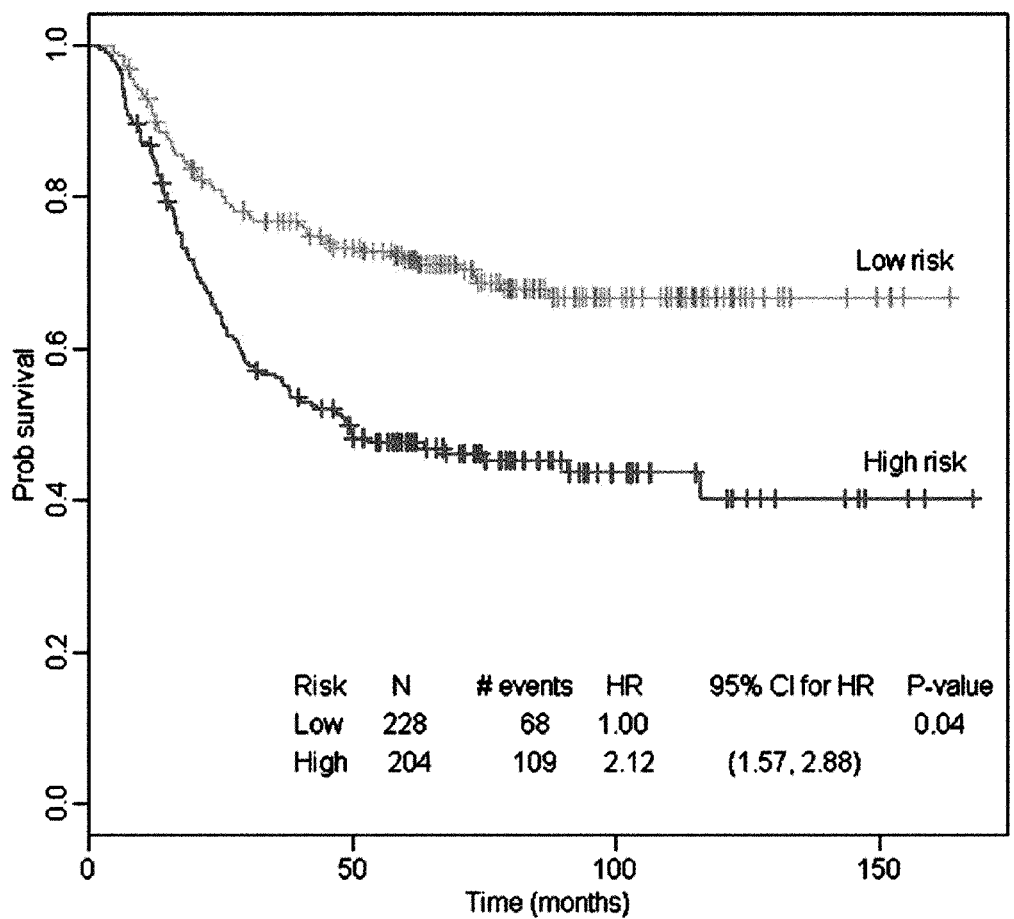

FIG. 18 is the Kaplan-Meier plot showing the disease-free survival rate of positive prognosis group (low risk) or negative prognosis group (high risk) classified according to the prognosis prediction model using the genes listed in Table 7. HR in FIG. 18 is the cumulative risk function ratio and the p-value was calculated using 100 permutations.

Figure 19:
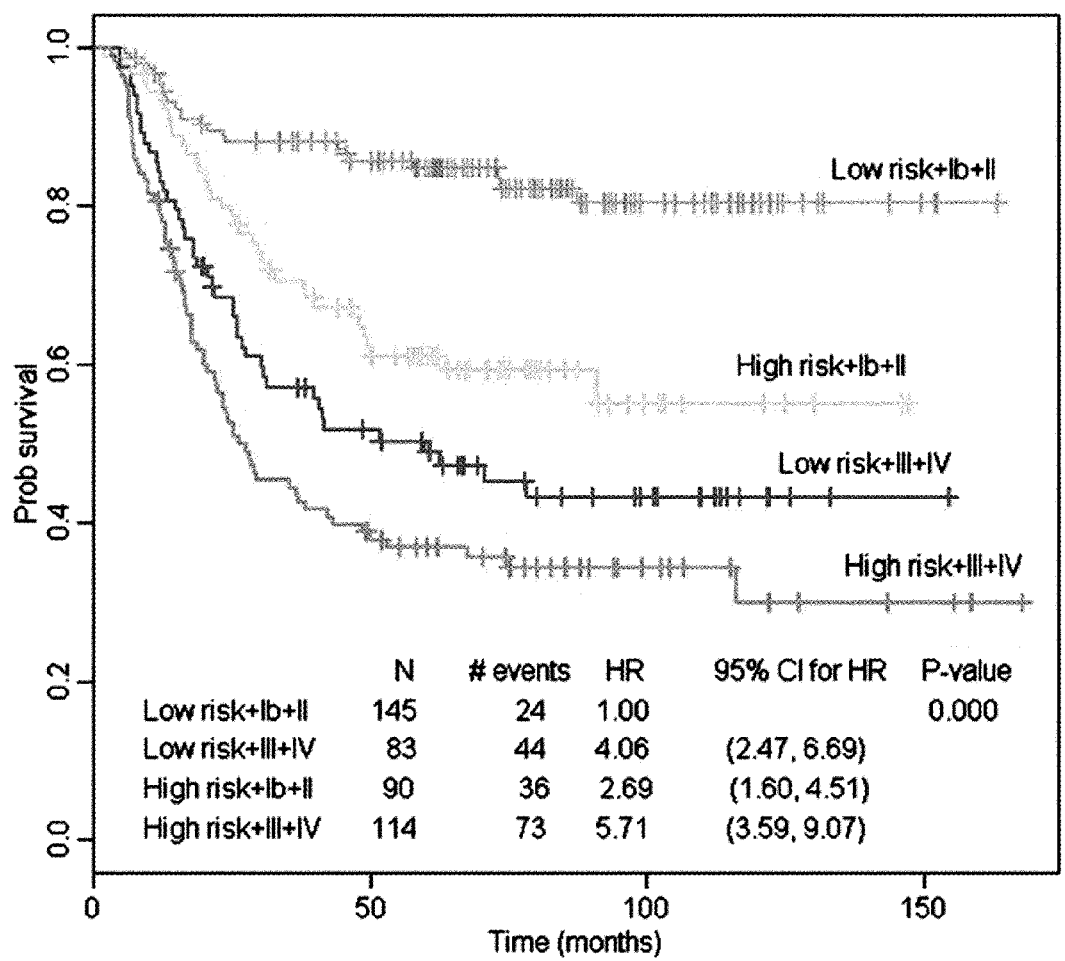

FIG. 19 is the Kaplan-Meier plot for patient groups by classifying the patient (high vs low), who were classified according to the prognosis prediction model using the genes listed in Table 7, according to pathologic stage (IB+II vs III+IV). The p-value was calculated by two-sided log-rank test.

Figure 20A:
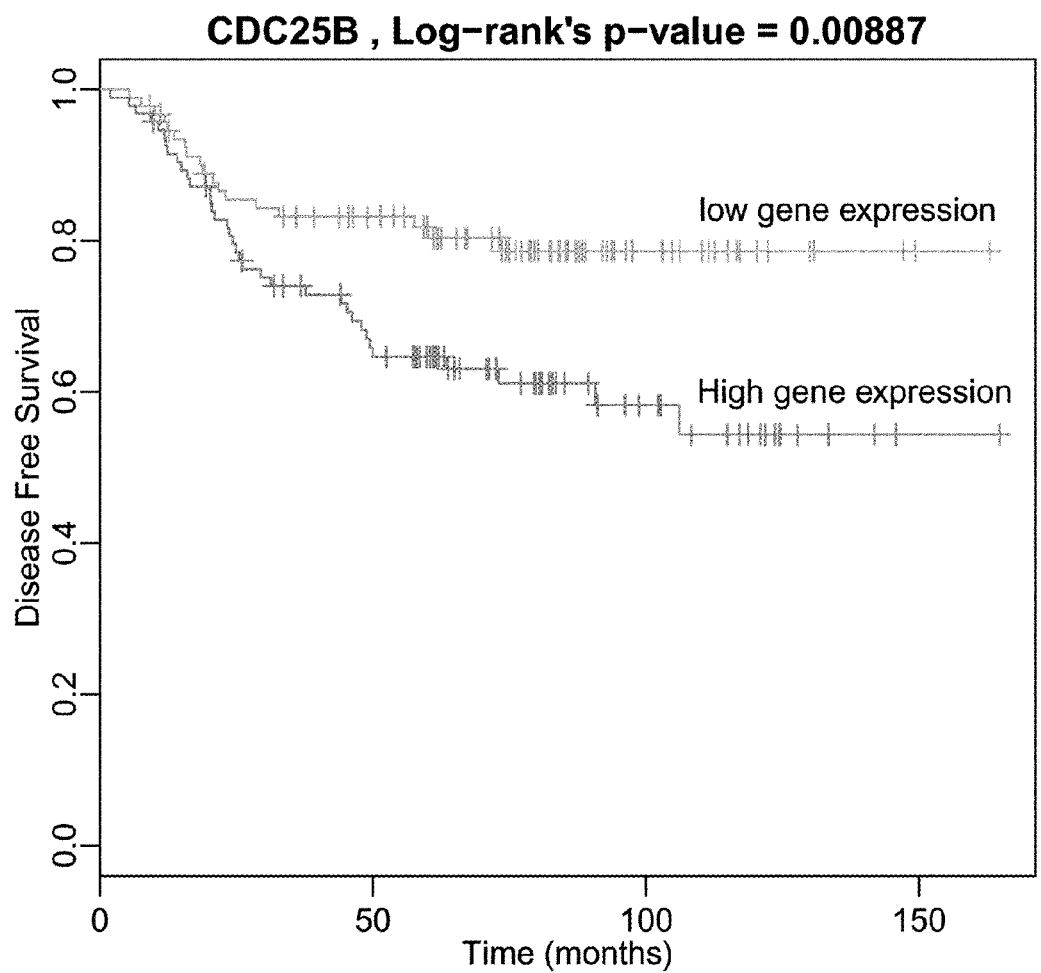
Figure 20B:
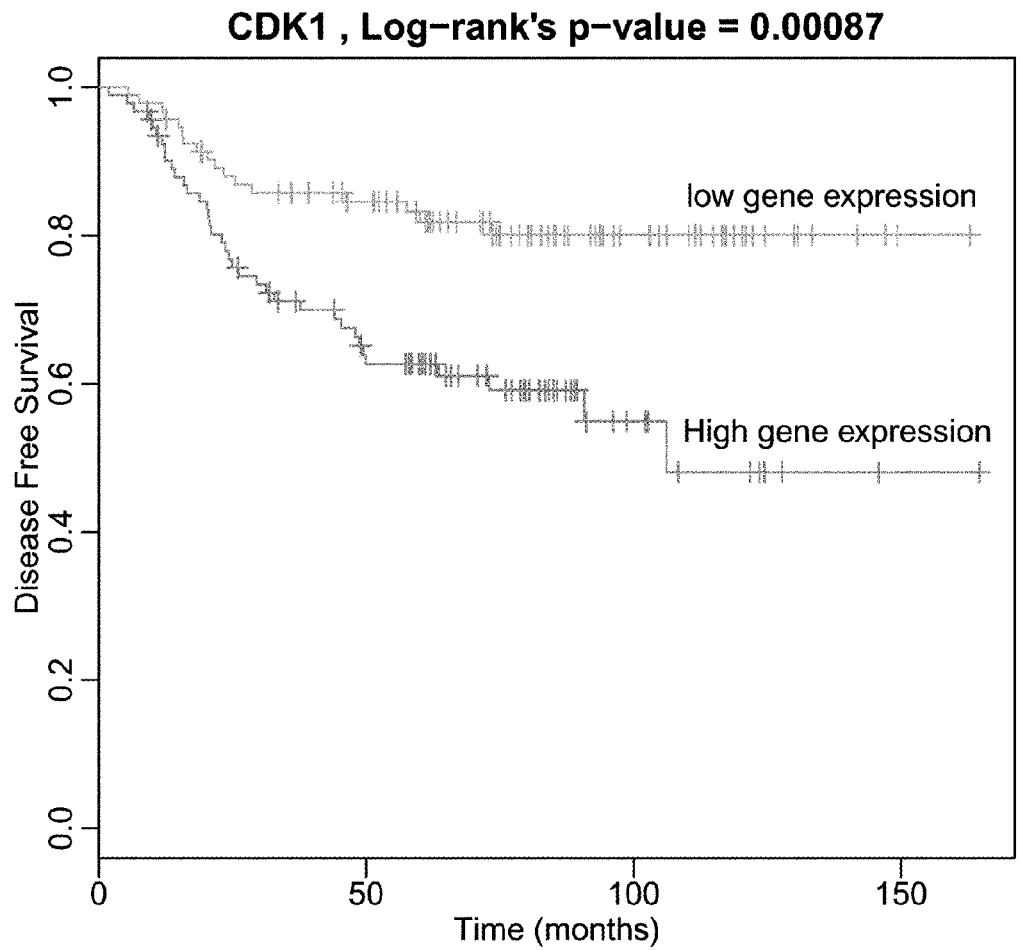

FIGS. 20a and 20b represent the Kaplan-Meier plot according to the expression level of CDC25B, CDK1 genes.

Figure 21A:
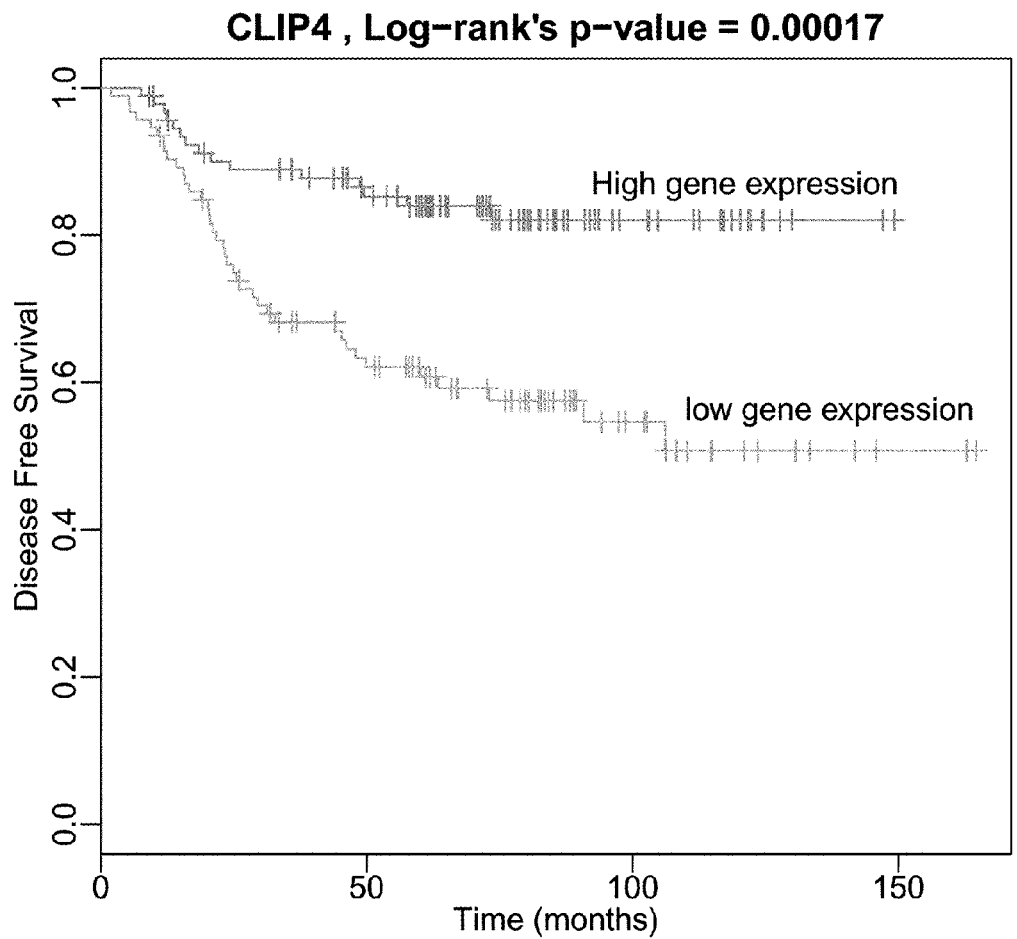
Figure 21B:
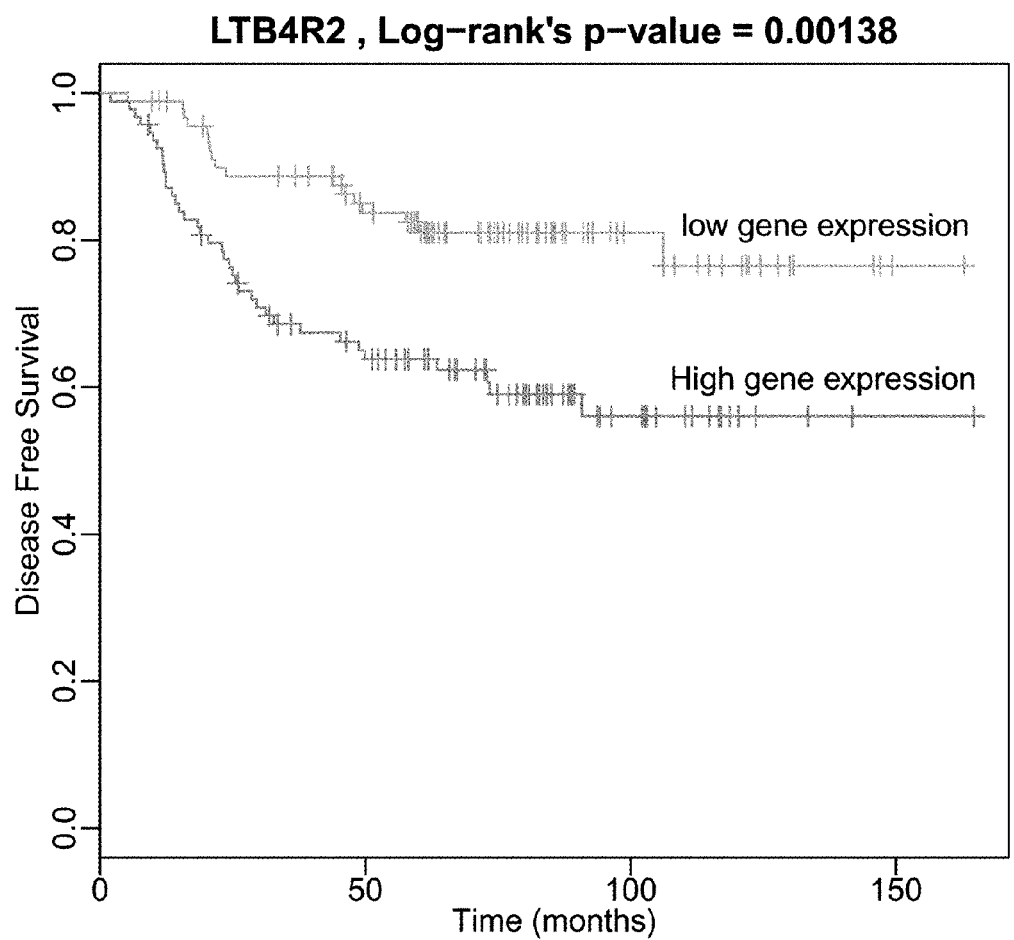

FIGS. 21a and 21b represent the Kaplan-Meier plot according to the expression level of CLIP4, LTB4R2 genes.

Figure 22A:
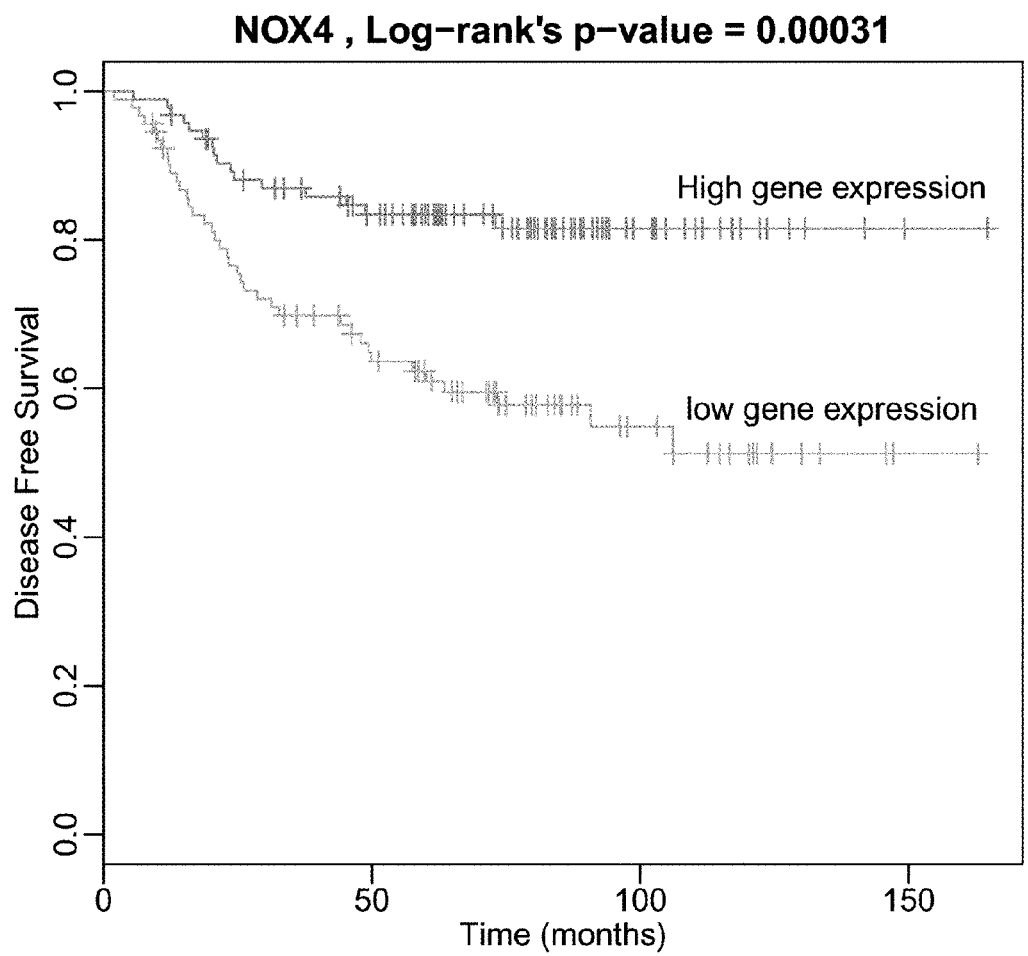
Figure 22B:
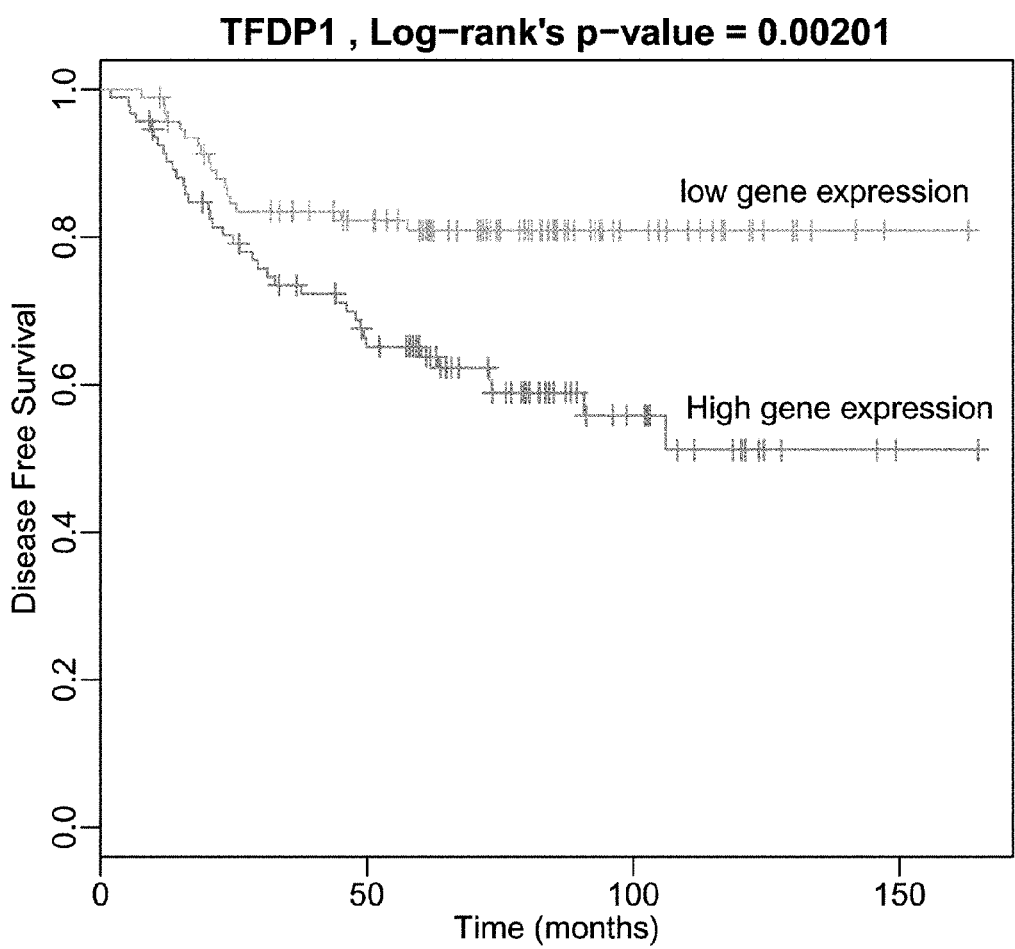

FIGS. 22a and 22b represent the Kaplan-Meier plot according to the expression level of NOX4, TFDP1 genes.

Figure 23A:
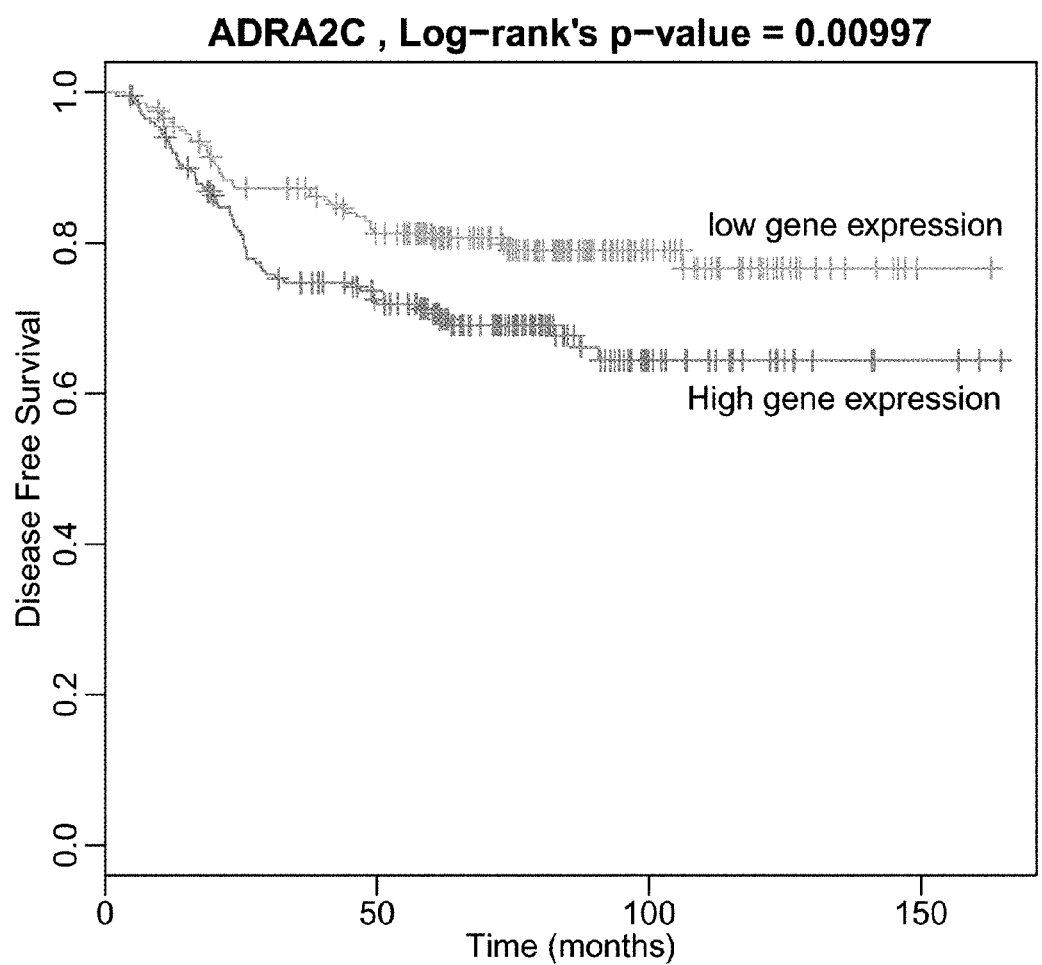
Figure 23B:
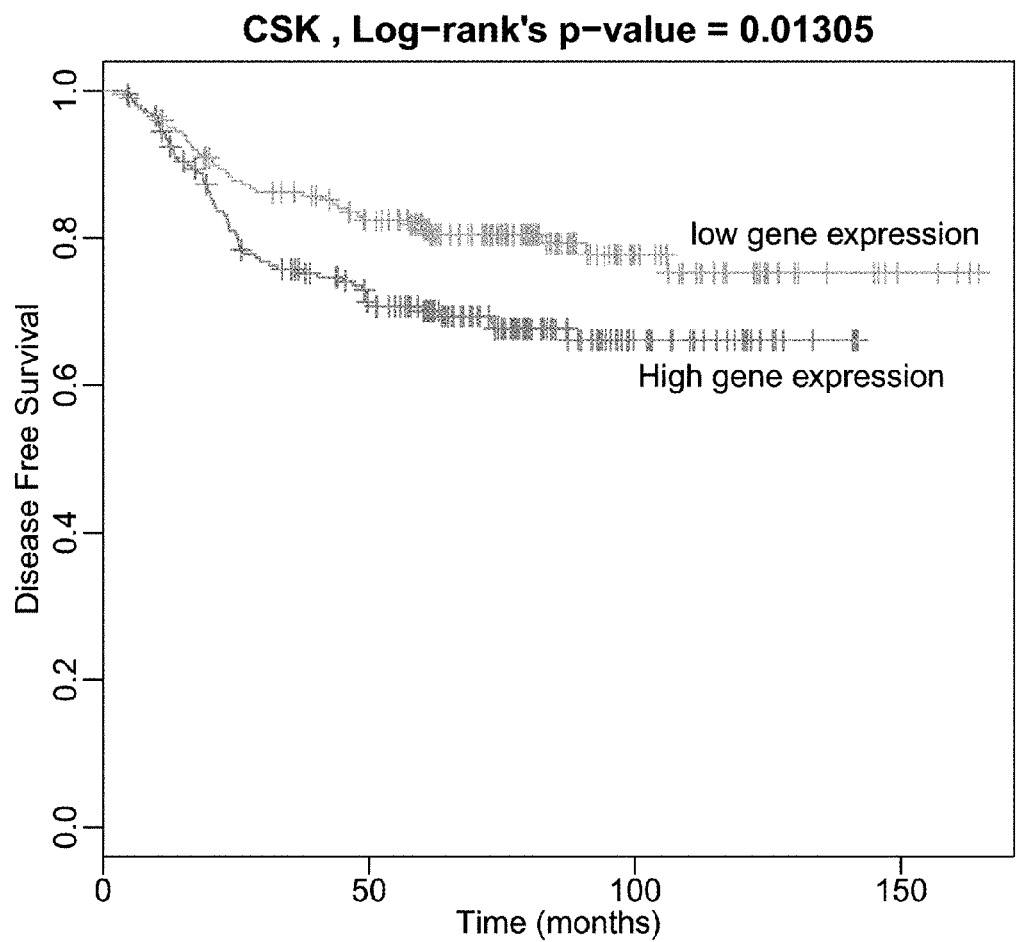

FIGS. 23a and 23b represent the Kaplan-Me ier plot according to the expression level of ADRA2C, CSK genes.

Figure 24A:
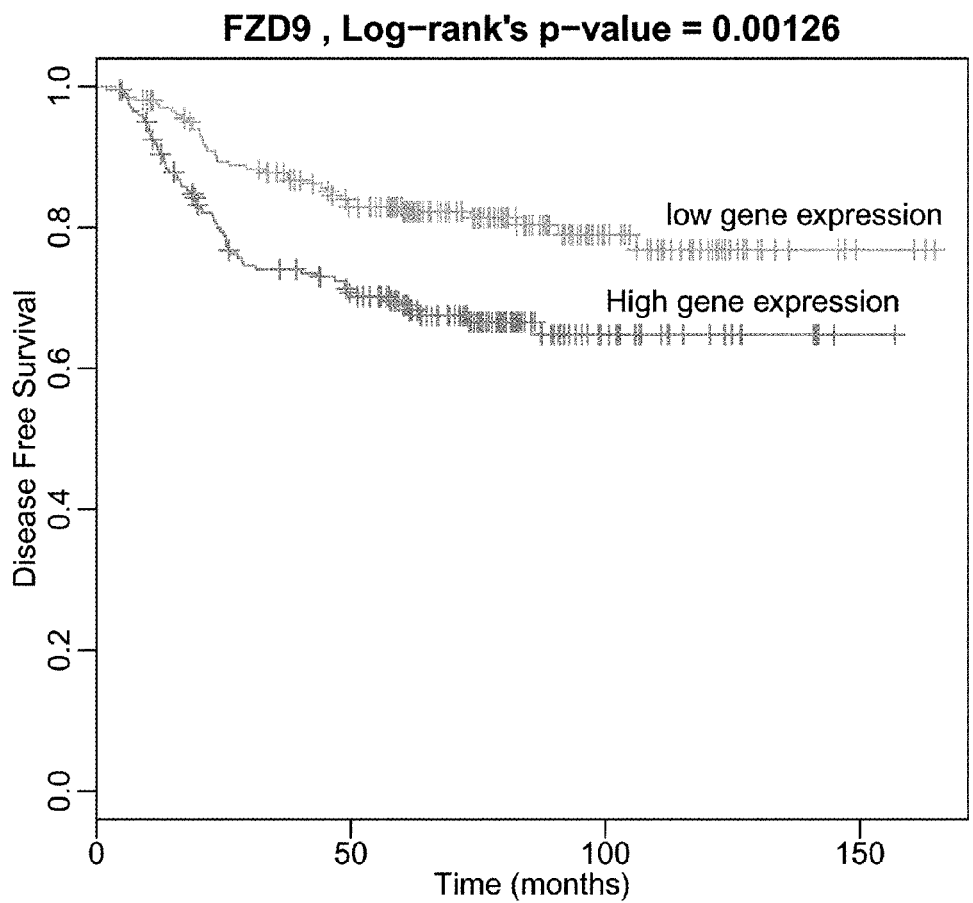
Figure 24B:
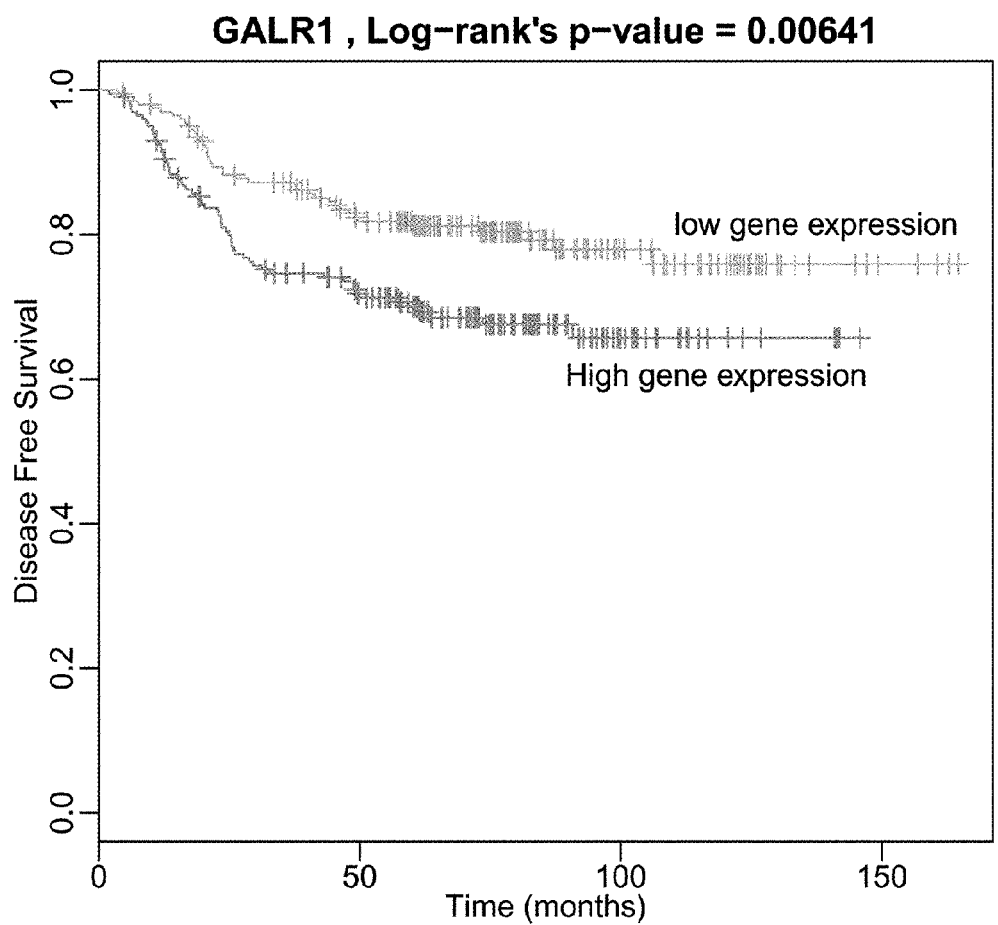

FIGS. 24a and 24b represent the Kaplan-Meier plot according to the expression level of FZD9, GALR1 genes.

Figure 25A:
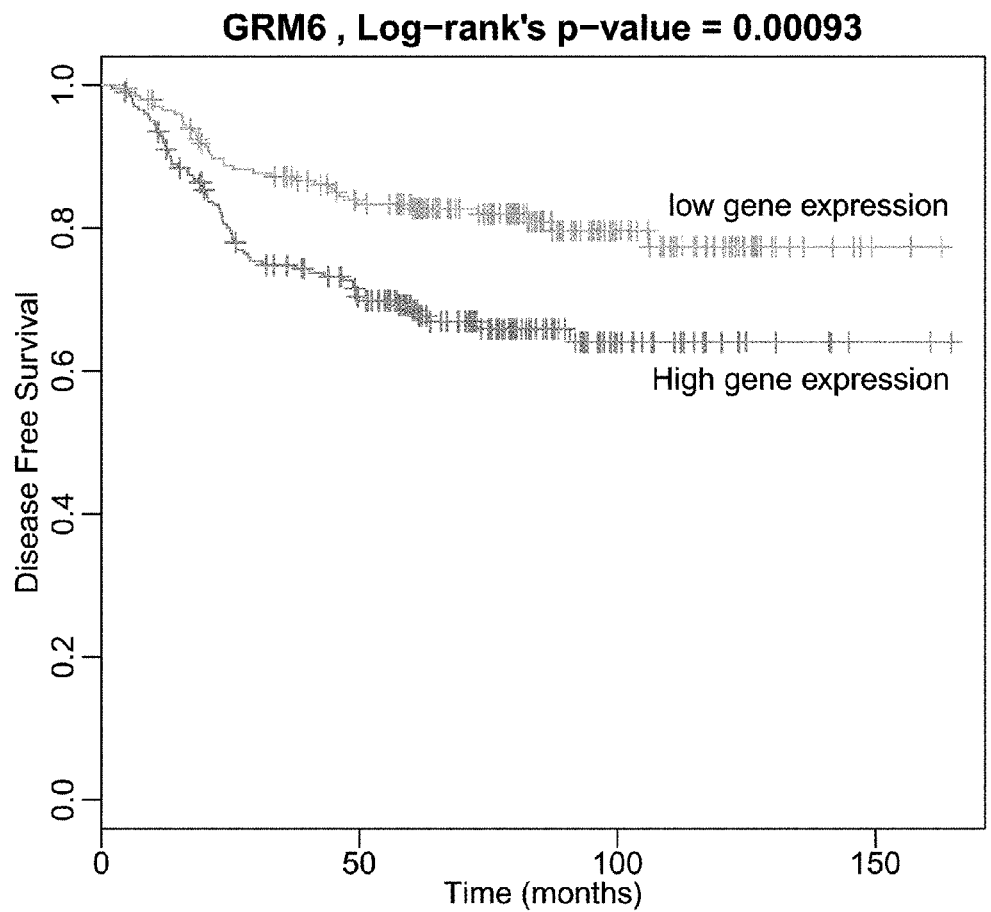
Figure 25B:
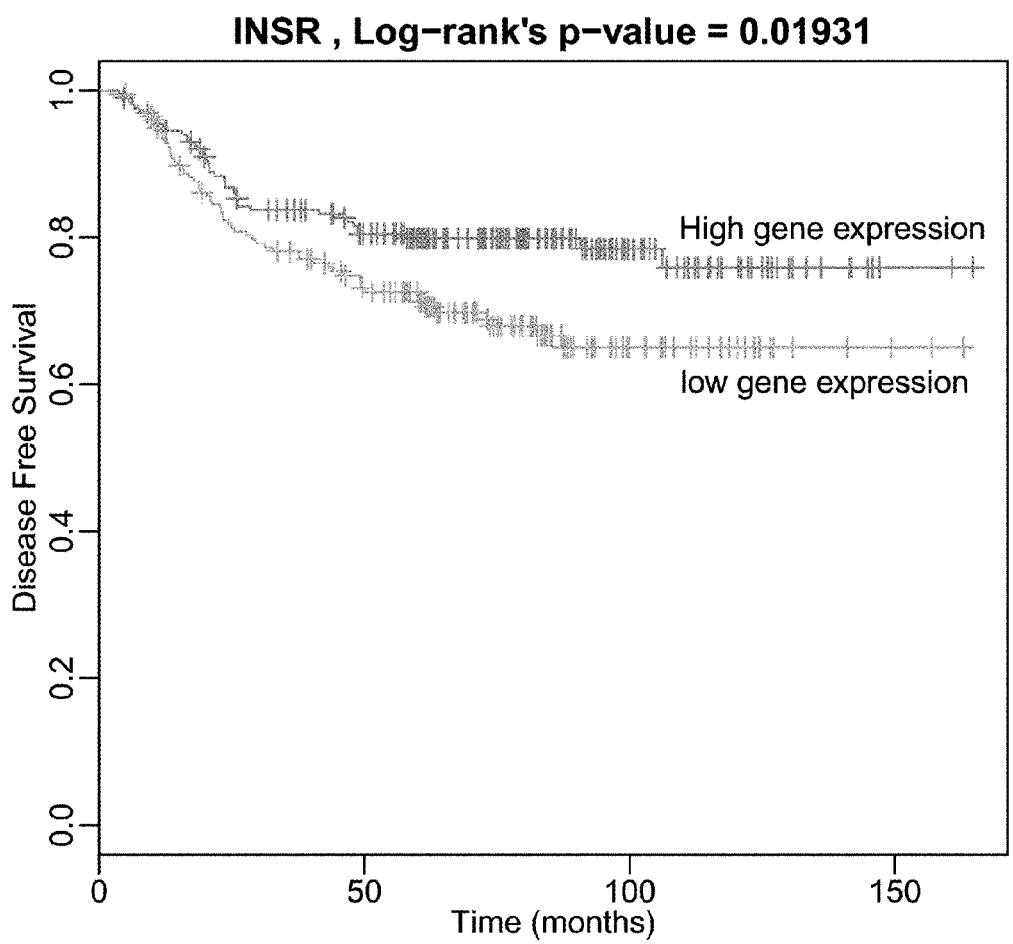

FIGS. 25a and 25b represent the Kaplan-Meier plot according to the expression level of GRM6, INSR genes.

Figure 26A:
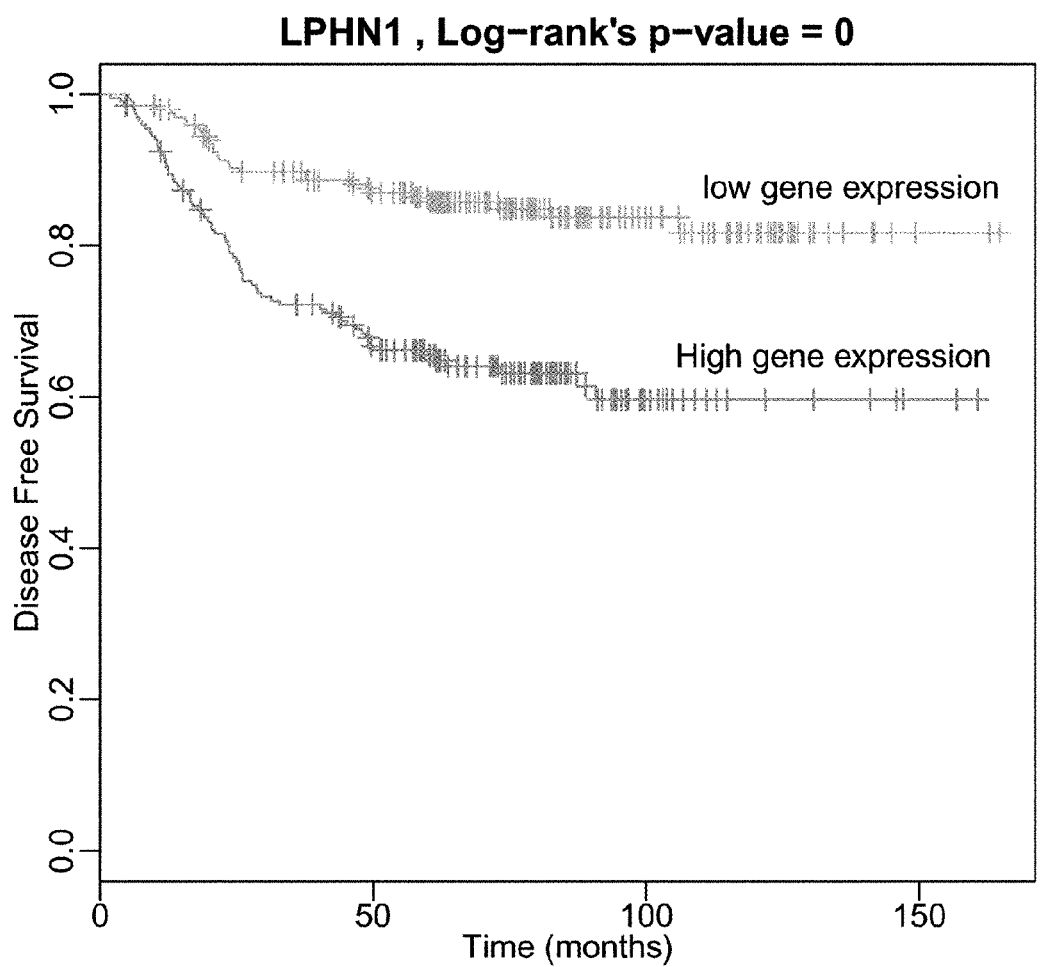
Figure 26B:
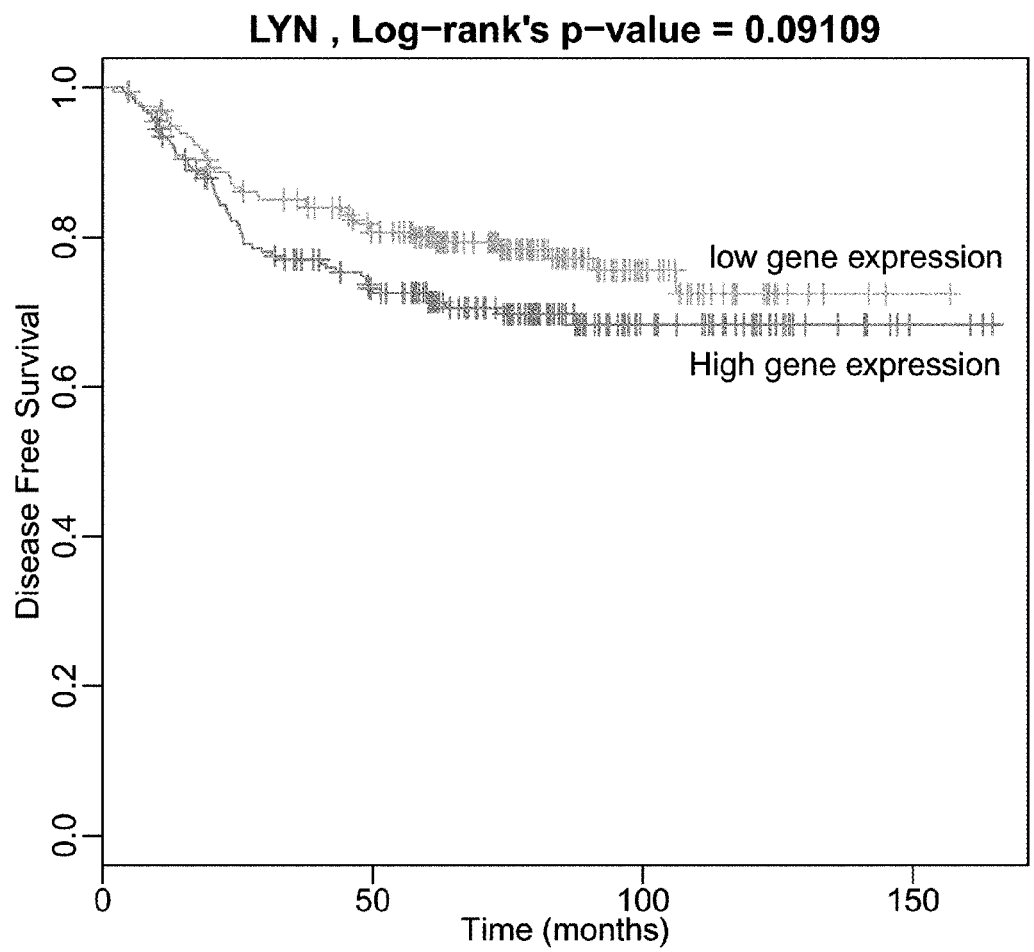

FIGS. 26a and 26b represent the Kaplan-Meier plot according to the expression level of LPHN1, LYN genes.

Figure 27:
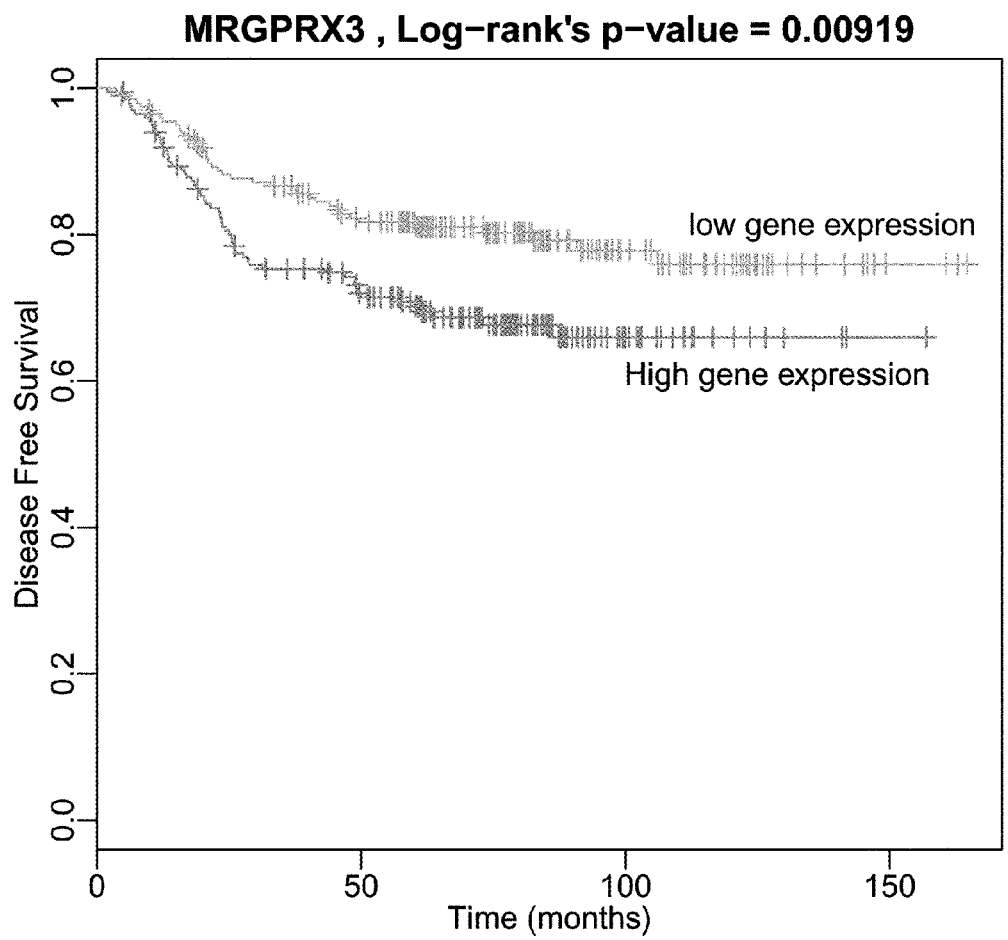

FIG. 27 represents the Kaplan-Meier plot according to the expression level of MRGPRX3 gene.

The p-values of FIGS. 20a to 27 are the result values of classifying the expression level of the genes by high expression or low expression and level of gene expression and performing the log-rank tests.

Figure 28:
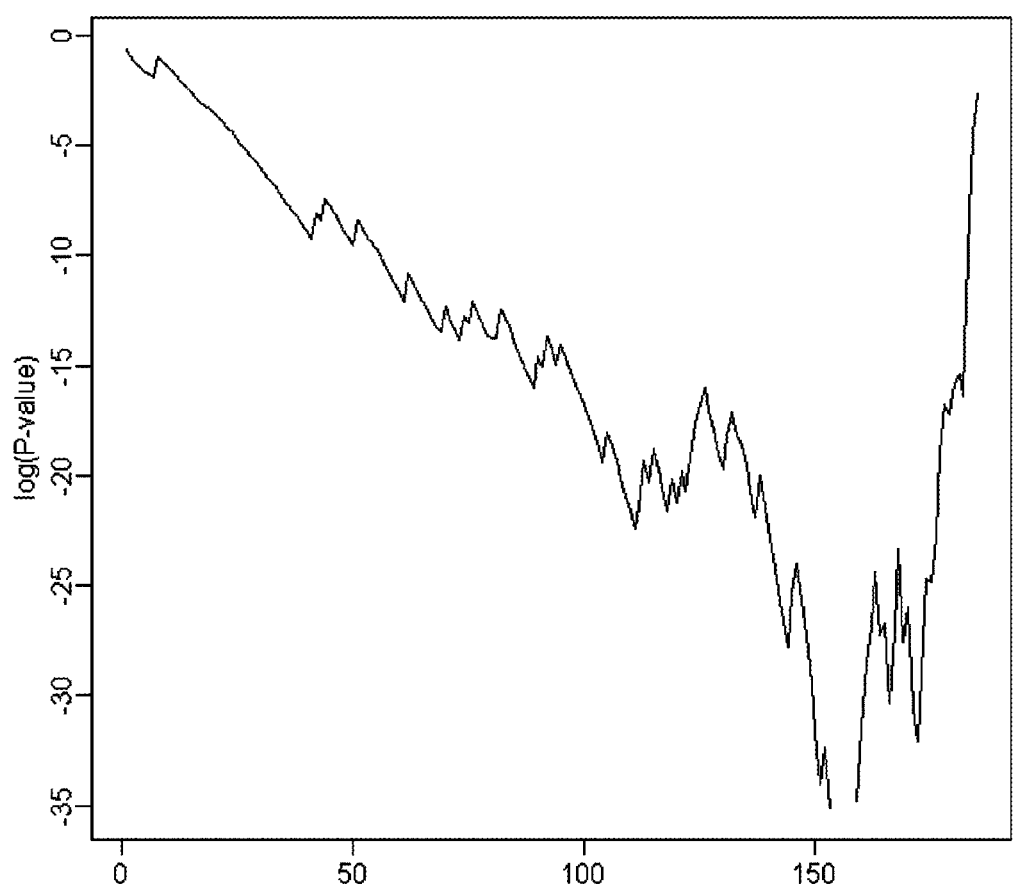

FIG. 28 represents the cut-off analysis of GCPS of the genes listed in Table 10. The best discrimination was the case of classifying the patients as high-risk group 75% and low-risk group 25°.

Figure 29:
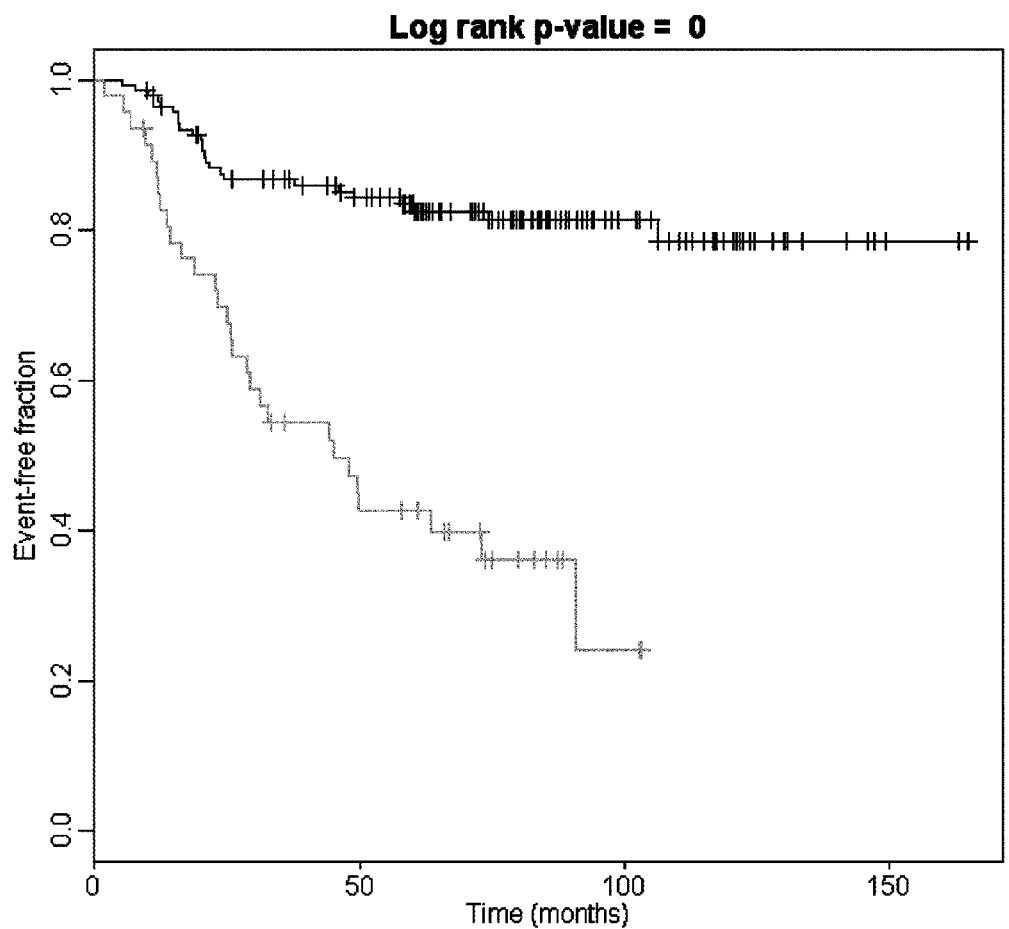

FIG. 29 represents the disease-free survival rate of stage II gastric cancer patients in the discovery set based on the optimized cut-off of GCPS of the genes listed in Table 10.

Figure 30:
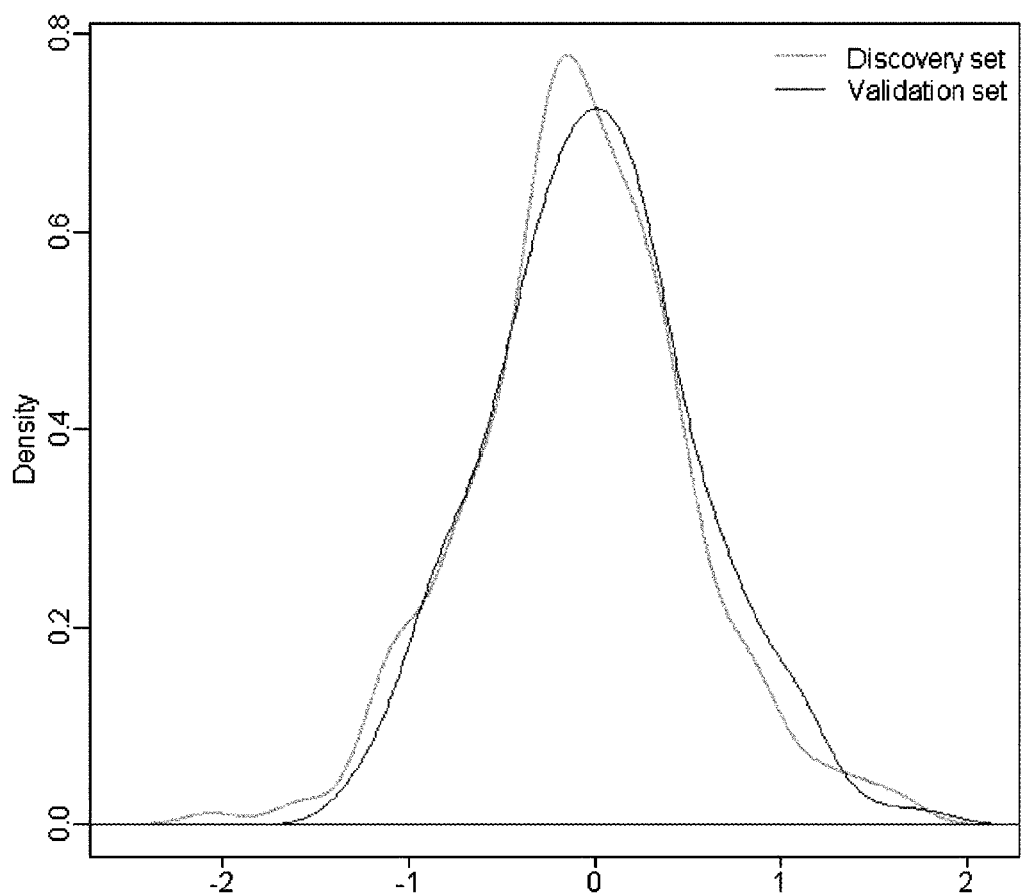

FIG. 30 represents the distributions of GCPS of the genes listed in Table 10 in discovery set versus validation set, and shows that the distribution of GCPS in discovery set coincides with that in validation set. This represents the analytical robustness of this assay.

Figure 31:
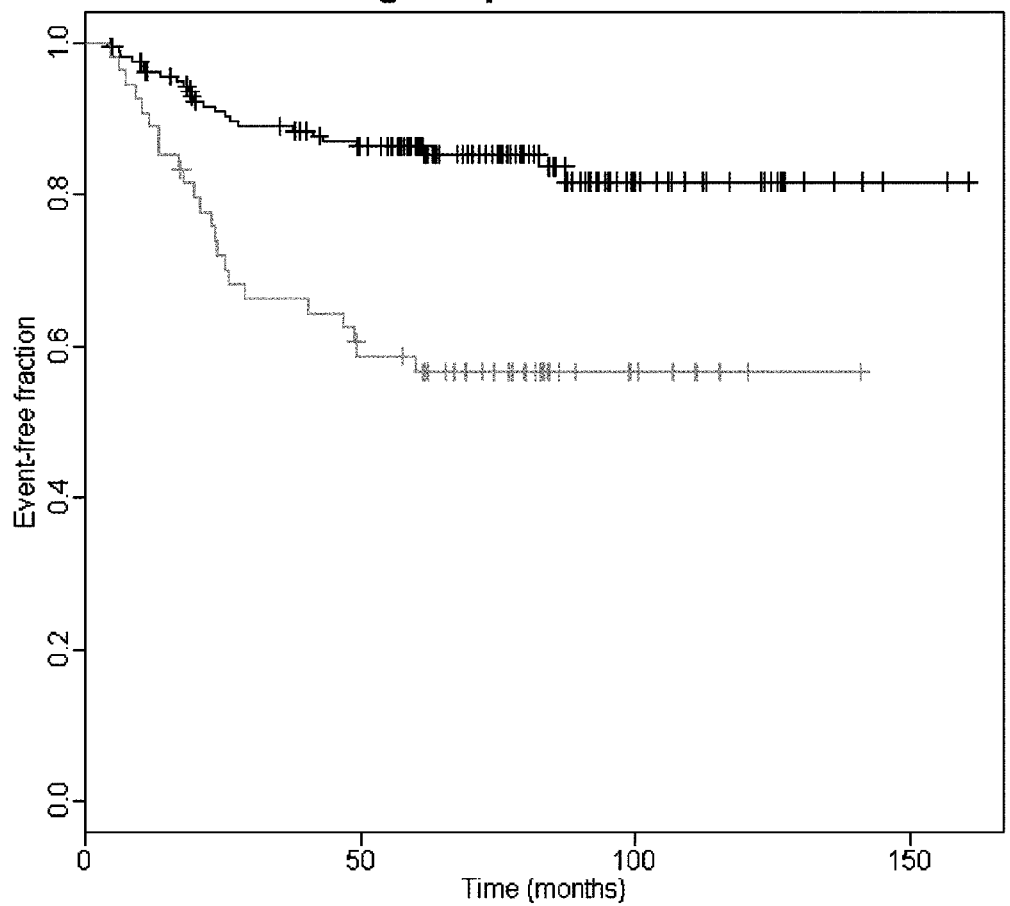

FIG. 31 represents the disease-free survival rate of the validation cohort according to the predefined algorithm GCPS and the cut-off (red=high risk).

Figure 32:
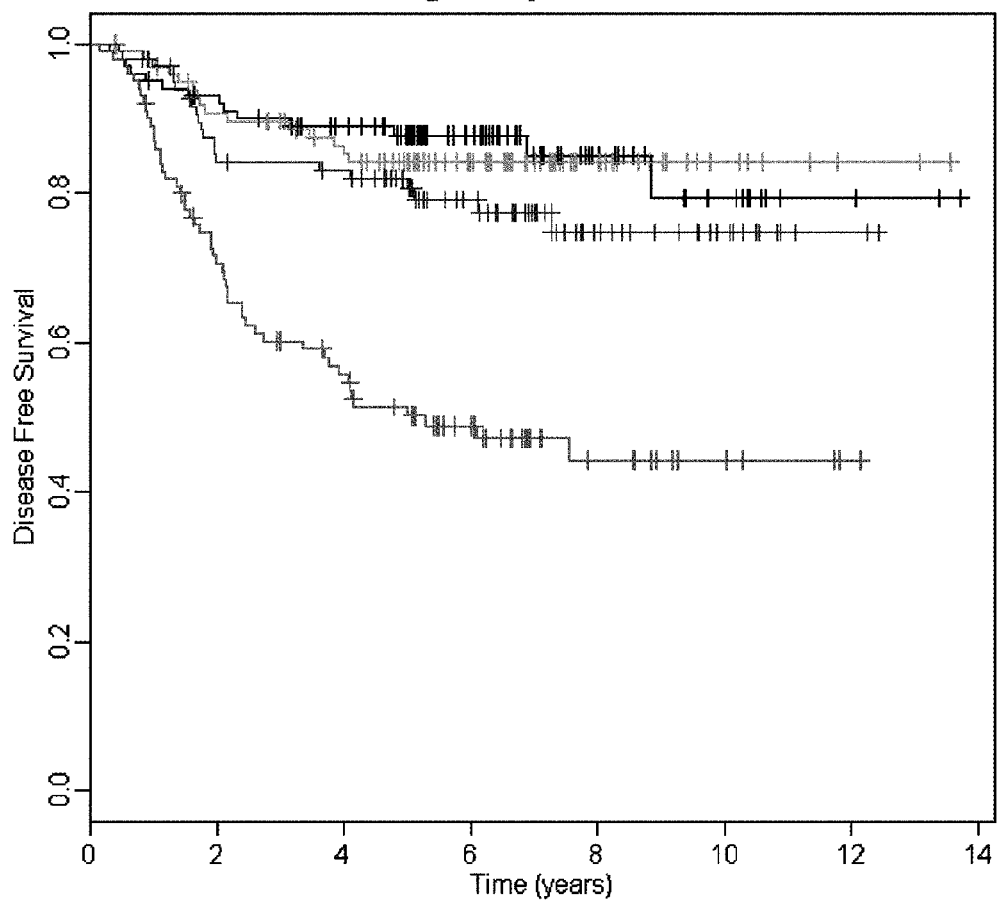

FIG. 32 represents the disease-free survival rate of state II gastric cancer patients which received surgery based on GCPS of the genes listed in Table 11 and radiation therapy. The blue color represents a high risk defined by GCPS.

Figure 33:
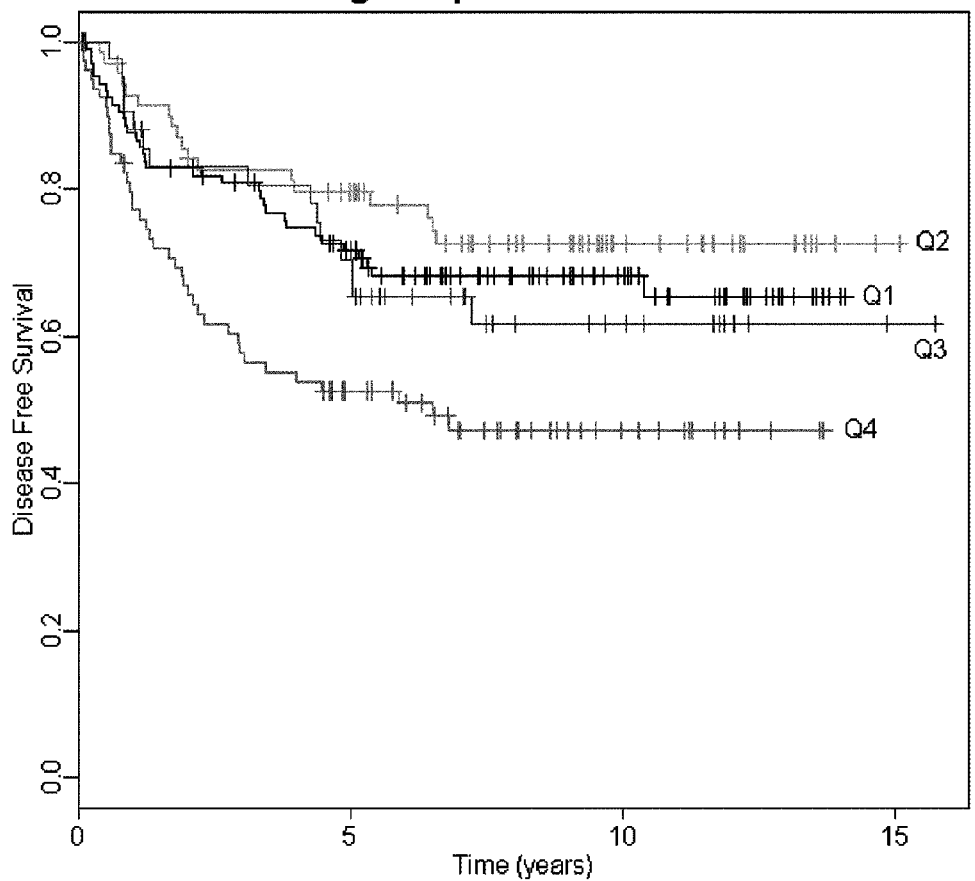

FIG. 33 represents the disease-free survival rate of state II gastric cancer patients which received only the surgery based on GCPS of the genes listed in Table 11. The blue color represents a high risk defined by GCPS.

DETAILED DESCRIPTION OF THE PREFERRED EMBODIMENTS

As an aspect to achieve the objectives, the present invention provides a marker for predicting gastric cancer prognosis comprising one or more genes selected from the group consisting of C20orf103, COL10A1, MATN3, FMO2, FOXS1, COLSA1, THBS4, CDC25B, CDK1, CLIP4, LTB4R2, NOX4, TFDP1, ADRA2C, CSK, FZD9, GALR1, GRM6, INSR, LPHN1, LYN, MRGPRX3, ALAS1, CASPS, CLYBL, CST2, HSPC159, MADCAM1, MAF, REG3A, RNF152, UCHL1, ZBED5, GPNMB, H1ST1H2AJ, RPL9, DPP6, ARL10, ISLR2, GPBAR1, CPS1, BCL11B and PCDHGAS genes.

As another aspect, the present invention provides a composition for predicting gastric cancer prognosis comprising an agent for measuring the expression level of mRNA or protein of the marker for predicting gastric cancer prognosis.

Clinical prognosis of each gastric cancer, although in the same pathologic stage, is different and the appropriate treatment method must be used according to the prognosis in order to increase the survival rate of gastric cancer patients. Accordingly, the present invention provides a composition for predicting gastric cancer prognosis comprising a marker for predicting gastric cancer prognosis and an agent for measuring the expression level thereof in order to predict accurately prognosis of the patients who were diagnosed as gastric cancer and determine the appropriate treatment direction based on the predicted prognosis for increasing the survival rate of gastric cancer patients.

As used herein, the term "marker" refers to a molecule associated quantitatively or qualitatively with the presence of biological phenomena, and the marker of the present invention refers to the gene which is the basis to predict the gastric cancer patients with good or poor prognosis.

The markers of the present invention have the significantly low p-values and high reliability for predicting gastric cancer prognosis and, in particular, the markers listed in Table 5, 7, 10, and 11 can classify the patient group to positive prognosis group or negative prognosis group, depending on the expression level thereof, and the prognosis of gastric cancer patients can be accurately predicted by measuring the expression level of the markers since the survival rate of the positive prognosis groups is higher than that of the negative prognosis group according to the Kaplan-Meier plot showing the survival rate of these groups.

As used herein, the term "prognosis" refers to the expectation on the medical development (e.g., the possibility of long-term survival, disease-free survival rate, etc.), includes positive prognosis or negative prognosis, the negative prognosis includes progression of the disease such as recurrence, tumor growth, metastasis, and drug resistance mortality, and the positive prognosis includes remission of the disease such as disease-free status, improvement of the disease such as tumor regression, or stabilization.

As used herein, the term "predicting" refers to guessing about the medical development, and, for the objective of the present invention, guessing the development of the disease (progression of the disease, improvement, recurrence of gastric cancer, tumor growth, drug resistance) of the patients who were diagnosed as gastric cancer.

In an example of the present invention, the prognosis of gastric cancer patients was predicted by classifying the patients who diagnosed with gastric cancer into positive prognosis group or negative prognosis group, and furthermore, the prognosis of gastric cancer patients was predicted by classifying the patients who diagnosed with gastric cancer of pathological stage according to the prognosis (Examples 7 to 9).

The marker for predicting gastric cancer prognosis may be preferably the combination of C20orf103, COL10A1, MATN3, FMO2, FOXS1, COL8A1 and THBS4 genes, the combination of ALAS1, C20orf103, CASP8, CLYBL, COL10A1, CST2, FMO2, FOXS1, HSPC159, MADCAM1, MAF, REG3A, RNF152, THBS4, UCHL1, ZBED5, GPNMB, H1ST1H2AJ, RPL9, DPP6, ARL10, ISLR2, GPBAR1, CPS1, BCL11B and PCDHGA8 genes, the combination of C20orf103, CDC25B, CDK1, CLIP4, LTB4R2, MATN3, NOX4 and TFDP1 genes, or the combination of ADRA2C, C20orf103, CLIP4, CSK, FZD9, GALR1, GRM6, INSR, LPHN1, LYN, MATN3, MRGPRX3 and NOX4 genes, and more preferably the combination of C20orf103, CDC25B, CDK1, CLIP4, LTB4R2, MATN3, NOX4 and TFDP1 genes, or the combination of ADRA2C, C20orf103, CLIP4, CSK, FZD9, GALR1, GRM6, INSR, LPHN1, LYN, MATN3, MRGPRX3 and NOX4 genes.

The present inventors identified that the above genes can accurately predict gastric cancer prognosis through the following process. The present inventors extracted RNA from formalin-fixed paraffin-embedded tumor tissue of gaastric cancer, measured the expression level of genes using extracted RNA and the whole-Genome DASL assay kit, and then performed standard statistical analysis using the Cox proportional hazard model in which the expression level of gene is processed as a continuous variable. As a result, 369 genes for predicting gastric cancer prognosis (Table 2) with a large correlation with disease-free survival rate by univariate analysis and the genes for predicting pathologic stage Ib/II gastric cancer prognosis (Table 3) were identified. Then, the prognosis prediction model comprising the genes in Table 5 was created by applying the superPC algorithm for the expression level of the identified genes, and the gastric cancer patients were classified into the positive prognosis group or negative prognosis group according to the prediction model. The results of Kaplan-Meier plot for the classified group verified the validity and reliability of the prognosis prediction model using markers of the present invention, by showing that the survival rate of positive prognosis group is higher than that of negative prognosis group (Example 7, and FIGS. 16, 17). In addition, the results of creating the prognosis prediction model comprising the genes in Table 7 by applying the gradient lasso algorithm for the expression level of the identified genes and classifying the gastric cancer patients into the positive prognosis group or negative prognosis group identified that the classification coincides with the clinical result (Example 8, and FIGS. 18, 19).

As used herein, the term "agent for measuring the expression levels of the markers" refers to a molecule that can be used to determine the expression levels of the marker genes or proteins encoded by these genes, and can be preferably the antibody, primer or probe which is specific to the markers.

As used herein, the term "antibody", which is the term known in the art, refers to a specific protein molecule directed to the antigenic sites. For the objective of the present invention, the antibody refers to the antibody that binds specifically to the marker of the present invention and can be prepared by conventional methods from the protein, which is encoded by the marker gene, obtained by cloning each gene into the expression vector in a conventional way. Wherein, a partial peptide which can be made from the protein is included.

As used herein, the term "primer" refers to the short nucleic acid sequence, as the nucleic acid sequence with the short free 3 terminus hydroxyl group (free 3 hydroxyl group), which can form a base pair with complementary template and functions as the starting point for copy of a template. In the present invention, gastric cancer prognosis can be predicted through whether the desired product is created by conducting PCR amplification using the sense and antisense primers of marker polynucleotide of the present invention, The PCR conditions and the length offsense and antisense primers can be modified based on what is known in the art.

As used herein, the term "probe" refers to the nucleic acid fragment such as RNA or DNA, of a few in short to hundred bases in long, which can build the specific binding with mRNA and can determine the presence of specific mRNA due to holding labelling. The probe can be prepared in the form of oligonucleotide probe, single stranded DNA probe, double stranded DNA probes, and RNA probe, etc. In the present invention, gastric cancer prognosis can be predicted through whether hybridized or not by conducting the hybridization using the marker polynucleotide of the present invention and complementary probe. The proper choice of probe and hybridization conditions can be modified based on what is known in the art.

Primers or probes of the present invention can be synthesized chemically using phosphoramidite solid support method or other well-known methods. The nucleic acid sequence can also be modified using many means known in the art. Non-limiting examples of these modifications are methylation, cap addition, substitution with one or more analogues of natural nucleotides, and modification between nucleotides, for example, the modification to the uncharged connection body (e.g., methyl phosphonate, phosphotriester, phosphoramidite, carbamates, etc.), or to the charged connection body (eg, phosphorothioate, phosphorodithioate, etc.).

In the present invention, the expression level of the marker for predicting gastric cancer prognosis can be determined by identifying the expression level of mRNA of the marker gene or the protein encoded by the gene.

As used herein, the term "measuring the expression level of mRNA" refers to the process for identifying the presence of mRNA of the marker gene in the biological sample and expression level thereof in order to predict gastric cancer prognosis and is possible by measuring the amount of mRNA. The analysis methods for this are, but not limited to, RT-PCR, competitive RT-PCR, real-time RT-PCR, RNase protection assay (RPA), northern blotting, DNA microarray chip, etc.

As used herein, the term "measuring the expression level of protein" refers to the process for identifying the presence of protein expressed in the marker gene in the biological sample and expression level thereof in order to predict gastric cancer prognosis and the amount of protein can be determined by using the antibody binding specifically to the protein expressed in the above gene. The analysis methods for this are, but not limited to, western blotting, ELISA (enzyme linked immunosorbent assay), radioimmunoassay, radioimmunodiffusion, Ouchterlony immunodiffusion, Rocket electrophoresis, tissue immunostaining, immunoprecipitation assay, complete fixation assay, FACS, protein chip, etc.

As another aspect, the present invention provides a kit for predicting gastric cancer prognosis comprising an agent for measuring the expression level of mRNA or protein of the marker for predicting gastric cancer prognosis.

A kit of the present invention can be used for identifying the expression level of the marker for predicting gastric cancer prognosis in order to predict gastric cancer prognosis.

A kit of the present invention can be RT-PCR kit, real time RT-PCR kit, real time QRT-PCR kit, microarray chip kit, or protein chip kit.

A kit of the present invention may comprise not only the primer, probe for measuring the expression level of the marker for predicting gastric cancer prognosis, or the antibody recognizing specifically the marker, but also the composition, solution or device of one or more kinds of other components suitable for analysis method.

According to the example of the present invention, a kit for measuring the expression level of mRNA of the marker genes can be a kit comprising the essential elements required for performing RT-PCR. The RT-PCR kit may comprise, in addition to the each pair of primer which are specific to the marker gene, test tube or other proper container, reaction buffer solution, deoxy nucleotides (dNTPs), Taq-polymerase and reverse transcriptase, DNase, RNase inhibitor, and DEPC-water, and sterile water.

According to another example of the present invention, a kit for measuring the expression level of protein encoded by the marker genes can comprise substrate, proper buffer solution, secondary antibody labeled with chromogenic enzyme or florescent substance, and chromogenic substrate.

According to another example of the present invention, a kit in the present invention can be a kit for detecting the marker for predicting gastric cancer prognosis, which comprises the essential elements required for performing DNA microarray chip. DNA microarray chip kit may comprise the substrate to which the gene or cDNA corresponding to the fragment thereof is attached as the probe, and the substrate may comprise the quantitative control gene or cDNA corresponding to the fragment thereof.

As another aspect, the present invention provides a method for predicting gastric cancer prognosis comprising a) obtaining the expression level or expression pattern of mRNA or protein of the marker for predicting gastric cancer prognosis in a sample collected from a gastric cancer patient; and b) comparing the expression level or expression pattern obtained in step a) with the expression level or expression pattern of mRNA or protein of the corresponding genes in a gastric cancer patient with known prognosis.

As used herein, the term "sample collected from a gastric cancer patient" may be, but not limited to, tissue, cell, whole blood, serum, plasma originated from the stomach of a gastric cancer patient, and preferably gastric tumor tissue.

As used herein, the term "gastric cancer patient with known prognosis" refers to the patient whose progression of the disease are revealed among the patients who were diagnosed as gastric cancer, for example, the patient confirmed with negative prognosis due to recurrence within 3 years after surgery or the patient confirmed with positive prognosis due to being completely cured after surgery, and prognosis of the patient whose prognosis is to be found can be accurately predicted by obtaining and comparing the expression levels or expression patterns from the samples collected form the above patient and the patient whose prognosis is to be found.

According to the example of the present invention, the prognosis can be predicted by measuring the expression levels or expression patterns of the marker genes from many gastric cancer patients, building a database of the measured values with the prognosis of the patients, and inputting the expression level or expression pattern of the patient whose prognosis is to be found into the database. In this case, the known algorithm or statistical analysis program may be used to compare the expression levels or expression patterns. In addition, the database can be subdivided further into the pathological stage, the treatment received, etc.

According to the example of the present invention, the gastric cancer patients in the steps a) and b) are the patients who received the same treatment, and the treatment can be radiation therapy, chemotherapy, chemo-radiotherapy, adjuvant chemotherapy, gastrectomy, chemotherapy or chemoradiotherapy after gastrectomy, and gastrectomy without radiation therapy after adjuvant chemotherapy or operation.

According to the example of the present invention, the gastric cancer may be the stage Ib or II gastric cancer.

In the present invention, the expression level of the marker gene can be measured in the level of mRNA or protein, and the separation of mRNA or protein from the biological sample can be performed using the publicly known process.

The analysis method for measuring the level of mRNA or protein is as described in the above.

Through the above analysis methods, the expression level of the gastric cancer gene marker measured from the sample of the gastric cancer patient with known prognosis can be compared with the expression level of the gastric cancer gene marker measured from the sample of the patient whose prognosis is to be found, and the gastric cancer prognosis can be predicted by determining the increase or decrease of the expression level. In other words, if the sample of patients whose prognosis is to be found shows the similar expression level or expression pattern as the sample of the gastric cancer patient with positive prognosis as the result of comparison of the expression levels, it can be determined to have positive prognosis, and in the contrary, if it shows the similar expression level or expression pattern as the sample of the gastric cancer patient with negative prognosis, it can be determined to have negative prognosis.

According to the example of the present invention, the prognosis can be predicted by comparing and normalizing the expression level of the marker gene with the expression level of one or more genes selected from the group consisting of the genes listed in Table 4, and then using the normalized expression level.

As another aspect, the present invention provides a method for predicting gastric cancer prognosis comprising a) measuring the expression level of mRNA or protein of the marker for predicting gastric cancer prognosis in a sample collected from a gastric cancer patient to obtain the quantified expression value; b) applying the expression value obtained in step a) to the prognosis prediction model to obtain the gastric cancer prognostic score; and c) comparing the gastric cancer prognostic score obtained in step b) with the reference value to determine prognosis of the patient.

The step a) is the step for measuring the expression level of the marker gene quantitatively. The quantified expression value of the marker gene can be achieved using known software, kits and systems to quantify the expression levels measured by the analysis method for measuring the level of mRNA or protein as described above. According to an example of the present invention, the measurement of the expression level of the marker gene can be performed using the nCounter assay kit (NanoString Technologies). In this case, the expression level of the marker gene can be normalized s by comparing with the expression level of the reference gene. According to the example of the present invention, the measured expression level of the marker gene can be normalized by comparing with the expression levels of one or more reference genes selected from the group consisting of the reference genes listed in Table 4.

According to the example of the present invention, in the step a), the expression level of mRNA or protein of C20orf103, CDC25B, CDK1, CLIP4, LTB4R2, MATN3, NOX4 and TFDP1 genes, or ADRA2C, C20orf103, CLIP4, CSK, FZD9, GALR1, GRM6, INSR, LPHN1, LYN, MATN3, MRGPRX3 and NOX4 genes can be measured.

The step b) is the step for applying the expression value obtained in step a) to the prognosis prediction model to obtain the gastric cancer prognostic score.

According to the example of the present invention, the prognosis prediction model can be expressed as:

$$[S=\beta_1 x_1+ \ldots +\beta_n x_n]$$

wherein, $x_n$ is the quantified expression value of the n-th gene, $\beta_n$ is the Cox Regression estimate of n-th gene, and S represents the gastric cancer prognostic score.

The step c) is the step for comparing the gastric cancer prognostic score obtained in step b) with the reference value to determine prognosis of the patient.

The reference value can be determined as a value in a range of cut-off value for the third quartile to cut-off value for the fourth quartile in the distribution of the multiple gastric cancer prognostic scores obtained by inputting the expression values of the marker genes from the multiple gastric cancer patients. In addition, the reference value can be determined as a value in a range of cut-off value for the second quartile to cut-off value for the third quartile in the distribution of the multiple gastric cancer prognostic scores obtained by inputting the expression values of the marker genes from the multiple gastric cancer patients. Preferably, the reference value can be determined as a value in a range of cut-off value for the third quartile to cut-off value for the fourth quartile in the distribution of the multiple gastric cancer prognostic scores obtained by inputting the expression values of the marker genes from the multiple gastric cancer patients.

The cut-off value for the quartile can be defined as the value corresponding to the 1/4, 2/4, 3/4 and 4/4 points when the multiple gastric cancer patients are distributed according to the size of the gastric cancer prognostic score. In this case, the cut-off value for the fourth quartile can be the largest score among the gastric cancer prognostic scores obtained from the patients.

According to an example of the present invention, the case of the gastric cancer prognostic score obtained in the step b) same as or larger than the reference value can be determined to have negative prognosis.

According to an example of the present invention, the cut-off value can be 0.2205 or −0.4478, and the case of the gastric cancer prognostic score obtained in the step b) same as or larger than the cut-off value can be determined to have negative prognosis. Preferably, the cut-off value can be 0.2205 if the expression levels of C20orf103, CDC25B, CDK1, CLIP4, LTB4R2, MATN3, NOX4 and TFDP1 genes are measured in the step a), and the cut-off value can be −0.4478 if the expression levels of ADRA2C, C20orf103, CLIP4, CSK, FZD9, GALR1, GRM6, INSR, LPHN1, LYN, MATN3, MRGPRX3 and NOX4 genes are measured in the step a).

In an example of the present invention, the prognosis prediction model comprising the genes in Tables 10 and 11 was created by applying the gradient lasso algorithm, the gastric cancer patients were classified into the positive prognosis group or negative prognosis group by comparing the gastric cancer prognostic value obtained by inputting the expression value into the above formula with the reference value. The results of Kaplan-Meier plot for the classified group verified the validity and reliability of the prognosis prediction model using markers of the present invention, by showing that the survival rate of negative prognosis group (high risk) is significantly lower than that of positive prognosis group (low risk) (Example 9, and FIGS. 29, 31, 32). In addition, the results of classifying the patients according to the gastric cancer prognostic value obtained by measuring the expression level of the marker gene with the patients who received only gastrectomy as the subject identified that the prognosis of the patients who received only gastrectomy can also be predicted with the marker of the present invention, by showing that the survival rate of negative prognosis group (high risk) is significantly low (Example 9, and FIG. 33).

Therefore, the gastric cancer prognosis can be accurately predicted according to the present invention, and the benefit of appropriate treatment plan in accordance with the predicted prognosis can be achieved. For example, the standard therapy or less invasive treatment options can be determined to be pursued for the patients who are judged to have positive prognosis, the treatment method for the upper stage gastric cancer patients or a very aggressive or experimental treatment can be determined to be pursued for the patients who are judged to have negative prognosis. In particular, the appropriate treatment method can be chosen according to the predicted prognosis according to the present invention for the patients who are diagnosed with stage Ib or stage II gastric cancer since they may show different prognosis. For example, the treatment methods such as surgery or anticancer drugs for the stage III gastric cancer patients can be used for the patients who are predicted to have negative prognosis among the patients may who are diagnosed with stage Ib or stage II gastric cancer.

Hereinafter, the present invention is described in more details through providing Examples. However, these Examples are merely meant to illustrate, but in no way to limit, the claimed invention.

Example 1

Selection of Gastric Cancer Patients

The present study was conducted in Samsung Medical Center and Samsung Cancer Research Institute performed in accordance with Declaration of Helsinki. The present study was approved by the Board of Directors of the Samsung Medical Center. during the period of 1994 to December 2005, cohort of 1152 patients was selected from the 1557 patients who received gastrectomy after 5-FU/LV (INT-0116 regimen) adjuvant chemotherapy according to the following criteria:

1) histological diagnosis of adenoma, tumor resection without residual tumor,
2) D2 lymph node dissection,
3) male and female over 18 years old,
4) the pathological stage Ib (T2bN0, T1N1, or Not T2aN0) to stage IV according to ADCC (American Joint Committee on Cancer) 6th edition,
5) complete preservation of surgical records and treatment records, and the patients who received 5-fluorouracil/leucovorin adjuvant chemotherapy (INT-0116 regimen) at least twice in accordance with the following methods. I.e., the patients who received chemoradiotherapy (total of 4500 cGy radiation with 180 cGy per day, 1 week/5 days, for 5 weeks) followed by administration of 5-fluoro-uracil (400 mg/m²/day) and leucovorin (20 mg/m²/day) for 5 days (1 time) and additional one time of administration of 5-fluoro-uracil (400 mg/m2/day) and leucovorin (20 mg/m²/day).

405 patients among the group of 1557 patients were excluded from the analysis due to the reasons as follows:

1) patients who received 5-FU/LV adjuvant chemotherapy less than twice (N=144),
2) patients with microscopically positive resection margin (N=73),
3) patients with double primary cancer (N=53),
4) patients with recurrent gastric cancer in the remnant stomach after subtotal gastrectomy (N=5),
5) patients without complete medical records (N=11),
6) patients who used something other than INT-0116 regimen (N=65)
7) Other (N=54).

This study was performed with final random screening of 432 patients after secondary screening of 1152 patients from 1557 patients screened primarily, and the medical characteristics for the patients are shown in Table 1. The classification of the 432 patients according to the pathological stage of gastric cancer showed the composition of 68 in stage Ib, 167 in stage II, III in stage IIIA, 19 in stage IIIB, and 67 in stage IV (Table 1).

TABLE 1

| Characteristics | N = 432 |
| --- | --- |
| Age (yr) | |
| Median, range | 53, 23-74 |
| Sex | |
| Male | 280 (64.8%) |
| Female | 152 (35.2%) |

TABLE 1-continued

| Characteristics | N = 432 |
| --- | --- |
| Type of gastrectomy | |
| Subtotal gastrectomy | 256 (59.3%) |
| Total gastrectomy | 175 (40.5%) |
| Others | 1 (0.2%) |
| Extent of surgery | |
| Resection of spleen | 73 (16.9%) |
| Resection of spleen, pancreas | 8 (1.9%) |
| Location of tumor | |
| Distal ⅓ | 231 (53.5%) |
| Middle ⅓ | 130 (30.1%) |
| Cardia, GE junction | 53 (12.3%) |
| Whole, multicentric | 17 (3.9%) |
| Remnant stomach | 1 (0.2%) |
| Grade | |
| Well to moderately differentiated tubular | 111 (25.7%) |
| Poorly differentiated tubular | 200 (46.3%) |
| Signet ring cell | 101 (23.4%) |
| Mucinous | 14 (3.2%) |
| Papillary | 3 (0.7%) |
| Hepatoid | 2 (0.5%) |
| Others | 1 (0.2%) |

Example 2

RNA Extraction from Gastric Tumor

RNA was extracted from the gastric tumor of the gastric cancer patients screened finally in Example 1. For this, primary tumor paraffin block consisting of the largest tumor was selected. RNA was extracted from 2 to 4 sections of 4 μm thickness in formalin-fixed, paraffin-embedded tissue, and the non-tumor elements were removed by microdissection before moving to the extraction tube. Then, whole RNA was extracted using the High Pure RNA Paraffin Kit (Roche Diagnostic, Mannheim, Germany) or E.Z.N.A.® FFPE RNA Isolation Kit (Omega Bio-Tek, Norcross, Ga., USA) according to the manufacturer's instructions. The concentration of the extracted RNA was determined using a NanoDrop 8000 spectrophotometer (Thermo Scientific), and was stored at a low temperature of −80° C. before use. In the experiment, the RNA sample with concentration less than 40 ng/μl and the A260/A280 ratio less than 1.5 or A260/230 ratio less than 1.0 was not used in the analysis as the inappropriate sample.

Example 3

Whole Genome Expression Profiling

Illumina Whole-Genome DASL® (cDNA-mediated Annealing, Selection, Extension, and Ligation, Illumina, USA) assay was performed with RNA 200 ng extracted from Example 2 according to the manufacturer's instructions. First, PCR template was prepared by reverse-transcribing the whole RNA into cDNA using biotinylated oligo-dT and random primers, annealing biotinylated cDNA to a pair of query oligos, extending the gap between query oligos, and then ligating. Subsequently, the PCR products amplified using a pair of universal PCR primers were hybridized to the Human-Ref-8 Expression BeadChip (>24,000 annotated transcripts). After hybridization, HumanRef 8 BeadChips was scanned using iScan (Illumina, USA).

Example 4

Quality Control of Whole-Genome DASL Assay

The probe called as "absent" among 24,526 probes of HumanRef-8 Expression BeadChip used in Example 3 was filtered and removed. 17,418 probes left after filtering were used in the later analysis. The intensity of the probe was modified by logarithm with base 2) and normalized using the quantile normalization algorithm. As a result, the statistical analysis was performed using the 17,418 probes and 432 samples.

Example 5

Identification of Gastric Cancer Predicting Gene

In order to identify the gene whose expression level is associated with clinical results such as disease-free survival (DES), standard statistical analysis was performed using Cox proportional hazard model to process the expression levels of genes as continuous variables. As a result, 369 probes with the significant association of disease-free survival rate among 17,418 probes were identified through the univariate analysis, and the results are shown in Table 2 ($p<0.001$).

In addition, since it is important to predict the prognosis of stage Ib/II patients, gastric cancer prognostic gene specific to stage Ib/II was identified with the sample collected from stage Ib/II patients among the samples as the subject in the same way as above, and the results are shown in Table 3. The p value in Table 3 represents the degree of effects of the expression levels of the genes on the clinical prognosis with lower p value affecting more significantly the prognosis, and the hazard ratio represents the degree of effects on the recurrence rate of gastric cancer with significant meaning of increase or decrease of the figures.

According to Tables 2 and 3, the presence of a number of stage Ib/II-specific prognostic genes was identified although prognostic genes identified with the entire group of patients as the subject coincide with prognostic genes identified with stage Ib/II patients as the subject.

TABLE 2

| PROBE_ID (Illumina) | SYMBOL | Accession number | pvalue | Hazard ratio |
|---|---|---|---|---|
| ILMN_1713561 | C20orf103 | NM_012261.2 | 1.48E-09 | 1.302187 |
| ILMN_1811790 | FOXS1 | NM_004118.3 | 1.65E-07 | 1.426582 |
| ILMN_1736078 | THBS4 | NM_003248.3 | 6.59E-07 | 1.320863 |
| ILMN_1672776 | COL10A1 | NM_000493.3 | 8.79E-07 | 1.657158 |
| ILMN_1732158 | FMO2 | NM_001460.2 | 9.81E-07 | 1.262049 |
| ILMN_2402392 | COL8A1 | NM_001850.3 | 1.36E-06 | 1.469684 |
| ILMN_2206746 | BGN | NM_001711.3 | 1.83E-05 | 5.841759 |
| ILMN_1780667 | WDR51A | NM_015426.3 | 2.38E-05 | 0.727733 |
| ILMN_1673843 | CST2 | NM_001322.2 | 2.59E-05 | 1.289074 |
| ILMN_1775931 | EPHA3 | NM_005233.3 | 3.22E-05 | 1.313913 |
| ILMN_1749846 | OMD | NM_005014.1 | 3.31E-05 | 1.360159 |
| ILMN_1755318 | HIST1H2AJ | NM_021066.2 | 3.56E-05 | 0.660616 |
| ILMN_1677636 | COMP | NM_000095.2 | 4.31E-05 | 1.204699 |
| ILMN_2316386 | GPBAR1 | NM_170699.2 | 4.93E-05 | 2.746716 |
| ILMN_1740265 | ACOT7 | NM_181864.2 | 5.57E-05 | 0.487482 |
| ILMN_1774350 | MYOZ3 | NM_133371.2 | 7.75E-05 | 1.2456 |
| ILMN_2093500 | ZBED5 | NM_021211.2 | 8.06E-05 | 1.403335 |
| ILMN_1701331 | UBE2M | NM_003969.3 | 8.35E-05 | 0.139592 |
| ILMN_2071809 | MGP | NM_000900.2 | 9.96E-05 | 1.89168 |
| ILMN_1759792 | CLIP4 | NM_024692.3 | 0.000103 | 1.264165 |
| ILMN_2188451 | HIST1H2AH | NM_080596.1 | 0.00011 | 0.648883 |
| ILMN_2138589 | MERTK | NM_006343.2 | 0.000117 | 1.344156 |
| ILMN_1735996 | NOX4 | NM_016931.2 | 0.00013 | 1.273066 |
| ILMN_1782329 | HIST1H4L | NM_003546.2 | 0.000131 | 0.752221 |
| ILMN_1726603 | ATP5I | NM_007100.2 | 0.000137 | 0.076217 |
| ILMN_1695079 | ZNF101 | NM_033204.2 | 0.000146 | 0.669062 |
| ILMN_1797693 | BRI3BP | NM_080626.5 | 0.000171 | 0.410778 |
| ILMN_1653553 | C14orf80 | NM_173608.1 | 0.00019 | 0.500153 |
| ILMN_1792538 | CD7 | NM_006137.6 | 0.000192 | 0.43232 |
| ILMN_1757387 | UCHL1 | NM_004181.3 | 0.000201 | 1.653798 |
| ILMN_1693597 | ZNF287 | NM_020653.1 | 0.000208 | 1.194469 |
| ILMN_1673548 | HSPC159 | NM_014181.1 | 0.000209 | 0.680392 |
| ILMN_1753524 | HIST1H2AB | NM_003513.2 | 0.000211 | 0.72192 |
| ILMN_2382679 | REG3A | NM_138938.1 | 0.000232 | 0.863324 |
| ILMN_1769168 | ARL10 | NM_173664.4 | 0.000235 | 1.225049 |
| ILMN_2071826 | RNF152 | NM_173557.1 | 0.000264 | 1.232257 |
| ILMN_1719543 | MAF | NM_005360.3 | 0.000267 | 1.166273 |
| ILMN_1711566 | TIMP1 | NM_003254.2 | 0.000268 | 5.209361 |
| ILMN_2163873 | FNDC1 | NM_032532.2 | 0.000292 | 1.275913 |
| ILMN_1685433 | COL8A1 | NM_020351.2 | 0.0003 | 1.530905 |
| ILMN_2115696 | USP42 | NM_032172.2 | 0.000308 | 1.158447 |
| ILMN_1801205 | GPNMB | NM_001005340.1 | 0.000313 | 1.298661 |
| ILMN_1712430 | ATP5G1 | NM_005175.2 | 0.000346 | 0.76876 |
| ILMN_1710752 | NAPRT1 | NM_145201.3 | 0.000351 | 0.281588 |
| ILMN_2168166 | ASPN | NM_017680.3 | 0.000355 | 1.390402 |
| ILMN_1787749 | CASP8 | NM_033356.3 | 0.000365 | 0.779592 |
| ILMN_1727709 | GPBAR1 | NM_170699.2 | 0.000365 | 1.285664 |
| ILMN_1765557 | OLFML2B | NM_015441.1 | 0.000368 | 1.226139 |
| ILMN_1796734 | SPARC | NM_003118.2 | 0.000397 | 1.216715 |
| ILMN_2392803 | COL11A1 | NM_001854.3 | 0.000398 | 1.203319 |
| ILMN_1750180 | HIST1H2BB | NM_021062.2 | 0.000405 | 0.762857 |

TABLE 2-continued

| PROBE_ID (Illumina) | SYMBOL | Accession number | pvalue | Hazard ratio |
|---|---|---|---|---|
| ILMN_2300970 | ETFB | NM_001014763.1 | 0.000405 | 0.26307 |
| ILMN_2396875 | IGFBP3 | NM_001013398.1 | 0.000413 | 1.252929 |
| ILMN_1750052 | NOL14 | NM_003703.1 | 0.000417 | 0.519811 |
| ILMN_2151368 | NOL12 | NM_024313.2 | 0.00043 | 1.217182 |
| ILMN_2330570 | LEPR | NM_001003679.1 | 0.000455 | 1.303249 |
| ILMN_1732782 | SCN2A | NM_001040142.1 | 0.000467 | 1.210705 |
| ILMN_1708143 | FAM127A | NM_001078171.1 | 0.000473 | 1.250246 |
| ILMN_2219867 | KRT20 | NM_019010.1 | 0.000544 | 0.761421 |
| ILMN_1800331 | PTCH1 | NM_001083605.1 | 0.000571 | 1.248174 |
| ILMN_1726815 | HIST1H3G | NM_003534.2 | 0.000597 | 0.777786 |
| ILMN_1677652 | PREX2 | NM_024870.2 | 0.000601 | 1.168492 |
| ILMN_1758067 | RGS4 | NM_005613.3 | 0.000603 | 1.239717 |
| ILMN_1712751 | HADHA | NM_000182.4 | 0.00065 | 0.260972 |
| ILMN_1710522 | RUNX1T1 | NM_175635.1 | 0.000655 | 1.238393 |
| ILMN_1712532 | CARD9 | NM_052813.3 | 0.000658 | 1.29096 |
| ILMN_1770290 | CNN2 | NM_201277.1 | 0.00069 | 3.212723 |
| ILMN_2355786 | BTNL3 | NM_197975.1 | 0.000751 | 0.704169 |
| ILMN_1749878 | FAM124B | NM_024785.2 | 0.000755 | 1.269953 |
| ILMN_1712088 | CLYBL | NM_206808.1 | 0.00078 | 0.804096 |
| ILMN_1677747 | TMPO | NM_003276.1 | 0.000783 | 0.716288 |
| ILMN_1675706 | APOA4 | NM_000482.3 | 0.000795 | 0.83371 |
| ILMN_2073184 | S1PR5 | NM_030760.4 | 0.000801 | 1.213767 |
| ILMN_1735877 | EFEMP1 | NM_004105.3 | 0.000844 | 1.289706 |
| ILMN_1758128 | CYGB | NM_134268.3 | 0.000856 | 1.926103 |
| ILMN_1729033 | RPL9 | NM_001024921.2 | 0.000901 | 0.826367 |
| ILMN_1678669 | RRM2 | NM_001034.1 | 0.000917 | 0.848107 |
| ILMN_1809866 | WDR74 | NM_018093.1 | 0.000925 | 0.479147 |
| ILMN_1662824 | MADCAM1 | NM_130760.2 | 0.000956 | 0.774827 |
| ILMN_2328094 | DACT1 | NM_001079520.1 | 0.000977 | 1.243186 |
| ILMN_1729368 | FZD8 | NM_031866.1 | 0.001017 | 1.195987 |
| ILMN_1738116 | TMEM119 | NM_181724.1 | 0.001036 | 1.182145 |
| ILMN_1810486 | RAB34 | NM_031934.3 | 0.001053 | 1.220139 |
| ILMN_1712400 | SERPINB6 | NM_004568.4 | 0.001071 | 0.214418 |
| ILMN_1780170 | APOD | NM_001647.2 | 0.001092 | 1.201164 |
| ILMN_1671557 | PHLDA2 | NM_003311.3 | 0.001116 | 0.736297 |
| ILMN_2077094 | C11orf2 | NM_013265.2 | 0.001117 | 0.405725 |
| ILMN_2219681 | RBP2 | NM_004164.2 | 0.001131 | 0.741382 |
| ILMN_2051972 | GPC3 | NM_004484.2 | 0.001168 | 1.214438 |
| ILMN_2372200 | ZNF586 | NM_017652.2 | 0.001199 | 0.568325 |
| ILMN_1738684 | NRXN2 | NM_138734.1 | 0.001203 | 1.202815 |
| ILMN_1792748 | CPS1 | NM_001875.2 | 0.001224 | 0.827387 |
| ILMN_1752299 | RAB6B | NM_016577.3 | 0.001235 | 1.190276 |
| ILMN_1701403 | HIP1 | NM_005338.4 | 0.001245 | 1.219317 |
| ILMN_1763491 | CKMT1B | NM_020990.3 | 0.00128 | 0.80908 |
| ILMN_1722898 | SFRP2 | NM_003013.2 | 0.001291 | 1.269536 |
| ILMN_1705468 | PIK3CA | NM_006218.2 | 0.00131 | 1.226938 |
| ILMN_1803570 | BRI3BP | NM_080626.5 | 0.001319 | 0.867957 |
| ILMN_1776077 | SF1 | NM_201997.1 | 0.001347 | 1.309907 |
| ILMN_2118129 | ITLN2 | NM_080878.2 | 0.001364 | 0.872461 |
| ILMN_1717163 | F13A1 | NM_000129.3 | 0.001373 | 1.300682 |
| ILMN_1692739 | ISLR2 | NM_020851.1 | 0.001375 | 1.196592 |
| ILMN_2067709 | TFB2M | NM_022366.1 | 0.001385 | 0.653243 |
| ILMN_1697363 | C20orf27 | NM_001039140.1 | 0.001432 | 0.714003 |
| ILMN_1740523 | KTN1 | NM_182926.2 | 0.0015 | 1.203121 |
| ILMN_2398664 | RNF34 | NM_194271.1 | 0.001501 | 0.504034 |
| ILMN_2148469 | RASL11B | NM_023940.2 | 0.001508 | 1.149716 |
| ILMN_1747067 | NPAS1 | NM_002517.2 | 0.001542 | 0.781286 |
| ILMN_1792110 | C10orf76 | NM_024541.2 | 0.001576 | 1.184364 |
| ILMN_1714438 | MUTYH | NM_001048172.1 | 0.001606 | 1.246579 |
| ILMN_1651964 | ABCC5 | NM_001023587.1 | 0.001622 | 1.21205 |
| ILMN_1764709 | MAFB | NM_005461.3 | 0.001623 | 1.207708 |
| ILMN_1652461 | PARD3B | NM_152526.4 | 0.001645 | 1.255893 |
| ILMN_1694539 | MAP3K6 | NM_004672.3 | 0.001647 | 1.197227 |
| ILMN_1765532 | RDBP | NM_002904.5 | 0.001667 | 0.463459 |
| ILMN_1711009 | ISLR | NM_201526.1 | 0.001668 | 1.196724 |
| ILMN_1811426 | TMTC1 | NM_175861.2 | 0.001677 | 1.226595 |
| ILMN_1702806 | PDCL3 | NM_024065.3 | 0.001685 | 0.589571 |
| ILMN_1688067 | SEPT5 | NM_002688.4 | 0.001746 | 1.142858 |
| ILMN_1770800 | PODN | NM_153703.3 | 0.001767 | 2.010032 |
| ILMN_1787115 | WWTR1 | NM_015472.3 | 0.001836 | 1.205927 |
| ILMN_1757060 | CAMK2D | NM_172115.1 | 0.001909 | 0.658325 |
| ILMN_2350634 | EFEMP1 | NM_018894.1 | 0.001942 | 1.276171 |
| ILMN_1672611 | CDH11 | NM_001797.2 | 0.00196 | 1.235423 |
| ILMN_2234310 | GLTPD1 | NM_001029885.1 | 0.001975 | 1.183448 |
| ILMN_1680419 | ASB7 | NM_024708.2 | 0.001983 | 0.664755 |
| ILMN_1673586 | SLC6A6 | NM_003043.3 | 0.00202 | 1.368342 |
| ILMN_1777263 | MEOX2 | NM_005924.4 | 0.002037 | 1.200134 |
| ILMN_1670903 | NAT2 | NM_000015.2 | 0.002038 | 0.678685 |

TABLE 2-continued

| PROBE_ID (Illumina) | SYMBOL | Accession number | pvalue | Hazard ratio |
|---|---|---|---|---|
| ILMN_1673721 | EXO1 | NM_006027.3 | 0.002053 | 0.692379 |
| ILMN_1667112 | FBXO7 | NM_012179.3 | 0.002055 | 0.716782 |
| ILMN_2273911 | ACSL5 | NM_203380.1 | 0.00209 | 0.784848 |
| ILMN_1734950 | LOXL1 | NM_005576.2 | 0.002152 | 1.22384 |
| ILMN_1793965 | PCDHGA8 | NM_032088.1 | 0.002196 | 0.767728 |
| ILMN_1733396 | CDC25A | NM_001789.2 | 0.002317 | 0.837309 |
| ILMN_1729188 | HAMP | NM_021175.2 | 0.002365 | 1.168372 |
| ILMN_1718646 | MMP15 | NM_002428.2 | 0.002444 | 0.85565 |
| ILMN_2230178 | DAND5 | NM_152654.2 | 0.002497 | 0.764252 |
| ILMN_1767665 | LOC493869 | NM_001008397.1 | 0.002565 | 1.187629 |
| ILMN_1657683 | C1orf198 | NM_032800.1 | 0.002578 | 1.288479 |
| ILMN_1741356 | PRICKLE1 | NM_153026.1 | 0.002616 | 1.505195 |
| ILMN_1677043 | AKR7A2 | NM_003689.2 | 0.002709 | 0.468292 |
| ILMN_1721559 | FABP6 | NM_001445.2 | 0.002889 | 1.130136 |
| ILMN_1720496 | GUCY1A2 | NM_000855.1 | 0.002901 | 1.22875 |
| ILMN_2159044 | PDF | NM_022341.1 | 0.002908 | 0.676684 |
| ILMN_1708369 | EPS15L1 | NM_021235.1 | 0.002965 | 1.214545 |
| ILMN_1743579 | WDR4 | NM_033661.3 | 0.002985 | 0.73777 |
| ILMN_2249018 | LOC389816 | NM_001013653.1 | 0.003016 | 0.773289 |
| ILMN_1798379 | HNT | NM_001048209.1 | 0.003065 | 1.19188 |
| ILMN_1779558 | GAS6 | NM_000820.1 | 0.003092 | 1.4833 |
| ILMN_2150095 | CES4 | NM_016280.1 | 0.003155 | 1.161699 |
| ILMN_1726392 | NIN | NM_020921.3 | 0.003165 | 0.684082 |
| ILMN_2044832 | NOL5A | NM_006392.2 | 0.003244 | 0.750471 |
| ILMN_1742238 | SET | NM_003011.2 | 0.003279 | 0.688373 |
| ILMN_1662523 | C3 | NM_000064.2 | 0.003297 | 1.660256 |
| ILMN_1778924 | PDE1A | NM_001003683.1 | 0.003326 | 1.172318 |
| ILMN_2314140 | PAX6 | NM_005624.2 | 0.003344 | 0.616935 |
| ILMN_1737817 | CCL25 | NM_005624.2 | 0.003382 | 0.894426 |
| ILMN_2381296 | GSTZ1 | NM_145871.1 | 0.003384 | 0.755576 |
| ILMN_1714041 | PLCB3 | NM_000932.1 | 0.003396 | 0.730519 |
| ILMN_1668714 | SNF1LK2 | NM_015191.1 | 0.003424 | 1.17226 |
| ILMN_1743103 | SH3PXD2A | NM_014631.2 | 0.003465 | 1.16748 |
| ILMN_1755737 | TRABD | NM_025204.2 | 0.003492 | 0.259653 |
| ILMN_1795228 | ZFAND5 | NM_006007.1 | 0.003506 | 0.824405 |
| ILMN_1654737 | TRIM32 | NM_012210.3 | 0.003522 | 0.79033 |
| ILMN_1752249 | FAM38A | NM_014745.1 | 0.00353 | 2.322901 |
| ILMN_1730740 | VSIG8 | NM_001013661.1 | 0.00357 | 1.197703 |
| ILMN_1672660 | MBP | NM_001025100.1 | 0.003626 | 1.145594 |
| ILMN_1738883 | RNF135 | NM_197939.1 | 0.003632 | 0.631082 |
| ILMN_1718387 | LOR | NM_000427.2 | 0.003648 | 1.140323 |
| ILMN_1718754 | CD207 | NM_015717.2 | 0.003649 | 1.139594 |
| ILMN_2392261 | FABP6 | NM_001445.2 | 0.003697 | 1.128338 |
| ILMN_1653251 | HIST1H1B | NM_005322.2 | 0.003721 | 0.759297 |
| ILMN_1736178 | AEBP1 | NM_001129.3 | 0.003766 | 1.540385 |
| ILMN_2253732 | ST8SIA4 | NM_175052.1 | 0.003779 | 1.242747 |
| ILMN_1812795 | RUNX1T1 | NM_004349.2 | 0.003809 | 1.130963 |
| ILMN_1779373 | HIST1H2BF | NM_003522.3 | 0.003828 | 0.82018 |
| ILMN_1753823 | IL17D | NM_138284.1 | 0.003852 | 1.156443 |
| ILMN_1676311 | COX18 | NM_173827.2 | 0.003858 | 0.70773 |
| ILMN_1809267 | CLCC1 | NM_015127.3 | 0.003864 | 1.167778 |
| ILMN_1723035 | OLR1 | NM_002543.3 | 0.003871 | 1.188039 |
| ILMN_1720838 | DECR1 | NM_001359.1 | 0.003908 | 0.644174 |
| ILMN_1791569 | PLXNA1 | NM_032242.2 | 0.003943 | 1.230557 |
| ILMN_2223056 | TBX10 | NM_005995.3 | 0.003953 | 0.78329 |
| ILMN_1761084 | FNDC5 | NM_153756.1 | 0.004021 | 1.255781 |
| ILMN_2323338 | NR1I2 | NM_022002.2 | 0.004034 | 0.72455 |
| ILMN_2340131 | MAPK10 | NM_138981.1 | 0.004035 | 1.186702 |
| ILMN_2062468 | IGFBP7 | NM_001553.1 | 0.004039 | 1.445932 |
| ILMN_1653940 | USP2 | NM_004205.3 | 0.004084 | 0.705592 |
| ILMN_2276461 | MAP2 | NM_031845.2 | 0.004109 | 1.185406 |
| ILMN_2215881 | ARHGAP11B | NM_001039841.1 | 0.004154 | 0.844611 |
| ILMN_1678170 | MME | NM_000902.3 | 0.004174 | 0.838642 |
| ILMN_2186983 | ANXA8L2 | NM_001630.2 | 0.004193 | 1.118791 |
| ILMN_1758209 | UACA | NM_001008224.1 | 0.004224 | 1.240201 |
| ILMN_1663171 | MATN3 | NM_002381.4 | 0.004238 | 1.341007 |
| ILMN_1749789 | HIST1H1D | NM_005320.2 | 0.004263 | 0.6848 |
| ILMN_1696675 | CES2 | NM_003869.4 | 0.004291 | 0.557116 |
| ILMN_1721127 | HIST1H3D | NM_003530.3 | 0.004306 | 0.697261 |
| ILMN_1680314 | TXN | NM_003329.2 | 0.004463 | 0.832985 |
| ILMN_1790026 | SFRP5 | NM_003015.2 | 0.004465 | 1.120384 |
| ILMN_2103685 | DEPDC1B | NM_018369.1 | 0.00447 | 0.706872 |
| ILMN_1723111 | HIST1H4A | NM_003538.3 | 0.004505 | 0.844986 |
| ILMN_2212878 | ESM1 | NM_007036.2 | 0.004516 | 1.298296 |
| ILMN_1654946 | ZSCAN18 | NM_023926.3 | 0.004528 | 1.147692 |
| ILMN_1661010 | ZMAT1 | NM_001011656.1 | 0.004591 | 1.147018 |
| ILMN_1813625 | TRIM25 | NM_005082.4 | 0.00462 | 0.825171 |
| ILMN_1791006 | AHI1 | NM_017651.3 | 0.004662 | 1.181987 |

TABLE 2-continued

| PROBE_ID (Illumina) | SYMBOL | Accession number | pvalue | Hazard ratio |
|---|---|---|---|---|
| ILMN_1660079 | RNF44 | NM_014901.4 | 0.004707 | 1.349436 |
| ILMN_2095660 | TMEM156 | NM_024943.1 | 0.004727 | 0.677499 |
| ILMN_1687652 | TGFB3 | NM_003239.1 | 0.00484 | 1.158037 |
| ILMN_1765189 | PTK2B | NM_173174.1 | 0.004858 | 0.709154 |
| ILMN_1654920 | HNRPH3 | NM_012207.1 | 0.004879 | 1.226349 |
| ILMN_1678710 | PHYHIPL | NM_032439.1 | 0.004902 | 1.296577 |
| ILMN_1748591 | ODC1 | NM_002539.1 | 0.004913 | 0.843751 |
| ILMN_2413278 | RPL13 | NM_033251.1 | 0.004966 | 0.633774 |
| ILMN_2354855 | OTUB1 | NM_003089.1 | 0.005013 | 0.456697 |
| ILMN_1747146 | TSG101 | NM_006292.2 | 0.00502 | 0.740316 |
| ILMN_1792682 | MCTP2 | NM_018349.2 | 0.005074 | 1.214269 |
| ILMN_2401779 | FAM102A | NM_001035254.1 | 0.005094 | 0.480071 |
| ILMN_1667641 | ACACA | NM_198839.1 | 0.005104 | 1.164908 |
| ILMN_2106818 | MBIP | NM_016586.1 | 0.005113 | 1.299724 |
| ILMN_2324989 | IKIP | NM_201612.1 | 0.005168 | 0.825236 |
| ILMN_1741994 | L3MBTL3 | NM_032438.1 | 0.005177 | 1.15951 |
| ILMN_2223941 | FBLN5 | NM_006329.2 | 0.005178 | 1.411779 |
| ILMN_2092536 | HSPE1 | NM_002157.1 | 0.005197 | 0.635259 |
| ILMN_1752226 | P2RY11 | NM_002566.4 | 0.005209 | 0.481078 |
| ILMN_1784871 | FASN | NM_004104.4 | 0.005254 | 0.291412 |
| ILMN_1677385 | C8orf40 | NM_138436.2 | 0.005319 | 1.225286 |
| ILMN_1736112 | ARHGAP10 | NM_024605.3 | 0.005348 | 1.242786 |
| ILMN_2229649 | KCTD12 | NM_138444.3 | 0.005351 | 1.219597 |
| ILMN_1669497 | OSBPL10 | NM_017784.3 | 0.005372 | 1.17703 |
| ILMN_1665260 | FLJ25996 | NM_001001699.1 | 0.005385 | 1.214995 |
| ILMN_2355033 | KIAA1147 | NM_001080392.1 | 0.005454 | 1.203143 |
| ILMN_1768393 | SNRPD1 | NM_006938.2 | 0.005693 | 0.702623 |
| ILMN_1671058 | CDX2 | NM_001265.2 | 0.005696 | 0.857541 |
| ILMN_1704730 | CD93 | NM_012072.3 | 0.005717 | 1.153984 |
| ILMN_1717888 | KHK | NM_000221.2 | 0.00574 | 0.833244 |
| ILMN_2385647 | ALAS1 | NM_000688.4 | 0.005756 | 0.857815 |
| ILMN_2385672 | ELN | NM_001081754.1 | 0.005759 | 1.253974 |
| ILMN_1754655 | TTLL5 | NM_015072.3 | 0.00581 | 0.810275 |
| ILMN_1711005 | CDC25A | NM_001789.2 | 0.005869 | 0.770725 |
| ILMN_2186137 | RRAD | NM_004165.1 | 0.005904 | 1.289988 |
| ILMN_1769782 | LAX1 | NM_017773.2 | 0.005938 | 0.838368 |
| ILMN_1738552 | SLC1A3 | NM_004172.3 | 0.005942 | 1.301663 |
| ILMN_1726204 | SCRG1 | NM_007281.1 | 0.005979 | 1.165889 |
| ILMN_2390526 | RARB | NM_000965.2 | 0.005985 | 1.386201 |
| ILMN_1695631 | CHP2 | NM_022097.2 | 0.005994 | 0.827999 |
| ILMN_1786612 | PSME2 | NM_002818.2 | 0.006016 | 0.649769 |
| ILMN_1747716 | ALDOB | NM_000035.2 | 0.006038 | 0.890305 |
| ILMN_2234187 | CDO1 | NM_001801.2 | 0.006053 | 1.25975 |
| ILMN_1761000 | ASAH3L | NM_001010887.2 | 0.006076 | 0.85266 |
| ILMN_2121272 | PDE10A | NM_006661.1 | 0.006077 | 1.164521 |
| ILMN_1813295 | LMO3 | NM_018640.3 | 0.006127 | 1.200168 |
| ILMN_1686804 | CCRK | NM_012119.3 | 0.006219 | 1.2044 |
| ILMN_1736176 | PLK1 | NM_005030.3 | 0.00622 | 0.779772 |
| ILMN_1779448 | EFHD1 | NM_025202.2 | 0.006236 | 1.163807 |
| ILMN_1788729 | TCF23 | NM_175769.1 | 0.006252 | 1.172746 |
| ILMN_1657836 | PLEKHG2 | NM_022835.1 | 0.006326 | 1.256047 |
| ILMN_1758597 | NAGS | NM_153006.2 | 0.006357 | 0.826079 |
| ILMN_1731374 | CPE | NM_001873.1 | 0.006365 | 1.172434 |
| ILMN_2125395 | GPR128 | NM_032787.1 | 0.006386 | 0.860916 |
| ILMN_1670638 | PITPNC1 | NM_181671.1 | 0.006404 | 1.174446 |
| ILMN_1658989 | MEX3B | NM_032246.3 | 0.006405 | 0.660644 |
| ILMN_1712065 | FAM19A5 | NM_001082967.1 | 0.006442 | 1.132281 |
| ILMN_1717261 | HLA-DRB3 | NM_022555.3 | 0.006482 | 0.877062 |
| ILMN_1663786 | EPB41 | NM_203342.1 | 0.006503 | 0.757261 |
| ILMN_1692511 | TMEM106C | NM_024056.2 | 0.00651 | 0.630838 |
| ILMN_1654246 | SIRT6 | NM_016539.1 | 0.006513 | 0.864446 |
| ILMN_1811278 | RNF186 | NM_019062.1 | 0.006532 | 0.704422 |
| ILMN_1700306 | OCIAD2 | NM_001014446.1 | 0.006614 | 0.845453 |
| ILMN_2141444 | RPL18A | NM_000980.2 | 0.006624 | 0.140945 |
| ILMN_1754576 | KRT6C | NM_173086.3 | 0.006692 | 1.137425 |
| ILMN_1745329 | PRR14 | NM_024031.2 | 0.006695 | 0.65701 |
| ILMN_1772645 | AGK | NM_018238.2 | 0.006759 | 1.207978 |
| ILMN_1766425 | REPS2 | NM_004726.2 | 0.006798 | 1.224906 |
| ILMN_1803376 | AEBP2 | NM_153207.3 | 0.006913 | 0.688622 |
| ILMN_1695093 | SLC7A8 | NM_012244.2 | 0.00695 | 0.803152 |
| ILMN_1719089 | EXO1 | NM_130398.2 | 0.006962 | 0.746364 |
| ILMN_1665832 | ID1 | NM_181353.1 | 0.006984 | 0.853496 |
| ILMN_1675219 | WDHD1 | NM_007086.3 | 0.007008 | 0.790273 |
| ILMN_1797219 | CLCA1 | NM_001285.3 | 0.007035 | 0.877425 |
| ILMN_1739594 | ACOT11 | NM_147161.2 | 0.007105 | 0.637043 |
| ILMN_2094942 | 40238 | NM_001012415.1 | 0.007129 | 1.183848 |
| ILMN_1657495 | KIAA0152 | NM_014730.2 | 0.007174 | 0.714483 |
| ILMN_1729287 | NMUR1 | NM_006056.3 | 0.007175 | 1.19547 |

TABLE 2-continued

| PROBE_ID (Illumina) | SYMBOL | Accession number | pvalue | Hazard ratio |
|---|---|---|---|---|
| ILMN_1804090 | SLC25A10 | NM_012140.3 | 0.007205 | 0.697334 |
| ILMN_1713807 | MAN1C1 | NM_020379.2 | 0.007212 | 1.218037 |
| ILMN_1801068 | DACT1 | NM_001079520.1 | 0.007228 | 1.155005 |
| ILMN_2316236 | HOPX | NM_032495.5 | 0.007247 | 1.239065 |
| ILMN_1736670 | PPP1R3C | NM_005398.4 | 0.007302 | 1.2415 |
| ILMN_1676058 | MAGOHB | NM_018048.3 | 0.007329 | 0.706763 |
| ILMN_1813207 | MRPS9 | NM_182640.1 | 0.007392 | 0.85342 |
| ILMN_2389935 | FYTTD1 | NM_001011537.1 | 0.007408 | 0.707889 |
| ILMN_2387995 | ANTXR1 | NM_032208.1 | 0.007426 | 1.291281 |
| ILMN_1740160 | PLCG1 | NM_182811.1 | 0.007472 | 1.372496 |
| ILMN_2299862 | KCNH1 | NM_172362.1 | 0.007479 | 0.732409 |
| ILMN_1715401 | MT1G | NM_005950.1 | 0.007518 | 0.815893 |
| ILMN_2232854 | FAP | NM_004460.2 | 0.007528 | 1.122417 |
| ILMN_1712506 | DPP6 | NM_130797.2 | 0.007555 | 0.808478 |
| ILMN_2289623 | TTC36 | NM_001080441.1 | 0.007579 | 0.847973 |
| ILMN_2241168 | MAFF | NM_152878.1 | 0.007592 | 0.851913 |
| ILMN_1665761 | BCL11B | NM_138576.2 | 0.007679 | 0.856148 |
| ILMN_1721495 | ADAMTSL2 | NM_014694.2 | 0.007681 | 1.468854 |
| ILMN_1811277 | TRIM13 | NM_213590.1 | 0.007696 | 0.782911 |
| ILMN_1719616 | DNASE1 | NM_005223.3 | 0.007756 | 0.799984 |
| ILMN_744387 | KCNIP1 | NM_001034838.1 | 0.00779 | 1.185425 |
| ILMN_1810274 | HOXB2 | NM_002145.3 | 0.007796 | 1.183641 |
| ILMN_1776490 | C17orf53 | NM_024032.2 | 0.007804 | 0.797121 |
| ILMN_1776314 | CHRNA10 | NM_020402.2 | 0.007829 | 0.753693 |
| ILMN_2398184 | NCAM1 | NM_000615.1 | 0.007903 | 0.721315 |
| ILMN_2405592 | TMEM93 | NM_031298.2 | 0.007932 | 0.816861 |
| ILMN_1661695 | IRAK3 | NM_007199.1 | 0.007934 | 1.16293 |
| ILMN_1758852 | ENTPD7 | NM_020354.2 | 0.007942 | 0.786463 |
| ILMN_1784749 | GAS6 | NM_000820.1 | 0.007988 | 1.496952 |
| ILMN_1664828 | APOBEC3H | NM_181773.2 | 0.008019 | 1.149546 |
| ILMN_1735827 | NISCH | NM_007184.3 | 0.00803 | 1.848072 |
| ILMN_2072296 | CKS2 | NM_001827.1 | 0.008106 | 0.875387 |
| ILMN_1683905 | C19orf21 | NM_173481.2 | 0.008128 | 0.674629 |
| ILMN_1813206 | CP | NM_000096.2 | 0.008182 | 1.139449 |
| ILMN_1774742 | MTTP | NM_000253.2 | 0.008191 | 0.851238 |
| ILMN_1745108 | ADAD2 | NM_139174.2 | 0.008272 | 0.79017 |
| ILMN_1805404 | GRIN1 | NM_021569.2 | 0.008324 | 0.825892 |
| ILMN_2341006 | SCARF2 | NM_153334.3 | 0.008346 | 1.146775 |
| ILMN_1711766 | SKP1A | NM_006930.2 | 0.008391 | 1.167702 |
| ILMN_1773080 | OAZ1 | NM_004152.2 | 0.008426 | 0.115385 |
| ILMN_1673069 | DPP9 | NM_139159.3 | 0.008544 | 0.866548 |
| ILMN_2362368 | U2AF1 | NM_001025203.1 | 0.008629 | 0.733454 |
| ILMN_1769092 | FAM176B | NM_018166.1 | 0.008661 | 1.123628 |
| ILMN_1724754 | MPP3 | NM_003562.1 | 0.008709 | 0.782568 |
| ILMN_1750981 | SLC25A26 | NM_173471.2 | 0.008735 | 0.826359 |
| ILMN_2160005 | NUMA1 | NM_006185.2 | 0.008776 | 1.173853 |
| ILMN_1654324 | HEYL | NM_014571.3 | 0.008779 | 1.439102 |
| ILMN_1759184 | C19orf48 | NM_199250.1 | 0.008783 | 0.491992 |
| ILMN_1815556 | PRAP1 | NM_145202.3 | 0.008801 | 0.865457 |
| ILMN_2112417 | PGAM1 | NM_002629.2 | 0.008809 | 0.739931 |
| ILMN_1718265 | ATG5 | NM_004849.2 | 0.008841 | 0.647927 |
| ILMN_1697812 | HLXB9 | NM_005515.3 | 0.008859 | 0.80677 |
| ILMN_1720300 | PRR5 | NM_181333.2 | 0.008942 | 0.699181 |
| ILMN_1806432 | NT5C | NM_014595.1 | 0.009019 | 0.523857 |
| ILMN_1736154 | ProSAPiP1 | NM_014731.2 | 0.009019 | 1.138612 |
| ILMN_1726786 | TNRC6B | NM_015088.2 | 0.009044 | 1.146365 |
| ILMN_1682226 | CLDN15 | NM_014343.1 | 0.009051 | 0.861745 |
| ILMN_2242900 | IL1RL1 | NM_173459.1 | 0.00916 | 0.809737 |
| ILMN_2343618 | SAMD3 | NM_152552.2 | 0.009198 | 1.149687 |
| ILMN_1707513 | PGPEP1 | NM_017712.2 | 0.00923 | 0.804627 |
| ILMN_1734766 | C6orf182 | NM_173830.4 | 0.009234 | 0.701394 |
| ILMN_1702363 | SULF1 | NM_015170.1 | 0.009314 | 1.180017 |
| ILMN_1693250 | ACBD5 | NM_145698.2 | 0.009316 | 0.728409 |
| ILMN_2322375 | MAFF | NM_152878.1 | 0.009335 | 0.724285 |
| ILMN_1720114 | GMNN | NM_015895.3 | 0.009355 | 0.791881 |
| ILMN_1753789 | TNN | NM_022093.1 | 0.009396 | 1.141063 |
| ILMN_2108493 | TMEM1208 | NM_001080825.2 | 0.009404 | 1.167851 |
| ILMN_1735594 | CDC42SE2 | NM_020240.2 | 0.009429 | 0.764487 |
| ILMN_2351230 | RUFY3 | NM_014961.2 | 0.009442 | 1.169369 |
| ILMN_1662438 | SOD1 | NM_000454.4 | 0.009447 | 0.504471 |
| ILMN_2116556 | LSM5 | NM_012322.1 | 0.00949 | 0.66213 |
| ILMN_1787691 | CITED4 | NM_133467.2 | 0.009495 | 1.144128 |
| ILMN_1706579 | SHBG | NM_001040.2 | 0.009582 | 0.841448 |
| ILMN_2388517 | MTERFD3 | NM_001033050.1 | 0.009691 | 0.664478 |
| ILMN_1800590 | BBS1 | NM_024649.4 | 0.009711 | 1.143601 |
| ILMN_1709044 | TGIF2 | NM_021809.5 | 0.009722 | 0.750476 |
| ILMN_1803956 | BOC | NM_033254.2 | 0.009754 | 1.22073 |
| ILMN_1730734 | TMEM205 | NM_198536.1 | 0.00978 | 0.379033 |

TABLE 2-continued

| PROBE_ID (Illumina) | SYMBOL | Accession number | pvalue | Hazard ratio |
|---|---|---|---|---|
| ILMN_2330787 | FRMD6 | NM_152330.3 | 0.009801 | 1.243165 |
| ILMN_1661875 | ANK3 | NM_001149.2 | 0.009868 | 0.814233 |
| ILMN_1748077 | DDX59 | NM_001031725.3 | 0.009902 | 1.232856 |
| ILMN_2343036 | ZMYM5 | NM_001039650.1 | 0.009915 | 1.154223 |
| ILMN_2388669 | GRIA3 | NM_181894.1 | 0.00994 | 0.778696 |
| ILMN_1748283 | PIM2 | NM_006875.2 | 0.009978 | 0.830243 |

TABLE 3

| PROBE_ID | SYMBOL | Accession number | pvalue | hazard |
|---|---|---|---|---|
| ILMN_1736078 | THBS4 | NM_003248.3 | 1.38572E-06 | 1.682498015 |
| ILMN_1713561 | C20orf103 | NM_012261.2 | 2.55588E-06 | 1.478694678 |
| ILMN_1776490 | C17orf53 | NM_024032.2 | 6.03826E-06 | 0.34241099 |
| ILMN_1755318 | HIST1H2AJ | NM_021066.2 | 1.2522E-05 | 0.470375569 |
| ILMN_1769168 | ARL10 | NM_173664.4 | 1.4066E-05 | 1.561604462 |
| ILMN_2180606 | NAT13 | NM_025146.1 | 1.73444E-05 | 0.33114386 |
| ILMN_1726815 | HIST1H3G | NM_003534.2 | 2.23113E-05 | 0.599169194 |
| ILMN_1663786 | EPB41 | NM_203342.1 | 5.97621E-05 | 0.488778032 |
| ILMN_1789955 | PNRC1 | NM_006813.1 | 7.41079E-05 | 1.448627279 |
| ILMN_1762003 | SEC62 | NM_003262.3 | 8.06626E-05 | 0.374133795 |
| ILMN_1757060 | CAMK2D | NM_172115.1 | 8.99236E-05 | 0.276235186 |
| ILMN_1721127 | HIST1H3D | NM_003530.3 | 0.000100991 | 0.360536141 |
| ILMN_2390544 | DKFZP564J102 | NM_015398.2 | 0.000123879 | 1.538277475 |
| ILMN_2249018 | LOC389816 | NM_001013653.1 | 0.000139453 | 0.427195449 |
| ILMN_1694877 | CASP6 | NM_001226.3 | 0.000139804 | 0.325712607 |
| ILMN_2103685 | DEPDC1B | NM_018369.1 | 0.00014085 | 0.366505298 |
| ILMN_1694472 | GCK | NM_033508.1 | 0.000145382 | 1.428117308 |
| ILMN_1769207 | KCTD7 | NM_153033.1 | 0.000190952 | 1.585238708 |
| ILMN_1738116 | TMEM119 | NM_181724.1 | 0.000198141 | 1.489761712 |
| ILMN_1725314 | GBP3 | NM_018284.2 | 0.000198903 | 0.361133685 |
| ILMN_1784871 | FASN | NM_004104.4 | 0.000207395 | 0.056877471 |
| ILMN_1652716 | THEX1 | NM_153332.2 | 0.000207846 | 0.288484984 |
| ILMN_2050761 | EIF4E | NM_001968.2 | 0.00025774 | 0.385622247 |
| ILMN_1747911 | CDC2 | NM_001786.2 | 0.000263771 | 0.568007158 |
| ILMN_1795340 | TMPO | NM_001032283.1 | 0.000264185 | 0.26979899 |
| ILMN_1780769 | TUBB2C | NM_006088.5 | 0.00027646 | 0.339197541 |
| ILMN_2318430 | EIF5 | NM_001969.3 | 0.000283832 | 0.321862089 |
| ILMN_2051373 | NEK2 | NM_002497.2 | 0.000305397 | 0.631359834 |
| ILMN_1736176 | PLK1 | NM_005030.3 | 0.000307467 | 0.515204021 |
| ILMN_1742238 | SET | NM_003011.2 | 0.000327498 | 0.403070785 |
| ILMN_2159044 | PDF | NM_022341.1 | 0.000327825 | 0.457651002 |
| ILMN_1678669 | RRM2 | NM_001034.1 | 0.000346452 | 0.717686042 |
| ILMN_1721963 | MEN1 | NM_130801.1 | 0.000353953 | 0.671478274 |
| ILMN_1701331 | UBE2M | NM_003969.3 | 0.000388326 | 0.036042361 |
| ILMN_1797693 | BRI3BP | NM_080626.5 | 0.000397118 | 0.239964969 |
| ILMN_2375386 | RNPS1 | NM_080594.1 | 0.000413055 | 0.225058918 |
| ILMN_2390974 | DNAJB2 | NM_006736.5 | 0.00042772 | 11.00703115 |
| ILMN_1727709 | GPBAR1 | NM_170699.2 | 0.00045926 | 1.658706421 |
| ILMN_1792110 | C10orf76 | NM_024541.2 | 0.000466902 | 1.369140571 |
| ILMN_2041327 | MRPL37 | NM_016491.2 | 0.000469554 | 0.053735215 |
| ILMN_1680419 | ASB7 | NM_024708.2 | 0.000480501 | 0.417937044 |
| ILMN_1684873 | ARSD | NM_001669.2 | 0.000494954 | 1.491248628 |
| ILMN_2414399 | NME1 | NM_000269.2 | 0.000513696 | 0.635435354 |
| ILMN_1729368 | FZD8 | NM_031866.1 | 0.000538803 | 1.491192988 |
| ILMN_2354269 | FAM164C | NM_024643.2 | 0.000560341 | 0.580400914 |
| ILMN_2220187 | GFPT1 | NM_002056.1 | 0.000563592 | 0.444796775 |
| ILMN_1693669 | WDR79 | NM_018081.1 | 0.000579389 | 0.432824705 |
| ILMN_2155998 | PSMD6 | NM_014814.1 | 0.000581349 | 0.42069481 |
| ILMN_2116556 | LSM5 | NM_012322.1 | 0.00059526 | 0.244672115 |
| ILMN_1695079 | ZNF101 | NM_033204.2 | 0.000608109 | 0.497757641 |
| ILMN_1661424 | THAP6 | NM_144721.4 | 0.000613204 | 0.505963223 |
| ILMN_1705861 | AP1M2 | NM_005498.3 | 0.000620207 | 0.487707134 |
| ILMN_1788489 | HIST1H3F | NM_021018.2 | 0.000652917 | 0.536377137 |
| ILMN_1740842 | SALL2 | NM_005407.1 | 0.000652976 | 1.634825796 |
| ILMN_1677794 | BRCA2 | NM_000059.3 | 0.000653428 | 0.521624269 |
| ILMN_1712755 | LRRC41 | NM_006369.4 | 0.000655598 | 0.254806566 |
| ILMN_1765532 | RDBP | NM_002904.5 | 0.000661777 | 0.226006062 |
| ILMN_1655734 | BXDC5 | NM_025065.6 | 0.000691174 | 0.321806825 |
| ILMN_1665515 | MGC4677 | NR_024204.1 | 0.000696851 | 0.379310859 |
| ILMN_1652280 | FBXO32 | NM_058229.2 | 0.000697182 | 4.158410279 |
| ILMN_1758067 | RGS4 | NM_005613.3 | 0.000731812 | 1.448721169 |
| ILMN_1677636 | COMP | NM_000095.2 | 0.000731916 | 1.358640294 |
| ILMN_2148796 | MND1 | NM_032117.2 | 0.000846675 | 0.525138393 |
| ILMN_1804090 | SLC25A10 | NM_012140.3 | 0.000856602 | 0.410793488 |

TABLE 3-continued

| PROBE_ID | SYMBOL | Accession number | pvalue | hazard |
|---|---|---|---|---|
| ILMN_2358914 | SLC35C2 | NM_015945.10 | 0.000884827 | 0.309429971 |
| ILMN_1771385 | GBP4 | NM_052941.3 | 0.000892961 | 0.535961124 |
| ILMN_1780667 | WDR51A | NM_015426.3 | 0.000908419 | 0.509178934 |
| ILMN_1710752 | NAPRT1 | NM_145201.3 | 0.000910567 | 0.122773656 |
| ILMN_1774589 | IQCC | NM_018134.1 | 0.000939997 | 0.39966678 |
| ILMN_1732158 | FMO2 | NM_001460.2 | 0.000962173 | 1.34318011 |
| ILMN_1735453 | FAM98A | NM_015475.3 | 0.000981164 | 0.237917743 |
| ILMN_2265759 | SLC2A11 | NM_030807.2 | 0.001008065 | 1.348676454 |
| ILMN_2190292 | UGT8 | NM_003360.2 | 0.001008405 | 0.335985912 |
| ILMN_2258471 | SLC30A5 | NM_022902.2 | 0.001009148 | 0.353367403 |
| ILMN_1801205 | GPNMB | NM_001005340.1 | 0.001012932 | 1.569348784 |
| ILMN_2224990 | HIST1H4J | NM_021968.3 | 0.001040369 | 0.433804745 |
| ILMN_2396875 | IGFBP3 | NM_000598.4 | 0.001056099 | 1.496136094 |
| ILMN_2079004 | MDH2 | NM_005918.2 | 0.001059324 | 0.098117309 |
| ILMN_2103480 | ZNF320 | NM_207333.2 | 0.001120173 | 0.515683347 |
| ILMN_1756849 | HIST1H2AE | NM_021052.2 | 0.001128782 | 0.55825351 |
| ILMN_1751264 | CCDC126 | NM_138771.3 | 0.001131162 | 0.539458225 |
| ILMN_1670638 | PITPNC1 | NM_181671.1 | 0.001156364 | 1.432837149 |
| ILMN_1805404 | GRIN1 | NM_021569.2 | 0.001179724 | 0.646993195 |
| ILMN_1735108 | ANKS6 | NM_173551.3 | 0.001190605 | 0.531136784 |
| ILMN_1710428 | CDC2 | NM_001786.2 | 0.00120549 | 0.30663512 |
| ILMN_1674620 | SGCE | NM_001099400.1 | 0.001211609 | 1.454072287 |
| ILMN_1694400 | MSR1 | NM_138715.2 | 0.001211833 | 1.467532171 |
| ILMN_2088847 | OTUD5 | NM_017602.2 | 0.00121411 | 0.378973971 |
| ILMN_2160209 | TACSTD1 | NM_002354.1 | 0.001214616 | 0.429796469 |
| ILMN_1803376 | AEBP2 | NM_153207.3 | 0.001233925 | 0.379590397 |
| ILMN_1685431 | DZIP1 | NM_198968.2 | 0.001245864 | 1.355178613 |
| ILMN_2287276 | FAM177A1 | NM_173607.3 | 0.001259789 | 0.515786967 |
| ILMN_2241317 | FOXK2 | NM_004514.3 | 0.001263375 | 0.633792641 |
| ILMN_1656192 | ZNF704 | NM_001033723.1 | 0.001275697 | 1.462816957 |
| ILMN_1708105 | EZH2 | NM_152998.1 | 0.001284332 | 0.53646297 |
| ILMN_1778617 | TAF9 | NM_001015891.1 | 0.001312314 | 0.437194069 |
| ILMN_1678423 | SPA17 | NM_017425.2 | 0.001322915 | 0.31024646 |
| ILMN_1735004 | C4orf43 | NM_018352.2 | 0.001330807 | 0.451219666 |
| ILMN_1766264 | PI16 | NM_153370.2 | 0.001342722 | 1.54312461 |
| ILMN_1651429 | SELM | NM_080430.2 | 0.001350332 | 7.120826545 |
| ILMN_1652198 | CCM2 | NM_001029835.1 | 0.001360123 | 1.478634628 |
| ILMN_1651872 | UBIAD1 | NM_013319.1 | 0.001363479 | 0.483856217 |
| ILMN_1747353 | KIF27 | NM_017576.1 | 0.001366794 | 0.305754215 |
| ILMN_1735958 | METTL2B | NM_018396.2 | 0.001372067 | 0.497518932 |
| ILMN_2130441 | HLA-H | U60319.1 | 0.001383524 | 1.309869151 |
| ILMN_2320250 | NOL6 | NM_022917.4 | 0.001386545 | 0.198070845 |
| ILMN_1710170 | PPAP2C | NM_177526.1 | 0.001395701 | 0.643357078 |
| ILMN_1719870 | GCUD2 | NM_207418.2 | 0.001456501 | 0.604998995 |
| ILMN_2181060 | CKAP2 | NM_001098525.1 | 0.001459646 | 0.663378155 |
| ILMN_1669928 | ARHGEF16 | NM_014448.2 | 0.001462437 | 0.435748845 |
| ILMN_2233099 | SSRP1 | NM_003146.2 | 0.001462983 | 0.313100651 |
| ILMN_1788886 | TOX | NM_014729.2 | 0.001464337 | 1.382074069 |
| ILMN_2150894 | ALDH1B1 | NM_000692.3 | 0.001471083 | 0.478898918 |
| ILMN_2148469 | RASL11B | NM_023940.2 | 0.001485489 | 1.301724101 |
| ILMN_1734766 | C6orf182 | NM_173830.4 | 0.001504844 | 0.352005589 |
| ILMN_1811790 | FOXS1 | NM_004118.3 | 0.001525515 | 1.493899582 |
| ILMN_1711543 | C14orf169 | NM_024644.2 | 0.001566629 | 0.378006897 |
| ILMN_1660698 | GTPBP8 | NM_014170.2 | 0.001588061 | 0.40836939 |
| ILMN_1721868 | KPNA2 | NM_002266.2 | 0.001617872 | 0.566719073 |
| ILMN_2344971 | FOXM1 | NM_202003.1 | 0.001627322 | 0.668830609 |
| ILMN_2120340 | RUVBL2 | NM_006666.1 | 0.001643506 | 0.641655709 |
| ILMN_1738938 | TIMM8B | NM_012459.1 | 0.001649996 | 0.507398524 |
| ILMN_1718387 | LOR | NM_000427.2 | 0.001653634 | 1.304994604 |
| ILMN_2388517 | MTERFD3 | NM_001033050.1 | 0.001661168 | 0.298295273 |
| ILMN_1795063 | ZADH2 | NM_175907.3 | 0.001673092 | 1.385143264 |
| ILMN_1695579 | CIT | NM_007174.1 | 0.001678569 | 0.631478718 |
| ILMN_1767448 | LHFP | NM_005780.2 | 0.001686324 | 1.649522164 |
| ILMN_1712803 | CCNB1 | NM_031966.2 | 0.001729899 | 0.698597294 |
| ILMN_1715583 | BOP1 | NM_015201.3 | 0.001745263 | 0.427680383 |
| ILMN_1685343 | NUPL1 | NM_001008565.1 | 0.001752276 | 0.531577742 |
| ILMN_1790781 | DHRS13 | NM_144683.3 | 0.00180559 | 0.373621553 |
| ILMN_2152387 | DOCK7 | NM_033407.2 | 0.001860415 | 0.372834463 |
| ILMN_2223836 | CHORDC1 | NM_012124.1 | 0.001888776 | 0.314995736 |
| ILMN_1775925 | HIST1H2BI | NM_003525.2 | 0.00191329 | 0.215094156 |
| ILMN_2310909 | ATP2A3 | NM_174955.1 | 0.001920605 | 0.640714872 |
| ILMN_1799999 | LRRCC1 | NM_033402.3 | 0.001933642 | 0.310223122 |
| ILMN_1765258 | HLA-E | NM_005516.4 | 0.001962169 | 0.41448045 |
| ILMN_1693604 | GRM2 | NM_000839.2 | 0.001964674 | 0.605639742 |
| ILMN_2396020 | DUSP6 | NM_001946.2 | 0.001989538 | 0.440365228 |
| ILMN_2215370 | WWP1 | NM_007013.3 | 0.002004931 | 0.410021251 |
| ILMN_1732127 | RBKS | NM_022128.1 | 0.002028283 | 0.519499482 |
| ILMN_1709451 | TFPT | NM_013342.2 | 0.00203197 | 2.444929835 |

TABLE 3-continued

| PROBE_ID | SYMBOL | Accession number | pvalue | hazard |
| --- | --- | --- | --- | --- |
| ILMN_1753467 | SAMD4B | NM_018028.2 | 0.002084896 | 1.944528201 |
| ILMN_1797893 | PFAAP5 | NM_014887.1 | 0.002089509 | 1.780690735 |
| ILMN_2413898 | MCM10 | NM_018518.3 | 0.002098445 | 0.746035804 |
| ILMN_1689086 | CTSC | NM_001814.2 | 0.002101771 | 0.357197864 |
| ILMN_2363668 | YIF1B | NM_001039673.1 | 0.002144846 | 0.395212683 |
| ILMN_1737195 | CENPK | NM_022145.3 | 0.002181123 | 0.652279 |
| ILMN_1749789 | HIST1H1D | NM_005320.2 | 0.002196903 | 0.45086036 |
| ILMN_1760153 | GATA5 | NM_080473.3 | 0.00224015 | 1.333301072 |
| ILMN_2369018 | EVI2A | NM_014210.2 | 0.002248908 | 1.53070581 |
| ILMN_2294653 | PDE5A | NM_033437.2 | 0.00226466 | 1.325372841 |
| ILMN_1742307 | MEST | NM_177524.1 | 0.002265982 | 0.384915559 |
| ILMN_2207865 | HIST1H3I | NM_003533.2 | 0.002313157 | 0.390719052 |
| ILMN_2061043 | CD48 | NM_001778.2 | 0.002343934 | 1.4403949 |
| ILMN_2307656 | AGTRAP | NM_001040196.1 | 0.002353483 | 0.476416601 |
| ILMN_1737709 | RPL10L | NM_080746.2 | 0.002355167 | 0.592421921 |
| ILMN_1777156 | GTPBP3 | NM_032620.1 | 0.002378577 | 0.458656308 |
| ILMN_2058141 | HMGN2 | NM_005517.3 | 0.00240793 | 0.396669549 |
| ILMN_1700413 | MAFF | NM_152878.1 | 0.002420337 | 0.473434773 |
| ILMN_1688755 | AAK1 | NM_014911.2 | 0.0024249 | 1.443142271 |
| ILMN_1656415 | CDKN2C | NM_078626.2 | 0.002445334 | 1.363082198 |
| ILMN_1773080 | OAZ1 | NM_004152.2 | 0.002463203 | 0.006652434 |
| ILMN_1655052 | TRNT1 | NM_016000.2 | 0.002469548 | 0.453240253 |
| ILMN_1763491 | CKMT1B | NM_020990.3 | 0.002479888 | 0.696617712 |
| ILMN_2349459 | BIRC5 | NM_001012271.1 | 0.002493781 | 0.632059133 |
| ILMN_1693597 | ZNF287 | NM_020653.1 | 0.002546359 | 1.321302822 |
| ILMN_1791149 | ARL6IP4 | NM_001002252.1 | 0.002559255 | 0.445204912 |
| ILMN_2191634 | RPL37 | NM_000997.3 | 0.002566623 | 0.439638182 |
| ILMN_1692511 | TMEM106C | NM_024056.2 | 0.002584001 | 0.410086273 |
| ILMN_2336335 | 40245 | NM_006231.2 | 0.002594922 | 1.492701021 |
| ILMN_1670903 | NAT2 | NM_000015.2 | 0.002621283 | 0.394117706 |
| ILMN_2350183 | ST5 | NM_213618.1 | 0.00264123 | 1.71088169 |
| ILMN_1806473 | BEX5 | NM_001012978.2 | 0.00264497 | 1.405290668 |
| ILMN_1745108 | ADAD2 | NM_139174.2 | 0.002650355 | 0.564020967 |
| ILMN_2208455 | DDHD1 | NM_030637.1 | 0.002666187 | 0.62040113 |
| ILMN_2289381 | DKK3 | NM_015881.5 | 0.002677686 | 1.273699695 |
| ILMN_2093500 | ZBED5 | NM_021211.2 | 0.002686929 | 1.593462221 |
| ILMN_1676215 | DLG2 | NM_001364.2 | 0.002687616 | 1.393751447 |
| ILMN_1746435 | HIST1H1E | NM_005321.2 | 0.002709568 | 0.426535974 |
| ILMN_1681757 | FAM80B | NM_020734.1 | 0.002716862 | 1.385585016 |
| ILMN_1814282 | ISG20L1 | NM_022767.2 | 0.002720111 | 0.401067743 |
| ILMN_1695107 | IL20RA | NM_014432.2 | 0.002727132 | 0.391212161 |
| ILMN_1704261 | RANGRF | NM_016492.3 | 0.002732176 | 0.561395184 |
| ILMN_1742544 | MEF2C | NM_002397.2 | 0.002763958 | 1.634742949 |
| ILMN_1800420 | RNF214 | NM_207343.2 | 0.002818409 | 0.441702219 |
| ILMN_2115696 | USP42 | NM_032172.2 | 0.002826683 | 1.254016918 |
| ILMN_2369104 | TRAPPC6B | NM_177452.3 | 0.002836961 | 0.537255223 |
| ILMN_1811426 | TMTC1 | NM_175861.2 | 0.002846937 | 1.449228612 |
| ILMN_1679641 | FAM120B | NM_032448.1 | 0.00286719 | 0.700685077 |
| ILMN_2191436 | POLA1 | NM_016937.3 | 0.002880446 | 0.291792953 |
| ILMN_1708160 | KPNA2 | NM_002266.2 | 0.002920159 | 0.671481421 |
| ILMN_1752249 | FAM38A | NM_014745.1 | 0.002968991 | 5.849847658 |
| ILMN_2414027 | CKLF | NM_001040138.1 | 0.003007182 | 0.536219708 |
| ILMN_1748147 | MTO1 | NM_133645.1 | 0.003021874 | 0.435348875 |
| ILMN_1688231 | TREM1 | NM_018643.2 | 0.003038524 | 0.404373704 |
| ILMN_2071826 | RNF152 | NM_173557.1 | 0.003053367 | 1.396524052 |
| ILMN_1720542 | POLR2I | NM_006233.4 | 0.00316402 | 0.710946957 |
| ILMN_1718334 | ITPA | NM_033453.2 | 0.003165015 | 0.441320307 |
| ILMN_1731374 | CPE | NM_001873.1 | 0.003168171 | 1.387565375 |
| ILMN_2099045 | KIAA1524 | NM_020890.1 | 0.003184317 | 0.397921546 |
| ILMN_1774350 | MYOZ3 | NM_133371.2 | 0.003202754 | 1.362439801 |
| ILMN_2395926 | MANBAL | NM_022077.3 | 0.003220826 | 0.446106468 |
| ILMN_1814002 | TEAD3 | NM_003214.3 | 0.00322364 | 0.508063459 |
| ILMN_2351916 | EXO1 | NM_006027.3 | 0.00323852 | 0.621409496 |
| ILMN_1785005 | NCF4 | NM_013416.2 | 0.003244984 | 1.852600594 |
| ILMN_2082810 | BRD7 | NM_013263.2 | 0.003247679 | 0.445190505 |
| ILMN_1702858 | ADHFE1 | NM_144650.2 | 0.003259448 | 1.522440502 |
| ILMN_1815385 | SMAD9 | NM_005905.3 | 0.003266862 | 1.486381567 |
| ILMN_1699665 | CLIC6 | NM_053277.1 | 0.003268017 | 1.394934339 |
| ILMN_1672660 | MBP | NM_001025100.1 | 0.003308632 | 1.307617077 |
| ILMN_1710495 | PAPLN | NM_173462.3 | 0.003317357 | 1.555971585 |
| ILMN_1788955 | PDLIM1 | NM_020992.2 | 0.003335768 | 0.36434918 |
| ILMN_1750130 | GSPT1 | NM_002094.2 | 0.003432206 | 0.561549921 |
| ILMN_1715175 | MET | NM_000245.2 | 0.00344409 | 0.408579482 |
| ILMN_1688041 | TMEM53 | NM_024587.2 | 0.003458129 | 0.460287691 |
| ILMN_1693333 | TMEM19 | NM_018279.3 | 0.003507351 | 0.36821929 |
| ILMN_1688848 | TMEM44 | NM_138399.3 | 0.003510688 | 0.444391423 |
| ILMN_2379527 | ELMO1 | NM_014800.9 | 0.003566733 | 1.44357207 |
| ILMN_1729713 | RAB23 | NM_183227.1 | 0.003569889 | 1.290055449 |

TABLE 3-continued

| PROBE_ID | SYMBOL | Accession number | pvalue | hazard |
|---|---|---|---|---|
| ILMN_1717262 | PROCR | NM_006404.3 | 0.003588508 | 0.481142471 |
| ILMN_1722829 | HLF | NM_002126.4 | 0.003592205 | 1.387440105 |
| ILMN_1653165 | AAMP | NM_001087.3 | 0.003625108 | 0.51315174 |
| ILMN_1652826 | LRRC17 | NM_005824.1 | 0.0036285 | 1.338749637 |
| ILMN_1653200 | SLC22A17 | NM_020372.2 | 0.003656112 | 1.452161875 |
| ILMN_2076250 | GPBP1L1 | NM_021639.3 | 0.003660253 | 0.525101894 |
| ILMN_1731610 | ABLIM1 | NM_006720.3 | 0.00367075 | 1.420084637 |
| ILMN_1653001 | CABLES1 | NM_138375.1 | 0.003735355 | 0.421734171 |
| ILMN_1670609 | ATOX1 | NM_004045.3 | 0.003736891 | 4.196917472 |
| ILMN_1714197 | ACSS2 | NM_139274.1 | 0.003759326 | 0.144997669 |
| ILMN_2367070 | ACOT9 | NM_001033583.2 | 0.003773424 | 0.439029956 |
| ILMN_1757406 | HIST1H1C | NM_005319.3 | 0.00377794 | 0.545763401 |
| ILMN_1815010 | RNF141 | NM_016422.3 | 0.003799608 | 0.499957309 |
| ILMN_1687589 | CPT1A | NM_001876.2 | 0.003816375 | 0.556334372 |
| ILMN_1702265 | HDHD2 | NM_032124.4 | 0.003820466 | 0.255780221 |
| ILMN_1776577 | DSCC1 | NM_024094.2 | 0.003827106 | 0.445375329 |
| ILMN_1680692 | NUCKS1 | NM_022731.2 | 0.003830411 | 0.352050942 |
| ILMN_2301083 | UBE2C | NM_181803.1 | 0.00384705 | 0.746466822 |
| ILMN_1660636 | WWOX | NM_130844.1 | 0.003850247 | 0.389587873 |
| ILMN_2252408 | CNPY4 | NM_152755.1 | 0.003872081 | 1.926411669 |
| ILMN_2122374 | FAM49B | NM_016623.3 | 0.003874185 | 0.475549021 |
| ILMN_1679809 | GSTP1 | NM_000852.2 | 0.00390375 | 12.13414752 |
| ILMN_1739645 | ANLN | NM_018685.2 | 0.003925781 | 0.565399848 |
| ILMN_1804419 | LRMP | NM_006152.2 | 0.003992031 | 1.293737566 |
| ILMN_2330410 | EIF3C | NM_003752.3 | 0.004011169 | 0.321444331 |
| ILMN_1696380 | GHRL | NM_016362.2 | 0.004018356 | 1.26994829 |
| ILMN_1787280 | C1orf135 | NM_024037.1 | 0.004058179 | 0.650335614 |
| ILMN_1736178 | AEBP1 | NM_001129.3 | 0.004064418 | 2.22040315 |
| ILMN_1801939 | CCNB2 | NM_004701.2 | 0.004065318 | 0.738524159 |
| ILMN_1682375 | ATPBD3 | NM_145232.2 | 0.004071346 | 0.47285411 |
| ILMN_1657701 | TMEM137 | XR_017971.1 | 0.004078655 | 0.178899275 |
| ILMN_1662419 | COX7A1 | NM_001864.2 | 0.004102612 | 1.701574095 |
| ILMN_1708041 | PLEKHF1 | NM_024310.4 | 0.004131276 | 1.32143517 |
| ILMN_1667641 | ACACA | NM_198834.1 | 0.004154722 | 1.323720243 |
| ILMN_1682675 | TWF1 | NM_002822.3 | 0.004217274 | 0.474590351 |
| ILMN_2123402 | TMEM4 | NM_014255.4 | 0.004223593 | 0.426349629 |
| ILMN_1720484 | CRTAP | NM_006371.3 | 0.004250147 | 1.390315752 |
| ILMN_1756982 | CLIC1 | NM_001288.4 | 0.004251433 | 0.262265066 |
| ILMN_2315964 | PSRC1 | NM_001032290.1 | 0.004265342 | 0.446786367 |
| ILMN_1738704 | TRIM26 | NM_003449.3 | 0.004269347 | 0.598757026 |
| ILMN_1713178 | FAM116A | XM_001132771.1 | 0.004275545 | 0.563919761 |
| ILMN_1814856 | C9orf7 | NM_017586.1 | 0.004277418 | 0.424020863 |
| ILMN_1755504 | CALCOCO2 | NM_005831.3 | 0.004300376 | 1.498460692 |
| ILMN_1764694 | ZFP14 | NM_020917.1 | 0.004300529 | 1.492032427 |
| ILMN_1718265 | ATG5 | NM_004849.2 | 0.004309361 | 0.314797866 |
| ILMN_1764850 | HPCAL1 | NM_134421.1 | 0.004323109 | 0.564769594 |
| ILMN_1677652 | PREX2 | NM_024870.2 | 0.004337807 | 1.291465793 |
| ILMN_2362293 | FBXO38 | NM_205836.1 | 0.004344345 | 0.30957276 |
| ILMN_2184231 | CHRDL1 | NM_145234.2 | 0.004355928 | 1.405989697 |
| ILMN_1674337 | FKBP2 | NM_057092.1 | 0.004365515 | 0.552251971 |
| ILMN_1673380 | GNG12 | NM_018841.4 | 0.004429613 | 2.220091452 |
| ILMN_1730347 | CCDC115 | NM_032357.2 | 0.004442253 | 1.299753115 |
| ILMN_1752589 | TMEM183A | NM_138391.4 | 0.004454617 | 0.582347893 |
| ILMN_1692790 | ITGB3BP | NM_014288.3 | 0.004456606 | 0.283335019 |
| ILMN_1680626 | PDIA6 | NM_005742.2 | 0.004486813 | 0.438758243 |
| ILMN_1789040 | SLITRK5 | NM_015567.1 | 0.004487421 | 1.58800473 |
| ILMN_2221046 | GM2A | NM_000405.3 | 0.004499557 | 1.343681008 |
| ILMN_2392818 | RTKN | NM_033046.2 | 0.004504209 | 0.380099265 |
| ILMN_1691559 | ELF2 | NM_006874.2 | 0.004539554 | 1.445911237 |
| ILMN_2120965 | NPAT | NM_002519.1 | 0.004608556 | 1.53213071 |
| ILMN_1761772 | NUP155 | NM_153485.1 | 0.004609259 | 0.787766929 |
| ILMN_1768969 | LBR | NM_194442.1 | 0.004612078 | 0.381969617 |
| ILMN_1669931 | TM9SF3 | NM_020123.2 | 0.004639769 | 0.455109316 |
| ILMN_1731194 | STRAP | NM_007178.3 | 0.004663374 | 0.486661013 |
| ILMN_1665717 | EIF2S3 | NM_001415.3 | 0.00466426 | 0.607788466 |
| ILMN_2076567 | UBE2V2 | NM_003350.2 | 0.004673328 | 0.376889407 |
| ILMN_1815570 | HOXA6 | NM_024014.2 | 0.004677877 | 1.315082473 |
| ILMN_1704943 | ATPBD1C | NM_016301.2 | 0.004692424 | 0.45831831 |
| ILMN_1681304 | PAN3 | NM_175854.5 | 0.004694593 | 0.336691298 |
| ILMN_1754842 | DLGAP4 | NM_014902.3 | 0.004695897 | 1.500771594 |
| ILMN_2397347 | SEMG1 | NM_198139.1 | 0.004704468 | 0.504369353 |
| ILMN_1766983 | FBXW11 | NM_033644.2 | 0.004733209 | 1.373759174 |
| ILMN_1715607 | CHMP4A | NM_014169.2 | 0.004813934 | 0.599264497 |
| ILMN_1657148 | C19orf23 | NM_152480.1 | 0.004839756 | 0.777157317 |
| ILMN_1749213 | SDF2L1 | NM_022044.2 | 0.004874196 | 0.117041269 |
| ILMN_1664761 | TMEM138 | NM_016464.3 | 0.004884175 | 1.768386882 |
| ILMN_1782403 | PRR11 | NM_018304.2 | 0.004895172 | 0.692001418 |
| ILMN_1749583 | KIAA1285 | NM_015694.2 | 0.004895535 | 0.485704875 |

TABLE 3-continued

| PROBE_ID | SYMBOL | Accession number | pvalue | hazard |
|---|---|---|---|---|
| ILMN_2294274 | S100PBP | NM_022753.2 | 0.004902704 | 0.348252651 |
| ILMN_2089977 | FKBP9L | NM_182827.1 | 0.004925827 | 1.35715531 |
| ILMN_1708143 | FAM127A | NM_001078171.1 | 0.004940424 | 1.536857038 |
| ILMN_1687947 | HIST1H2BE | NM_003523.2 | 0.004945146 | 0.60890965 |
| ILMN_1790741 | RNF126 | NM_194460.1 | 0.004999963 | 0.403652191 |
| ILMN_2084391 | RAD18 | NM_020165.2 | 0.005021514 | 0.478869988 |
| ILMN_1700975 | ENSA | NM_207168.1 | 0.005023952 | 0.597039464 |
| ILMN_1758529 | P2RX1 | NM_002558.2 | 0.005040437 | 1.331690952 |
| ILMN_1653824 | LAMC2 | NM_018891.1 | 0.005053334 | 0.510397105 |
| ILMN_1673673 | PBK | NM_018492.2 | 0.005072448 | 0.502353808 |
| ILMN_2188451 | HIST1H2AH | NM_080596.1 | 0.005091975 | 0.56869136 |
| ILMN_1729430 | FBXO18 | NM_032807.3 | 0.005096865 | 0.409638443 |
| ILMN_2145670 | TNC | NM_002160.2 | 0.005099349 | 0.44945639 |
| ILMN_1799113 | CCDC41 | NM_016122.2 | 0.005124666 | 0.331541717 |
| ILMN_1694177 | PCNA | NM_182649.1 | 0.005131856 | 0.431824254 |
| ILMN_2365176 | ALDH8A1 | NM_022568.2 | 0.0051498 | 0.578765996 |
| ILMN_1703791 | ANXA7 | NM_004034.1 | 0.005194134 | 0.520011299 |
| ILMN_1653432 | HNRPDL | NR_003249.1 | 0.00519902 | 1.962006317 |
| ILMN_1711470 | UBE2T | NM_014176.2 | 0.005212905 | 0.70825341 |
| ILMN_1672876 | MFI2 | NM_005929.4 | 0.005216636 | 0.688790743 |
| ILMN_1803956 | BOC | NM_033254.2 | 0.005222405 | 1.56055792 |
| ILMN_1793959 | ADPGK | NM_031284.3 | 0.005222668 | 0.622209617 |
| ILMN_2141118 | C15orf59 | NM_001039614.1 | 0.005232281 | 1.288389631 |
| ILMN_1740265 | ACOT7 | NM_181864.2 | 0.005276176 | 0.42513968 |
| ILMN_1705515 | UPF3A | NM_080687.1 | 0.005335596 | 0.555924796 |
| ILMN_1747870 | CD3EAP | NM_012099.1 | 0.005335819 | 0.431594263 |
| ILMN_1662935 | C1QTNF7 | NM_031911.3 | 0.005340141 | 1.400132792 |
| ILMN_2408796 | C19orf28 | NM_174983.3 | 0.005377619 | 0.535188081 |
| ILMN_1808748 | CLCN6 | NM_001286.2 | 0.005389385 | 0.448798804 |
| ILMN_2347999 | IFNAR2 | NM_207585.1 | 0.00540236 | 0.394741019 |
| ILMN_1759184 | C19orf48 | NM_199250.1 | 0.005420614 | 0.262738545 |
| ILMN_2402392 | COL8A1 | NM_001850.3 | 0.005441026 | 1.506073801 |
| ILMN_1670542 | AK2 | NM_001625.2 | 0.005456193 | 0.4642596 |
| ILMN_1815306 | AP2A1 | NM_014203.2 | 0.005479068 | 0.45782699 |
| ILMN_1665982 | AKTIP | NM_022476.2 | 0.005552907 | 1.426606686 |
| ILMN_1754476 | TRIM15 | NM_033229.2 | 0.005599962 | 0.672365812 |
| ILMN_1715789 | DOCK1 | NM_001380.3 | 0.005637866 | 1.290809728 |
| ILMN_2140207 | ATPBD4 | NM_080650.2 | 0.005687417 | 0.465173775 |
| ILMN_1707257 | HIST1H3J | NM_003535.2 | 0.00569548 | 0.411868035 |
| ILMN_2330341 | TCEAL4 | NM_024863.4 | 0.005697718 | 1.905792982 |
| ILMN_2371964 | MRPS12 | NM_021107.1 | 0.005734333 | 0.338999466 |
| ILMN_1793888 | SERPINB5 | NM_002639.3 | 0.005756119 | 0.759749969 |
| ILMN_1715616 | PPIL5 | NM_203467.1 | 0.005771905 | 0.454389155 |
| ILMN_1702526 | C17orf48 | NM_020233.4 | 0.005799246 | 1.355222195 |
| ILMN_1739076 | HIST1H2BO | NM_003527.4 | 0.005801406 | 0.73401284 |
| ILMN_2075714 | ZNF284 | NM_001037813.2 | 0.005824027 | 1.411449642 |
| ILMN_1814151 | AGR2 | NM_006408.2 | 0.005831268 | 0.504940913 |
| ILMN_1738684 | NRXN2 | NM_138734.1 | 0.005836232 | 1.418214009 |
| ILMN_2065022 | KIAA0672 | NM_014859.4 | 0.00584505 | 1.279720801 |
| ILMN_2402168 | EXOSC10 | NM_001001998.1 | 0.005845299 | 0.518518591 |
| ILMN_1803570 | BRI3BP | NM_080626.5 | 0.00584885 | 0.795690999 |
| ILMN_2103362 | ARHGAP27 | NM_199282.1 | 0.005891206 | 0.487395295 |
| ILMN_1731048 | TLR1 | NM_003263.3 | 0.005909894 | 0.354107909 |
| ILMN_1813295 | LMO3 | NM_018640.3 | 0.00592348 | 1.417834019 |
| ILMN_1676058 | MAGOHB | NM_018048.3 | 0.005932808 | 0.466547235 |
| ILMN_2255133 | BCL11A | BCL11A | 0.005943127 | 0.464319877 |
| ILMN_2311537 | HMGA1 | NM_145902.1 | 0.005946164 | 0.801243797 |
| ILMN_1718853 | UQCRC2 | NM_003366.2 | 0.005980146 | 0.513524684 |
| ILMN_1776845 | HIST1H3A | NM_003529.2 | 0.005985544 | 0.710949575 |
| ILMN_1672122 | PH-4 | NM_177938.2 | 0.005995002 | 0.5034317 |
| ILMN_1651229 | IPO13 | NM_014652.2 | 0.006001369 | 2.321489493 |
| ILMN_2217661 | SREBF2 | NM_004599.2 | 0.006020596 | 0.42538648 |
| ILMN_2115340 | HIST2H4A | NM_003548.2 | 0.006051534 | 0.723953441 |
| ILMN_1662140 | SGPP2 | NM_152386.2 | 0.006053142 | 0.735761893 |
| ILMN_2362368 | U2AF1 | NM_001025203.1 | 0.006055125 | 0.543969023 |
| ILMN_1710070 | PCSK6 | NM_138320.1 | 0.00611501 | 0.72158868 |
| ILMN_2358783 | ASB3 | NM_016115.3 | 0.006128461 | 0.496862366 |
| ILMN_2407464 | FASTK | NM_006712.3 | 0.006201308 | 0.537689921 |
| ILMN_2382990 | HK1 | NM_033498.1 | 0.006216229 | 2.353179628 |
| ILMN_2143685 | CLDN7 | NM_001307.4 | 0.00624499 | 0.7855261 |
| ILMN_1726108 | LASS2 | NM_181746.2 | 0.006250473 | 0.422395144 |
| ILMN_1734867 | NR2C1 | NM_003297.1 | 0.006253786 | 0.575169323 |
| ILMN_1788180 | RAB13 | NM_002870.2 | 0.006265118 | 0.448550867 |
| ILMN_1720595 | MDGA1 | NM_153487.3 | 0.006287087 | 1.594869983 |
| ILMN_2162358 | ZNF597 | NM_152457.1 | 0.006307603 | 1.269525875 |
| ILMN_1717393 | PTCHD1 | NM_173495.2 | 0.006308428 | 1.365299066 |
| ILMN_1688033 | HPS5 | NM_181507.1 | 0.006328446 | 1.350346589 |
| ILMN_1664815 | ELK4 | NM_001973.2 | 0.006330513 | 0.648779128 |

TABLE 3-continued

| PROBE_ID | SYMBOL | Accession number | pvalue | hazard |
|---|---|---|---|---|
| ILMN_2388070 | TMEM44 | NM_138399.3 | 0.006349048 | 0.462595584 |
| ILMN_1666096 | ACSL3 | NM_004457.3 | 0.006367395 | 1.470484977 |
| ILMN_1717757 | CALML4 | NM_001031733.2 | 0.006395212 | 0.732505749 |
| ILMN_2116827 | RGPD1 | NM_001024457.1 | 0.006400663 | 1.273196499 |
| ILMN_1684647 | ILKAP | NM_030768.2 | 0.006420595 | 0.520137067 |
| ILMN_1795507 | ABCA6 | NM_080284.2 | 0.006465301 | 1.266389585 |
| ILMN_1726030 | GPX7 | NM_015696.3 | 0.006505417 | 1.319011509 |
| ILMN_2336595 | ACSS2 | NM_018677.2 | 0.00659276 | 0.377268086 |
| ILMN_1653251 | HIST1H1B | NM_005322.2 | 0.006533608 | 0.61504306 |
| ILMN_2250923 | FOXP1 | NM_032682.4 | 0.006544389 | 0.435456884 |
| ILMN_1694759 | C19orf42 | NM_024104.3 | 0.006574444 | 0.480847866 |
| ILMN_2230025 | PDLIM3 | NM_014476.1 | 0.006617224 | 1.749382931 |
| ILMN_1812970 | RWDD1 | NM_016104.2 | 0.006651454 | 1.274265391 |
| ILMN_1733559 | LOC100008589 | NR_003287.1 | 0.006655633 | 0.05494194 |
| ILMN_2214278 | ANKRD32 | NM_032290.2 | 0.006672263 | 0.407002498 |
| ILMN_2364928 | APBA2BP | NM_031231.3 | 0.006674687 | 0.476662735 |
| ILMN_2368721 | CENPM | NM_024053.3 | 0.006681262 | 0.775688614 |
| ILMN_2042651 | EVI2B | NM_006495.3 | 0.006709516 | 0.398923979 |
| ILMN_1757536 | USP40 | NM_018218.2 | 0.006719019 | 0.443606755 |
| ILMN_1743579 | WDR4 | NM_033661.3 | 0.006719975 | 0.586652104 |
| ILMN_1794017 | SERTAD1 | NM_013376.3 | 0.006766851 | 1.477182017 |
| ILMN_2192683 | DHX37 | NM_032656.2 | 0.006803347 | 0.144674391 |
| ILMN_2148452 | BCAS2 | NM_005872.2 | 0.00688614 | 0.394539719 |
| ILMN_1805778 | RBM12B | NM_203390.2 | 0.006906573 | 1.534168009 |
| ILMN_1658821 | SAMD1 | NM_138352.1 | 0.006914193 | 0.710097017 |
| ILMN_2072357 | IRF6 | NM_006147.2 | 0.006953237 | 0.502557868 |
| ILMN_1740508 | KCNMA1 | NM_001014797.1 | 0.006971733 | 1.4569512 |
| ILMN_2401779 | FAM102A | NM_001035254.1 | 0.007011925 | 0.251786364 |
| ILMN_2330570 | LEPR | NM_002303.3 | 0.007074066 | 1.44870954 |
| ILMN_1675106 | YIPF2 | NM_024029.3 | 0.007074451 | 0.454951256 |
| ILMN_1784367 | HSPD1 | NM_002156.4 | 0.007116294 | 0.729230188 |
| ILMN_1798254 | ACTR10 | NM_018477.2 | 0.00713915 | 0.456078802 |
| ILMN_2061950 | RABGAP1 | NM_012197.2 | 0.007143416 | 1.909688817 |
| ILMN_1657836 | PLEKHG2 | NM_022835.1 | 0.007225484 | 1.409139505 |
| ILMN_2073307 | IL10 | NM_000572.2 | 0.007235338 | 0.581576619 |
| ILMN_1669023 | FHL5 | NM_020482.3 | 0.007238126 | 1.314020057 |
| ILMN_2413251 | EWSR1 | NM_005243.2 | 0.007243401 | 0.497456343 |
| ILMN_1692779 | PRPF39 | NM_017922.2 | 0.007254878 | 0.410654488 |
| ILMN_1803338 | CCDC80 | NM_199511.1 | 0.007368666 | 1.892126506 |
| ILMN_2316918 | PANK1 | NM_148978.1 | 0.007397188 | 0.417679556 |
| ILMN_1781400 | SLC7A2 | NM_001008539.2 | 0.007413353 | 1.515745654 |
| ILMN_1799289 | MRPL55 | NM_181454.1 | 0.007420628 | 0.461570361 |
| ILMN_2410924 | PLOD2 | NM_000935.2 | 0.007437692 | 1.876219594 |
| ILMN_1684931 | GPR119 | NM_178471.1 | 0.007438219 | 0.463748761 |
| ILMN_2138589 | MERTK | NM_006343.2 | 0.007438466 | 1.473780814 |
| ILMN_1671557 | PHLDA2 | NM_003311.3 | 0.00745336 | 0.620891122 |
| ILMN_1809101 | STEAP2 | NM_152999.3 | 0.007473192 | 1.405229708 |
| ILMN_2381037 | LIMS1 | NM_004987.3 | 0.007479728 | 0.506576202 |
| ILMN_1723522 | APOLD1 | NM_030817.1 | 0.007500182 | 1.273846061 |
| ILMN_2292178 | CLEC12A | NM_201623.2 | 0.007513142 | 1.293618589 |
| ILMN_2294684 | CEP170 | NM_014812.2 | 0.007567842 | 0.492080122 |
| ILMN_2331163 | CUL4A | NM_003589.2 | 0.007580851 | 0.677020715 |
| ILMN_2209163 | CHD6 | NM_032221.3 | 0.007605645 | 0.532521441 |
| ILMN_1777263 | MEOX2 | NM_005924.4 | 0.007648662 | 1.344671457 |
| ILMN_1688666 | HIST1H2BH | NM_003524.2 | 0.007688938 | 0.679188681 |
| ILMN_2064926 | ITFG1 | NM_030790.3 | 0.007689192 | 0.430133813 |
| ILMN_1812795 | RUNX1T1 | NM_175636.1 | 0.007693535 | 1.234743018 |
| ILMN_1783908 | B3GNT9 | NM_033309.2 | 0.007740725 | 0.548726198 |
| ILMN_1689438 | BTRC | NM_033637.2 | 0.007752648 | 1.397535008 |
| ILMN_1687652 | TGFB3 | NM_003239.1 | 0.007770746 | 1.352457691 |
| ILMN_1695025 | CD2 | NM_001767.3 | 0.007797265 | 1.313736386 |
| ILMN_1749846 | OMD | NM_005014.1 | 0.007801275 | 1.462435251 |
| ILMN_1807945 | ANP32A | NM_006305.2 | 0.0078657 | 0.54232047 |
| ILMN_1664910 | RPSA | NM_001012321.1 | 0.007938497 | 0.537155609 |
| ILMN_2407605 | GIYD2 | NM_024044.2 | 0.007944606 | 0.531217639 |
| ILMN_2152095 | RNASEN | NM_013235.3 | 0.007987447 | 0.458218869 |
| ILMN_1678464 | DCLRE1C | NM_001033858.1 | 0.007991392 | 0.619351961 |
| ILMN_1730529 | CAB39L | NM_001079670.1 | 0.008004106 | 0.465761281 |
| ILMN_1809285 | DCP1A | NM_018403.4 | 0.008063544 | 0.499569903 |
| ILMN_1699440 | ZBTB47 | NM_145166.2 | 0.008069873 | 1.300721326 |
| ILMN_1774083 | TRIAP1 | NM_016399.2 | 0.008084101 | 0.452093496 |
| ILMN_1796523 | FNIP1 | NM_133372.2 | 0.008101041 | 1.251935595 |
| ILMN_1742379 | IFT122 | NM_052989.1 | 0.008107069 | 0.585299967 |
| ILMN_1798581 | MCM8 | NM_032485.4 | 0.008124758 | 0.39895875 |
| ILMN_2045994 | SEPW1 | NM_003009.2 | 0.008180544 | 2.170610772 |
| ILMN_2111237 | MN1 | NM_002430.2 | 0.008181064 | 1.480543494 |
| ILMN_1727558 | MRPL27 | NM_148571.1 | 0.008216167 | 0.49290801 |
| ILMN_1713613 | PIAS2 | NM_173206.2 | 0.008218756 | 0.533318798 |

TABLE 3-continued

| PROBE_ID | SYMBOL | Accession number | pvalue | hazard |
|---|---|---|---|---|
| ILMN_2207720 | ITM2B | NM_021999.3 | 0.008268371 | 0.409229979 |
| ILMN_1778059 | CASP4 | NM_033306.2 | 0.008299631 | 0.352535107 |
| ILMN_2151281 | GABARAPL1 | NM_031412.2 | 0.00830592 | 1.40344079 |
| ILMN_2227368 | SELT | NM_016275.3 | 0.008323563 | 0.629151938 |
| ILMN_1755222 | C9orf82 | NM_024828.2 | 0.008376736 | 0.537845874 |
| ILMN_1670272 | LRP10 | NM_014045.3 | 0.008387951 | 0.488461901 |
| ILMN_1750044 | ZNHIT3 | NM_004773.2 | 0.008414785 | 0.596203697 |
| ILMN_1801899 | PLEC1 | NM_201380.2 | 0.008415501 | 0.788422978 |
| ILMN_1667707 | SPCS3 | NM_021928.1 | 0.008416213 | 0.333306413 |
| ILMN_1784459 | MMP3 | NM_002422.3 | 0.008424899 | 0.743845984 |
| ILMN_1715613 | TAOK2 | NM_004783.2 | 0.008428815 | 0.577192898 |
| ILMN_1783170 | ING3 | NM_198267.1 | 0.008464107 | 0.45594537 |
| ILMN_2343332 | TAF9 | NM_001015891.1 | 0.008467944 | 0.502769469 |
| ILMN_1746426 | TOMM70A | NM_014820.3 | 0.008511501 | 0.451400009 |
| ILMN_1708164 | EIF3A | NM_003750.2 | 0.0085147 | 0.273046283 |
| ILMN_2319919 | MAGEA2 | NM_175743.1 | 0.008522299 | 0.564708047 |
| ILMN_1788166 | TTK | NM_003318.3 | 0.008532079 | 0.6260955 |
| ILMN_1694731 | CLCN7 | NM_001287.3 | 0.008552366 | 0.047428986 |
| ILMN_2189037 | WDR52 | NM_018338.2 | 0.008579091 | 0.442426039 |
| ILMN_1654411 | CCL18 | NM_002988.2 | 0.008582303 | 0.534771494 |
| ILMN_1666372 | ATP5H | NM_006356.2 | 0.00858678 | 0.339181294 |
| ILMN_1663220 | MRPL22 | NM_014180.2 | 0.008657699 | 0.682213605 |
| ILMN_1736689 | PC | NM_001040716.1 | 0.008686562 | 0.491364567 |
| ILMN_1702609 | B3GNT5 | NM_032047.4 | 0.008699695 | 0.35924426 |
| ILMN_2126399 | psiTPTE22 | EF535614.1 | 0.008701089 | 0.508410979 |
| ILMN_1714438 | MUTYH | NM_001048172.1 | 0.008708257 | 1.452044111 |
| ILMN_1697117 | TBP | NM_003194.3 | 0.008717257 | 1.375754246 |
| ILMN_2160476 | CCL22 | NM_002990.3 | 0.00873155 | 0.626816124 |
| ILMN_2405156 | PPAP2C | NM_177543.1 | 0.008744942 | 0.486658323 |
| ILMN_2357976 | BAT1 | NM_004640.5 | 0.008748889 | 0.39869983 |
| ILMN_1686804 | CCRK | NM_012119.3 | 0.008781738 | 1.379683611 |
| ILMN_1735908 | UTP15 | NM_032175.2 | 0.008795849 | 0.455716604 |
| ILMN_1739496 | PRRX1 | NM_006902.3 | 0.008810631 | 1.352203092 |
| ILMN_2215631 | OTUD6B | NM_016023.2 | 0.008824788 | 0.318170009 |
| ILMN_1676449 | SLIT2 | NM_004787.1 | 0.008825626 | 1.443309256 |
| ILMN_1717982 | BZW1 | NM_014670.2 | 0.008843056 | 0.496720206 |
| ILMN_2089902 | NUS1 | NM_138459.3 | 0.008924061 | 0.426437437 |
| ILMN_2172269 | TMEM183B | NM_001079809.1 | 0.008947562 | 0.531376285 |
| ILMN_1750144 | C3orf19 | NM_016474.4 | 0.008998487 | 1.224881041 |
| ILMN_1686043 | FAM164C | NM_024643.2 | 0.009007654 | 0.524954198 |
| ILMN_2342793 | FBXW8 | NM_153348.2 | 0.009010131 | 0.526747165 |
| ILMN_1684554 | COL16A1 | NM_001856.3 | 0.009207494 | 2.157593197 |
| ILMN_2198878 | INPP4B | NM_003866.1 | 0.009224731 | 1.355483357 |
| ILMN_2183610 | SERAC1 | NM_032861.2 | 0.009237213 | 0.652929929 |
| ILMN_1735827 | NISCH | NM_007184.3 | 0.009267976 | 3.244972339 |
| ILMN_2408815 | NAP1L1 | NM_139207.1 | 0.009273677 | 0.466078202 |
| ILMN_1736154 | ProSAPiP1 | NM_014731.2 | 0.009297408 | 1.371836507 |
| ILMN_1660043 | UBXN11 | NM_145345.2 | 0.009301234 | 0.414923686 |
| ILMN_1723087 | MDK | NM_002391.3 | 0.009357376 | 0.477925138 |
| ILMN_2405190 | VAPA | NM_003574.5 | 0.009380725 | 0.642869229 |
| ILMN_2365549 | BRPF1 | NM_004634.2 | 0.009418423 | 0.030900528 |
| ILMN_1688637 | TMEM198 | NM_001005209.1 | 0.009454295 | 0.53441861 |
| ILMN_2381753 | G3BP2 | NM_012297.3 | 0.009454643 | 0.528560031 |
| ILMN_2119945 | NDUFB3 | NM_002491.1 | 0.009512793 | 0.605900377 |
| ILMN_2395913 | ARHGAP11A | NM_199357.1 | 0.009513189 | 0.52537859 |
| ILMN_1799105 | COL17A1 | NM_000494.3 | 0.009521418 | 0.569237452 |
| ILMN_1786707 | C19orf63 | NM_175063.4 | 0.009549933 | 0.705859833 |
| ILMN_1695962 | SLC12A9 | NM_020246.2 | 0.00955532 | 0.632986434 |
| ILMN_2213247 | SPCS2 | NM_014752.1 | 0.009568632 | 0.468103464 |
| ILMN_1722016 | LY6G5C | NM_001002849.1 | 0.009572932 | 1.337326232 |
| ILMN_1809141 | ING4 | NM_198287.1 | 0.009584963 | 0.47920737 |
| ILMN_1682332 | GYPC | NM_016815.2 | 0.009633083 | 1.887056171 |
| ILMN_1761363 | VAMP4 | NM_003762.3 | 0.009646552 | 0.476950334 |
| ILMN_1785179 | UBE2G2 | NM_003343.4 | 0.009701867 | 0.617105146 |
| ILMN_1763000 | ADAP2 | NM_018404.2 | 0.009748952 | 1.681799633 |
| ILMN_1716224 | STARD4 | NM_139164.1 | 0.009783456 | 0.489406267 |
| ILMN_1739587 | UTY | NM_007125.3 | 0.009816309 | 0.439298478 |
| ILMN_1680643 | KIAA1333 | NM_017769.2 | 0.009820691 | 0.460192694 |
| ILMN_2407879 | SORBS2 | NM_003603.4 | 0.009831185 | 1.548113873 |
| ILMN_2275533 | DIAPH3 | NM_030932.3 | 0.009833778 | 0.686553443 |
| ILMN_1773645 | GMPPB | NM_021971.1 | 0.009837559 | 0.446130182 |
| ILMN_1764091 | R3HDM2 | NM_014925.2 | 0.009843159 | 0.685043284 |
| ILMN_2400500 | LASS2 | NM_181746.2 | 0.009847868 | 0.442253826 |
| ILMN_2334350 | BTBD3 | NM_014962.2 | 0.00985416 | 0.459870001 |
| ILMN_1660602 | C1orf43 | NM_015449.2 | 0.009874084 | 0.617987793 |
| ILMN_2170353 | PTPLB | NM_198402.2 | 0.009918567 | 0.400585431 |
| ILMN_1794492 | HOXC6 | NM_153693.3 | 0.00992158 | 0.721974031 |
| ILMN_2364357 | RPS6KB2 | NM_003952.2 | 0.009937711 | 0.244179599 |

TABLE 3-continued

| PROBE_ID | SYMBOL | Accession number | pvalue | hazard |
|---|---|---|---|---|
| ILMN_2147503 | ALG13 | NM_018466.3 | 0.009946793 | 0.352771071 |
| ILMN_2177460 | AQR | NM_014691.2 | 0.009953961 | 0.404663806 |
| ILMN_1668525 | NR3C1 | NM_001018076.1 | 0.009992789 | 0.617215381 |
| ILMN_2258543 | PRDM2 | NM_012231.3 | 0.009994008 | 1.364891701 |

Example 6

Identification of Reference Genes for Self-Normalization

One of the ways to reduce the number of prognostic genes discovered in the clinical field is self-normalization in each case since it is not possible to normalize at a time with an entire group of the patients as the subject. Currently, real-time QRT-PCR (real time quantitative reverse transcription polymerase chain reaction) is widely used to measure the expression level of gene, but when QTR-PCR is used, all the genes in the human cannot be measured in order to perform quantile normalization, and there is a problem of significantly lower real-time QRT-PCR signal generated when old paraffin block is used than when new sample is used.

Hereupon, the present inventors tried to identify the reference gene for self-normalization of the measured expression level of genes for the reliable use of gastric cancer prognostic genes identified in the clinical field. Accordingly, 50 reference genes which have no prognostic features and show the minimal change in each different case were identified by analyzing the data of the gene expression levels measured with WG-DASL in Example 3, and the results are shown in Table 4. The combination of one or more genes in 50 reference genes listed in Table 4 can be used for the normalization of expression levels of gastric cancer prognostic genes.

TABLE 4

| PROBE_ID | Accession number | SYMBOL |
|---|---|---|
| ILMN_2403446 | NM_007011.5 | ABHD2 |
| ILMN_1708502 | NM_014423.3 | AFF4 |
| ILMN_1780806 | NM_025190.3 | ANKRD36B |
| ILMN_2415467 | NM_080550.2 | AP1GBP1 |
| ILMN_1722066 | NM_018120.3 | ARMC1 |
| ILMN_2352934 | NM_004318.2 | ASPH |
| ILMN_1808163 | NM_022338.2 | C11orf24 |
| ILMN_1693431 | NM_153218.1 | C13orf31 |
| ILMN_1733288 | NM_016546.1 | C1RL |
| ILMN_2202940 | NM_020244.2 | CHPT1 |
| ILMN_2188533 | NT_007592.15 | CICK0721Q.1 |
| ILMN_1795754 | NM_001289.4 | CLIC2 |
| ILMN_2373779 | NM_198189.2 | COPS8 |
| ILMN_1796180 | NM_021117.2 | CRY2 |
| ILMN_1651499 | NM_020462.1 | ERGIC1 |
| ILMN_1751425 | NM_024896.2 | ERMP1 |
| ILMN_1712095 | NM_005938.2 | FOXO4 |
| ILMN_1747305 | NM_175571.2 | GIMAP8 |
| ILMN_1737308 | NM_002064.1 | GLRX |
| ILMN_2168215 | NM_016153.1 | HSFX1 |
| ILMN_1789018 | NM_012218.2 | ILF3 |
| ILMN_1809141 | NM_016162.2 | ING4 |
| ILMN_1807767 | NM_014615.1 | KIAA0182 |
| ILMN_1776963 | NM_006816.1 | LMAN2 |
| ILMN_1743583 | NM_130473.1 | MADD |
| ILMN_1774844 | NM_032960.2 | MAPKAPK2 |
| ILMN_1761858 | NM_033290.2 | MID1 |
| ILMN_1670801 | NM_000254.1 | MTR |
| ILMN_1780937 | NM_025128.3 | MUS81 |
| ILMN_1784113 | NM_020378.2 | NAT14 |
| ILMN_2147133 | NM_173638.2 | NBPF15 |
| ILMN_2361185 | NM_024878.1 | PHF20L1 |

TABLE 4-continued

| PROBE_ID | Accession number | SYMBOL |
|---|---|---|
| ILMN_1704529 | NM_021130.3 | PPIA |
| ILMN_2357577 | NM_006251.5 | PRKAA1 |
| ILMN_2353202 | NM_152882.2 | PTK7 |
| ILMN_1813753 | NM_002825.5 | PTN |
| ILMN_1677843 | NM_001031677.2 | RAB24 |
| ILMN_1773561 | NM_021183.3 | RAP2C |
| ILMN_1749006 | NM_052862.2 | RCSD1 |
| ILMN_2373266 | NM_139168.2 | SFRS12 |
| ILMN_2117716 | NM_005088.2 | SFRS17A |
| ILMN_2379835 | NM_003352.4 | SUMO1 |
| ILMN_1712075 | NM_015286.5 | SYNM |
| ILMN_1674866 | NM_006354.2 | TADA3L |
| ILMN_2390227 | NM_015043.3 | TBC1D9B |
| ILMN_1657983 | NM_018975.2 | TERF2IP |
| ILMN_1705213 | NM_022152.4 | TMBIM1 |
| ILMN_1756696 | NM_207291.1 | USF2 |
| ILMN_2054442 | NM_001099639.1 | ZNF146 |
| ILMN_2352590 | NM_006974.2 | ZNF33A |

Figure 1:
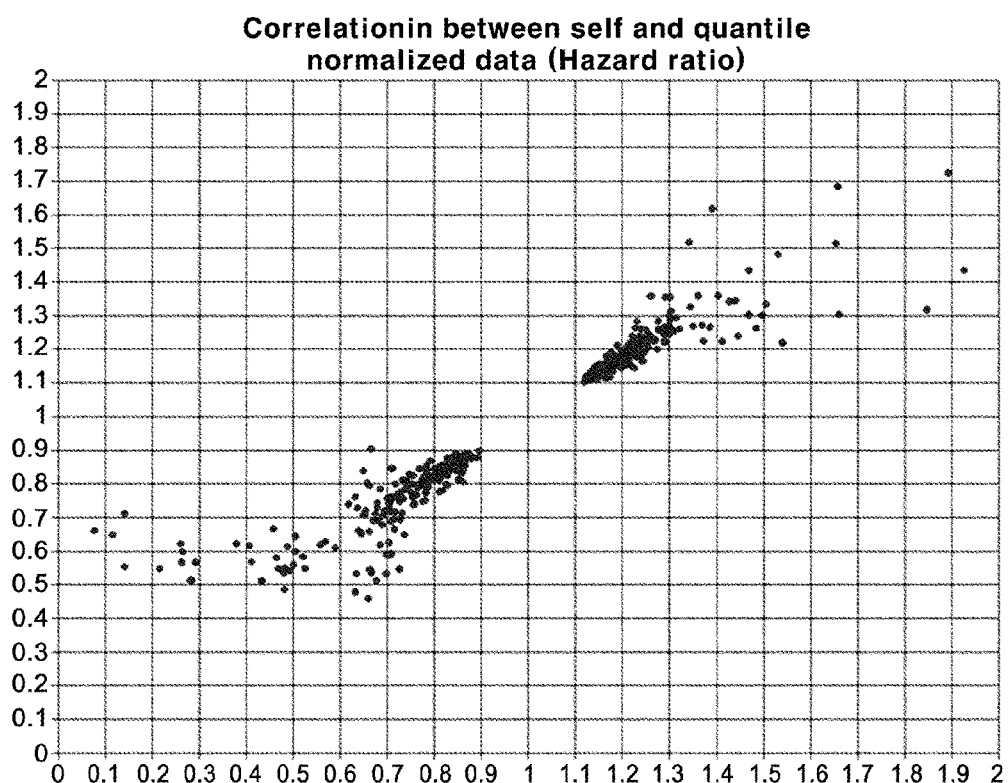
FIG. 1 is a graph showing the relationship between the risks based on quantile normalization and self-standardization using reference gene.
Figure 2A:
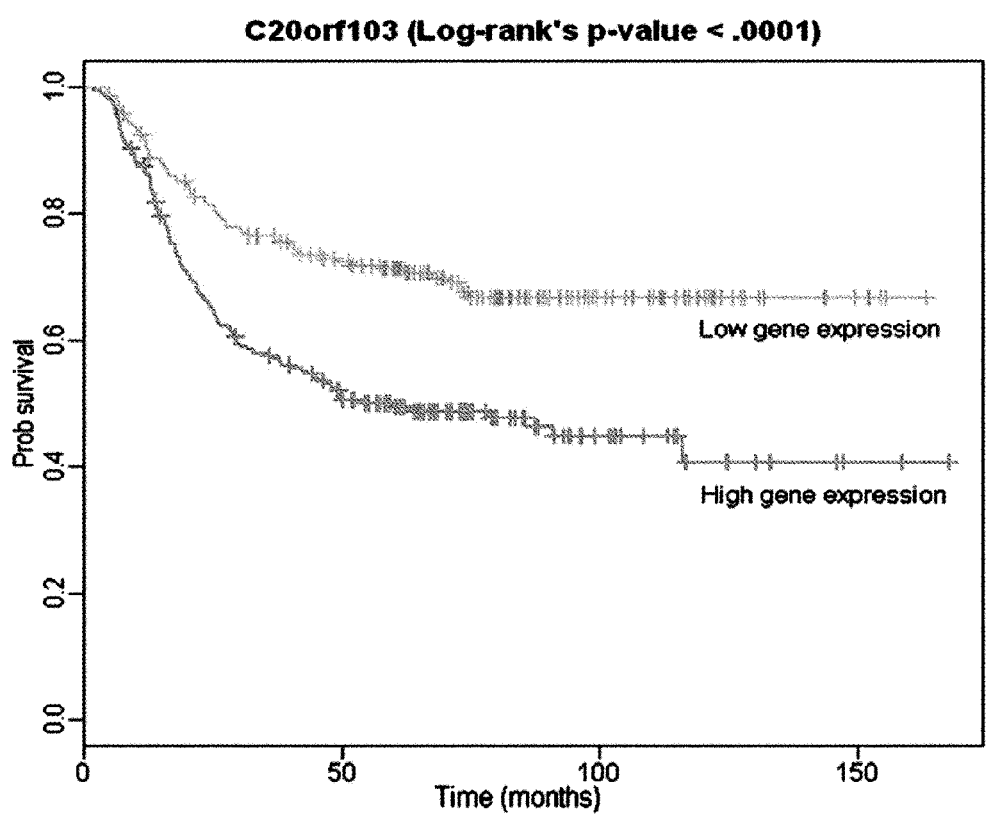
FIGS. 2a and 2b represent the Kaplan-Meier plot according to the expression level of C20orf103, COL10A1 genes.
Figure 2B:
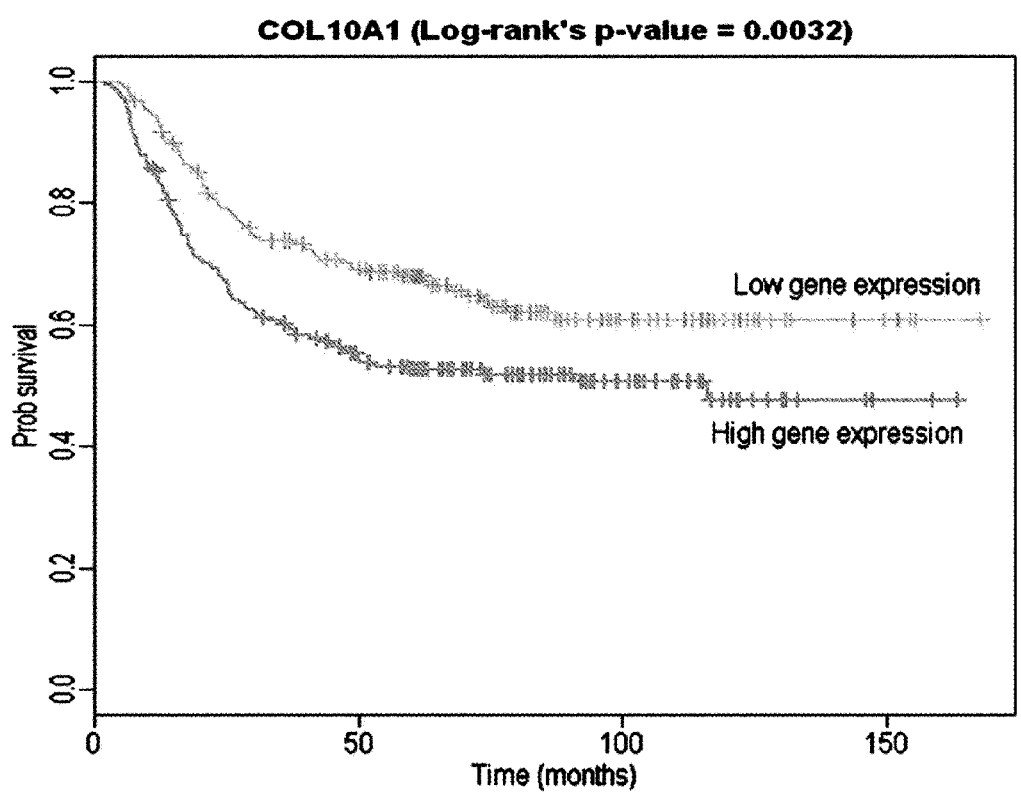
Figure 3A:
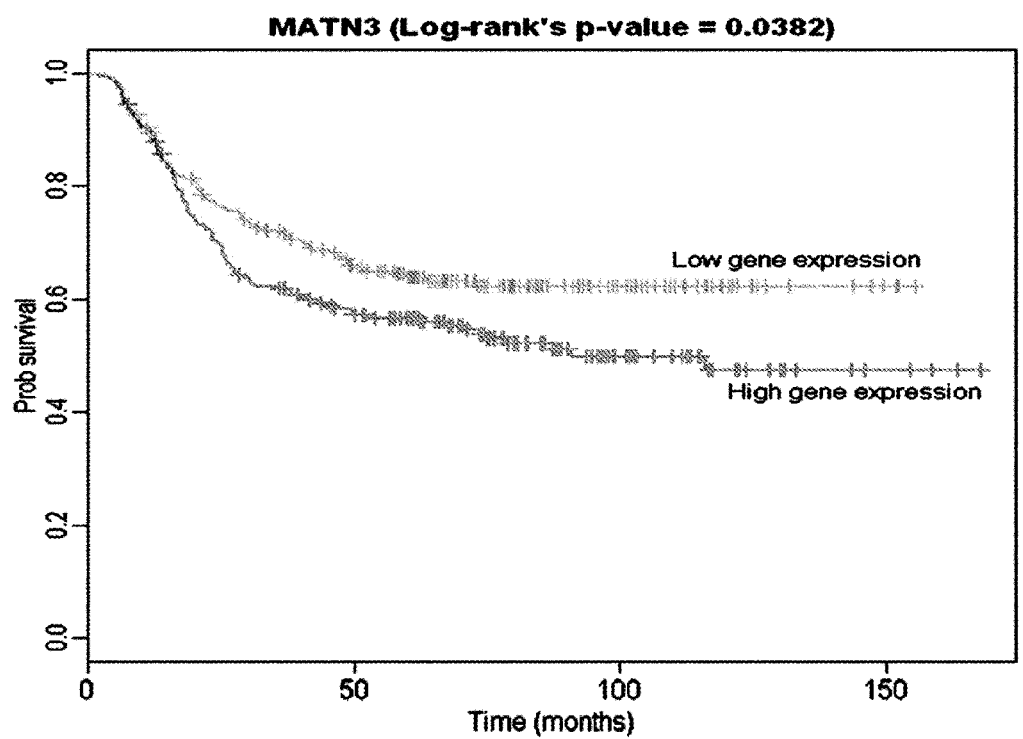
FIGS. 3a and 3b represent the Kaplan-Meier plot according to the expression level of MATN3, FMO2 genes.
Figure 3B:
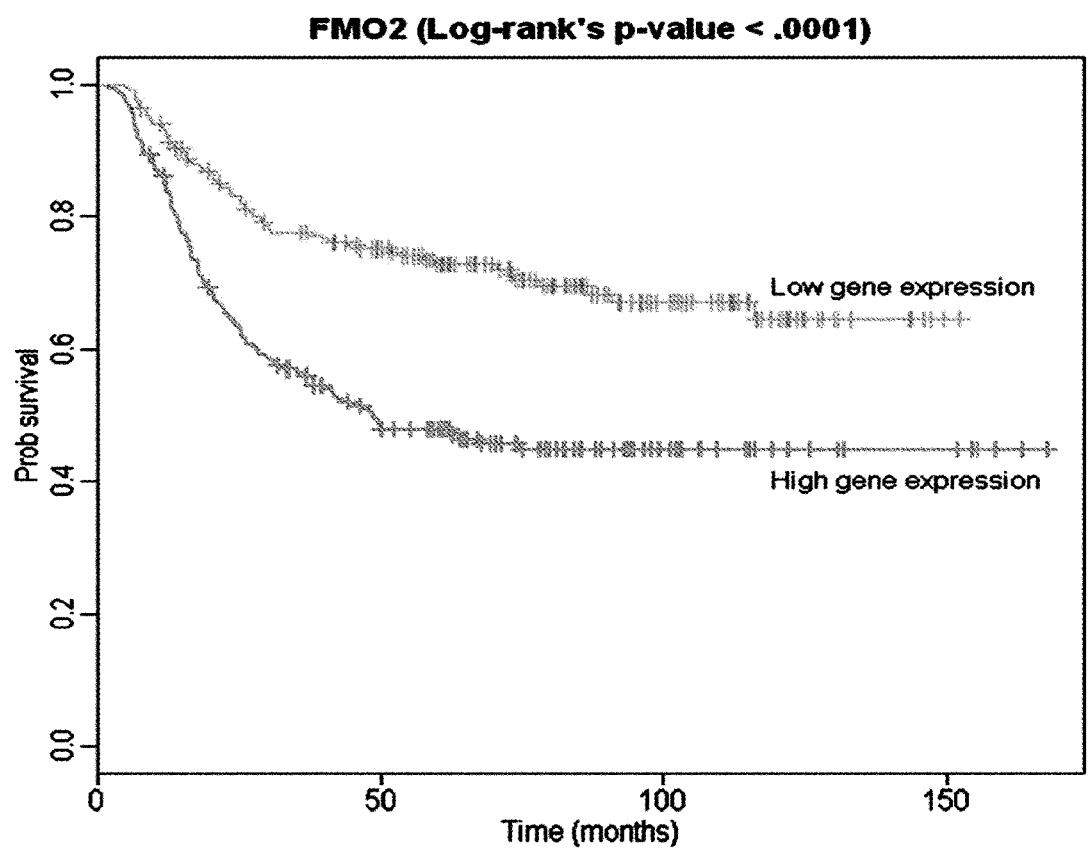
Figure 4A:
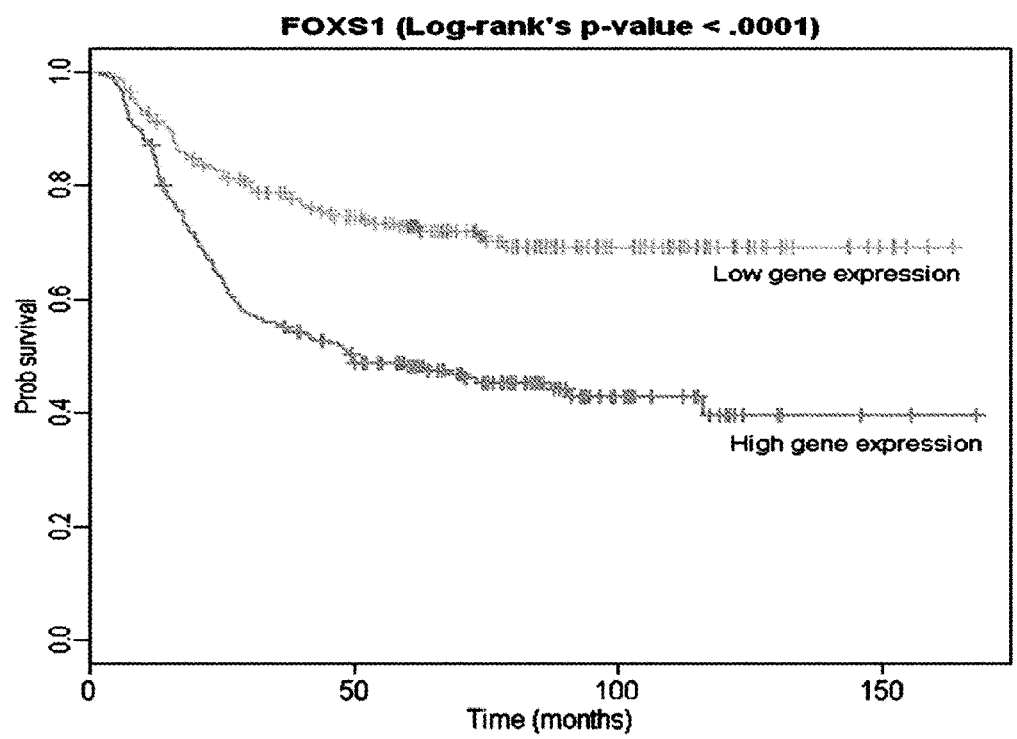
FIGS. 4a and 4b represent the Kaplan-Meier plot according to the expression level of FOXS1, COL8A1 genes.
Figure 4B:
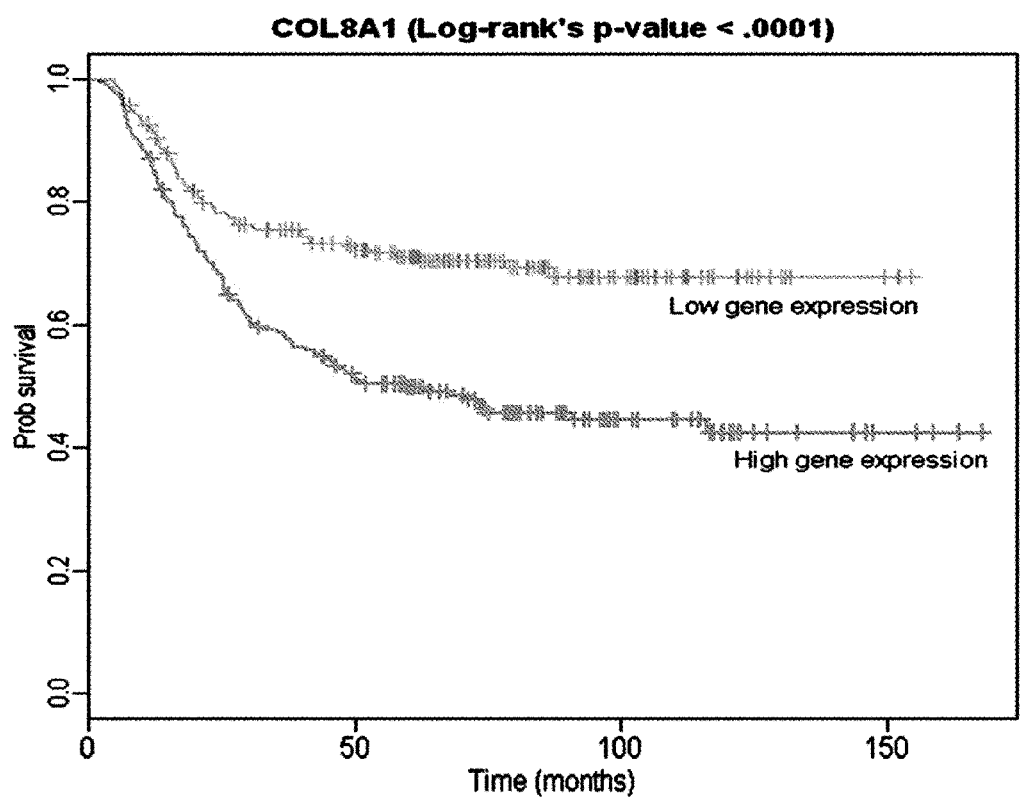
Figure 5A:
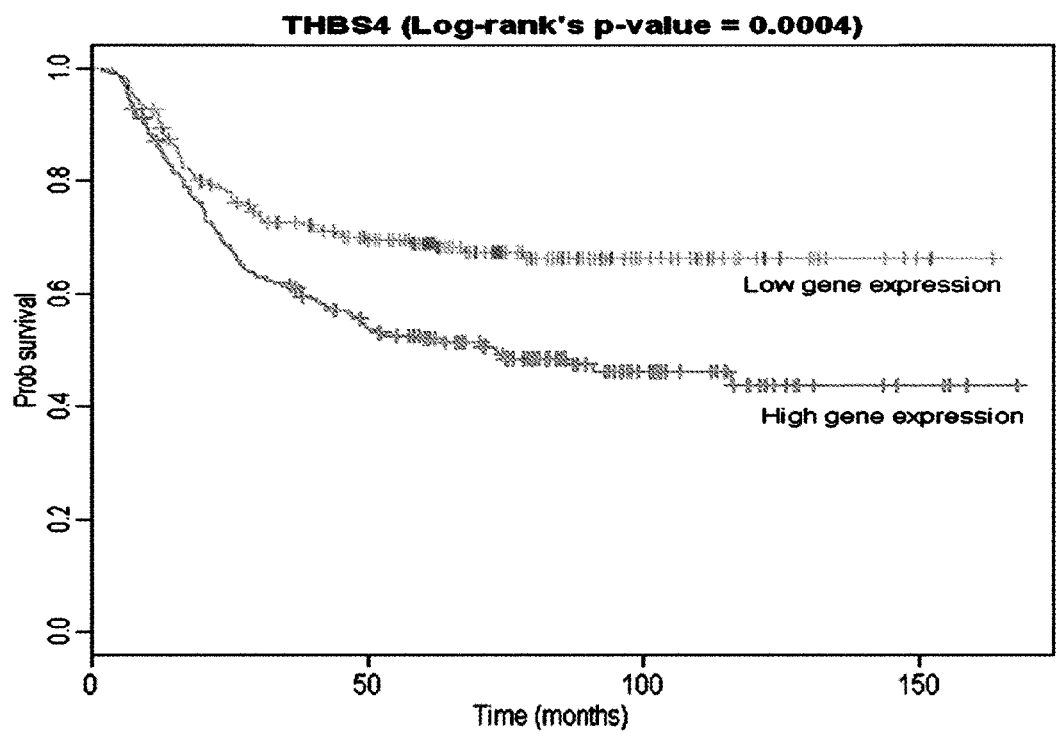
FIGS. 5a and 5b represent the Kaplan-Meier plot according to the expression level of THBS4, ALAS1 genes.
Figure 5B:
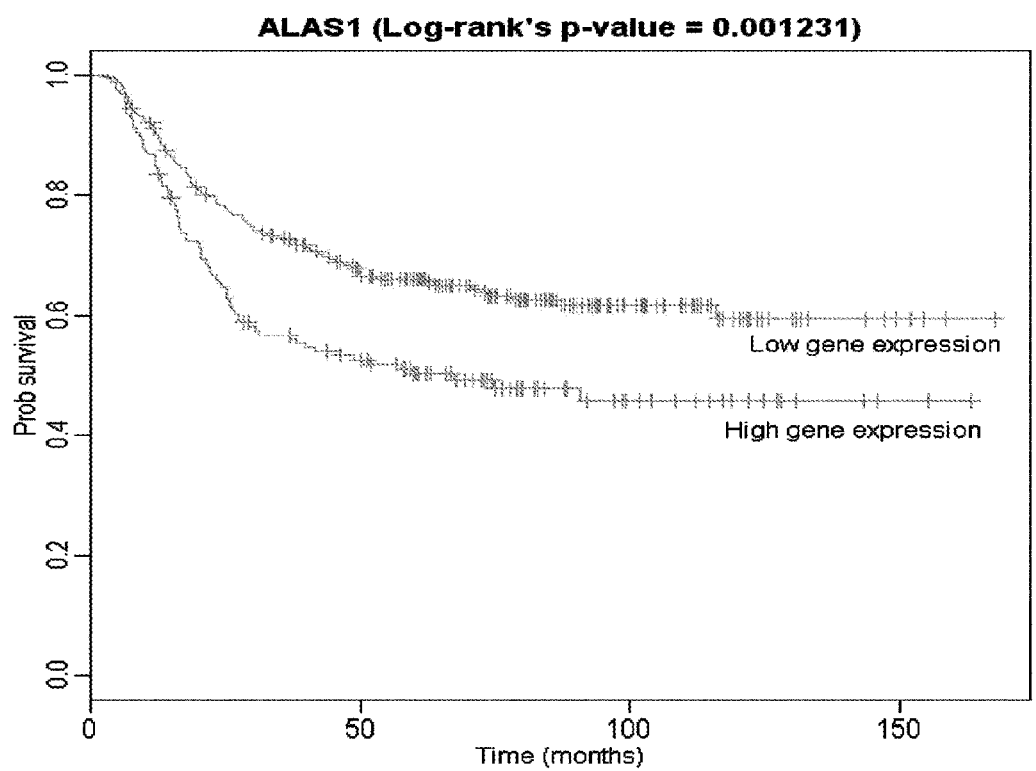
Figure 6A:
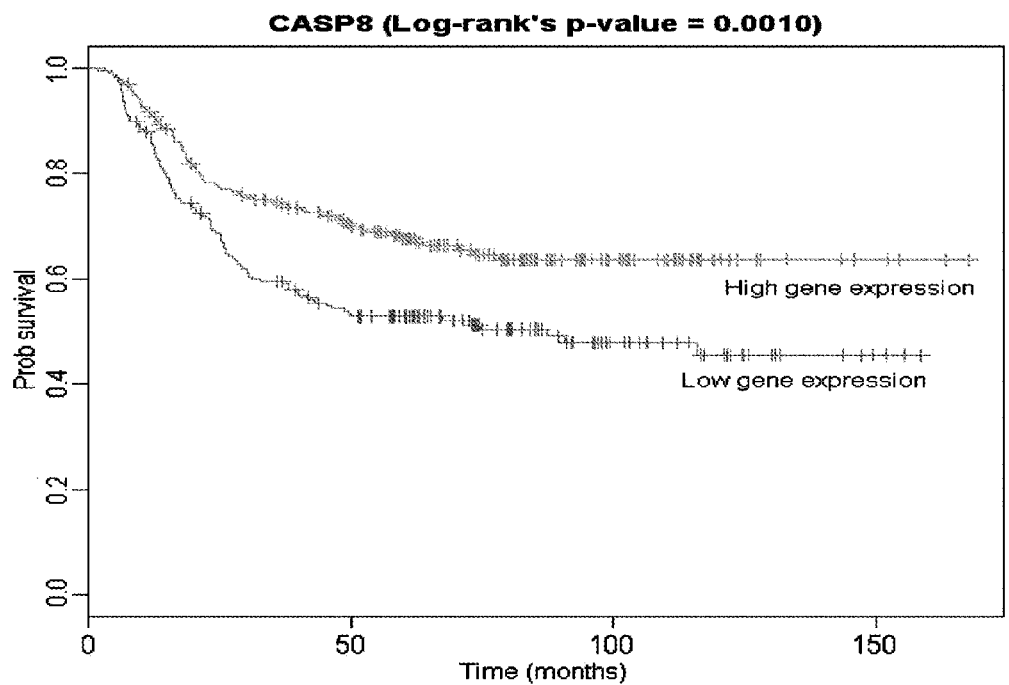
FIGS. 6a and 6b represent the Kaplan-Meier plot according to the expression level of CASP8, CLYBL genes.
Figure 6B:
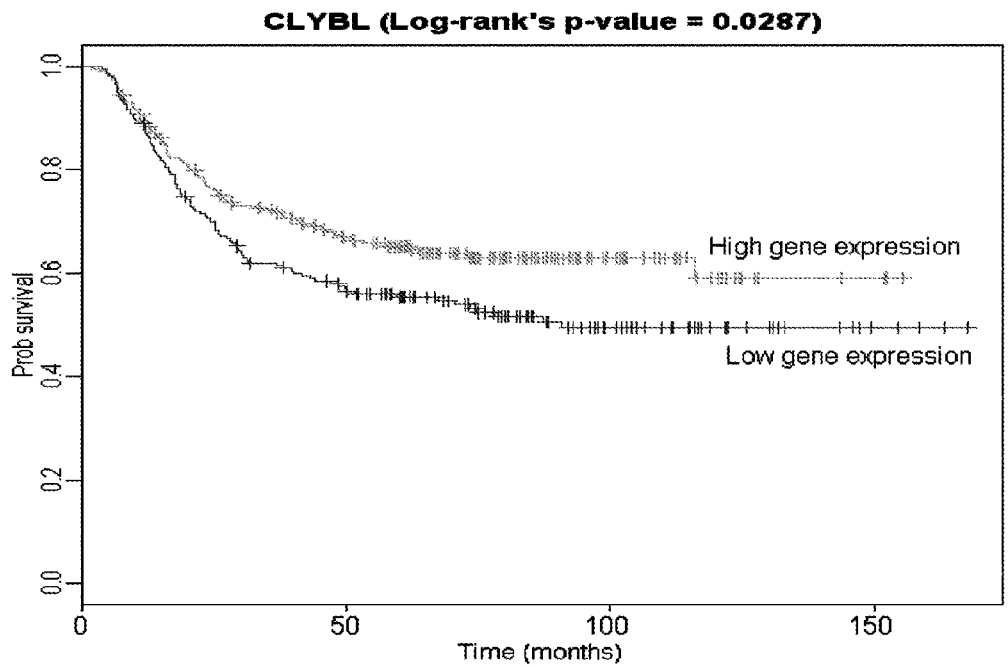
Figure 7A:
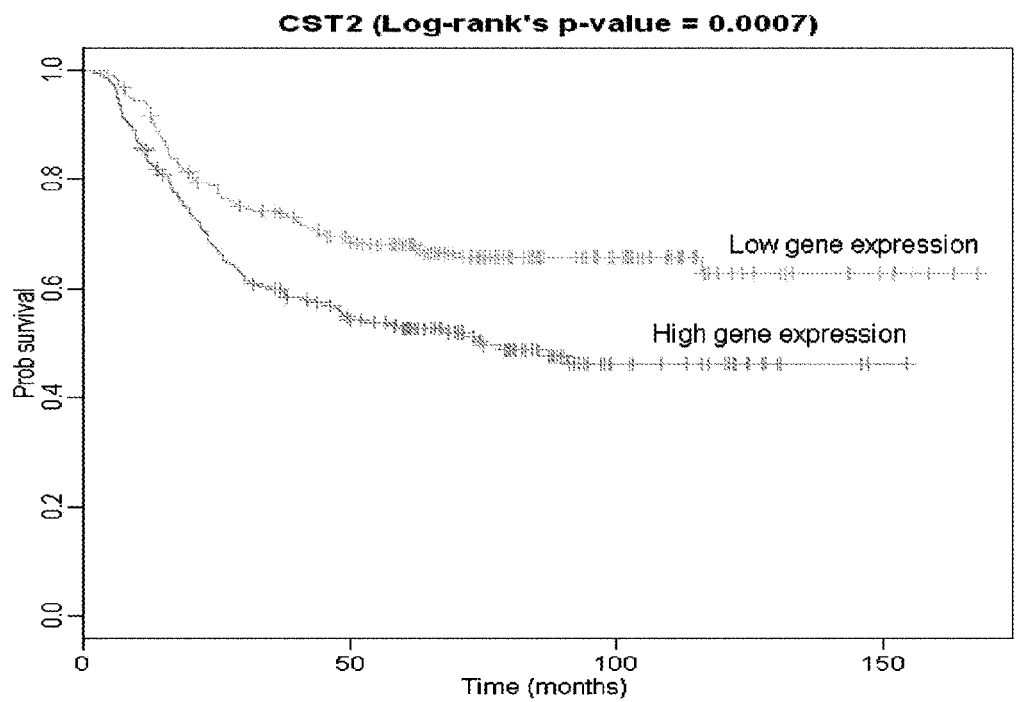
FIGS. 7a and 7b represent the Kaplan-Meier plot according to the expression level of CST2, HSPC159 genes.
Figure 7B:
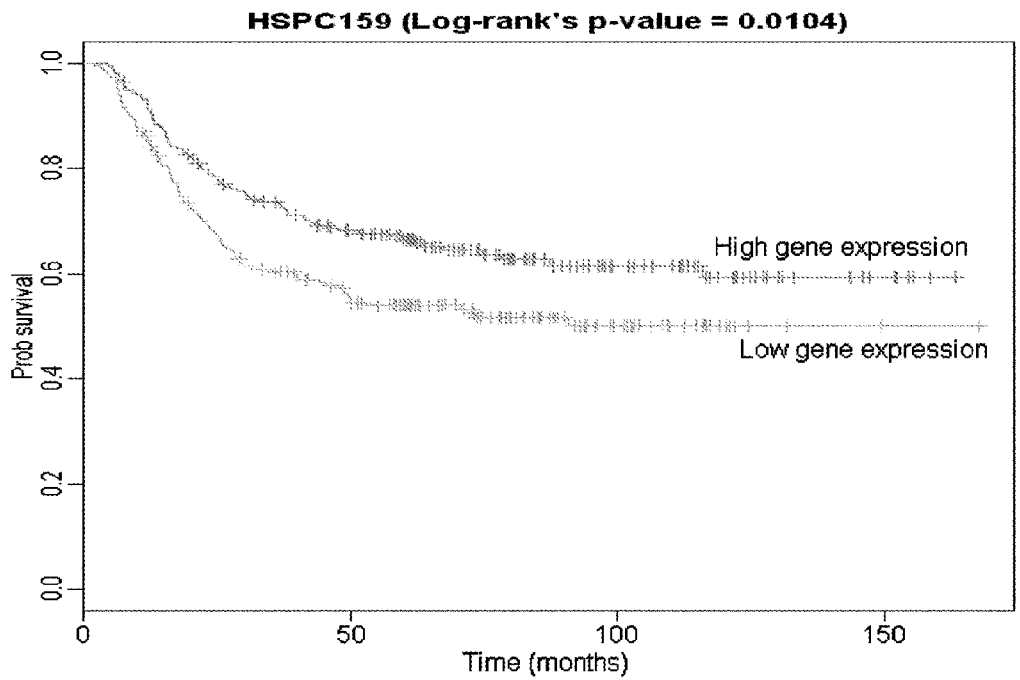
Figure 8A:
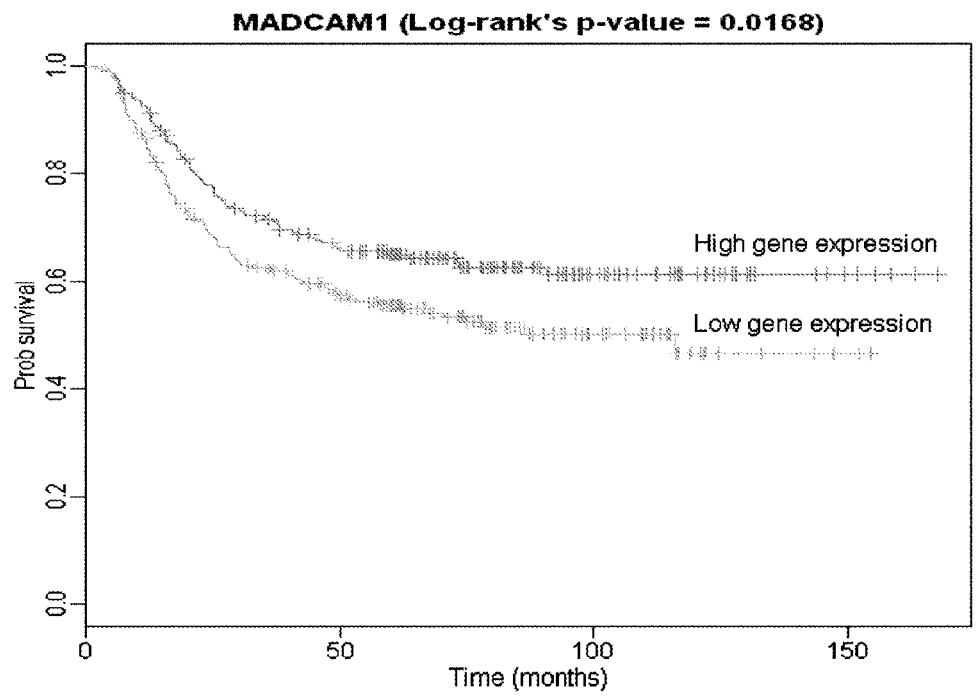
FIGS. 8a and 8b represent the Kaplan-Meier plot according to the expression level of MADCAM1, MAF genes.
Figure 8B:
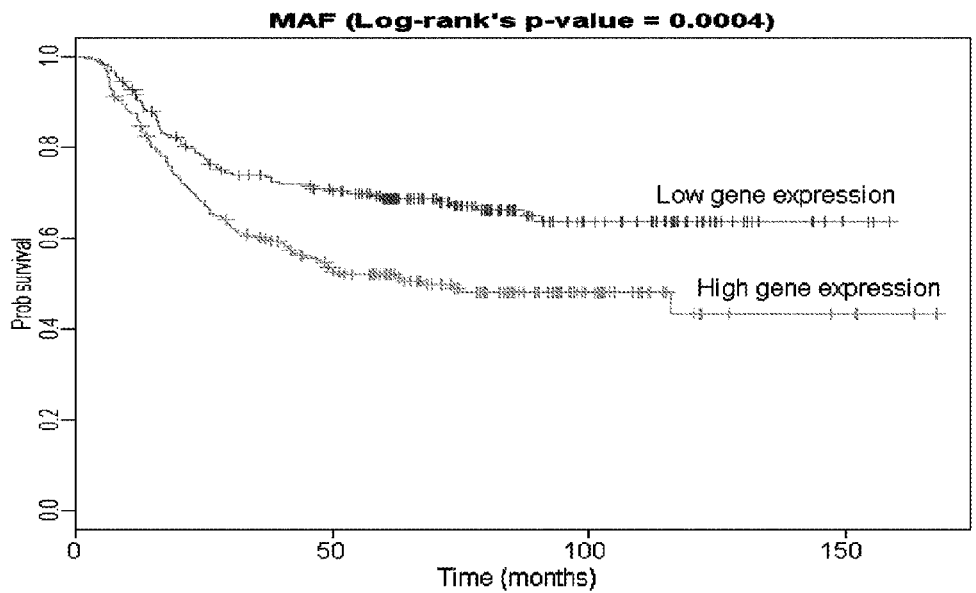
Figure 9A:
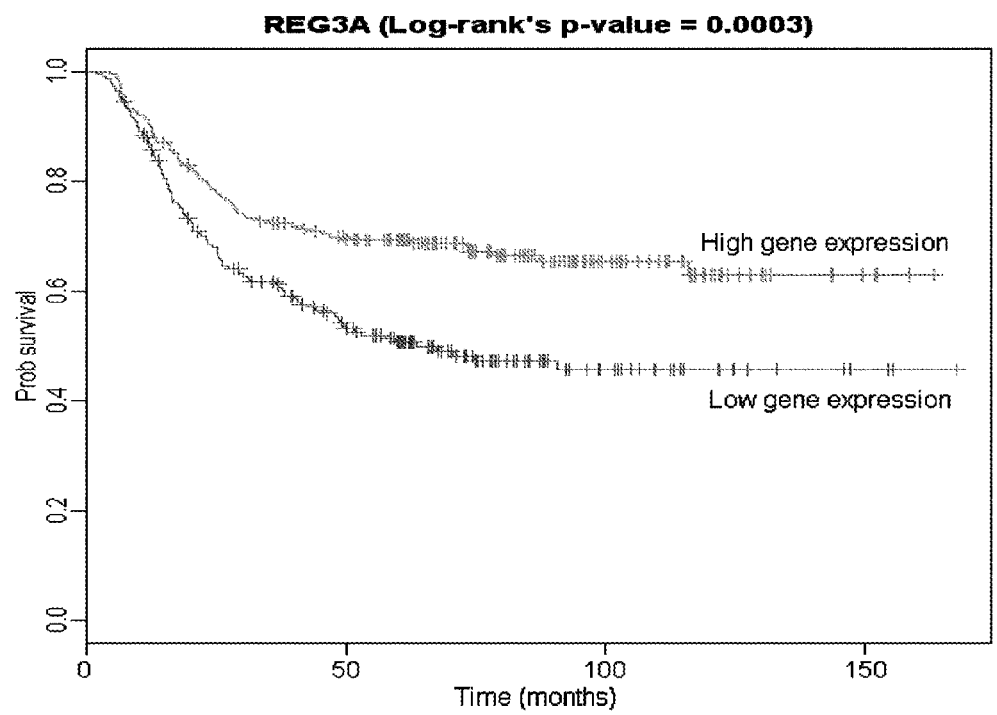
FIGS. 9a and 9b represent the Kaplan-Meier plot according to the expression level of REG3A, RNF152 genes.
Figure 9B:
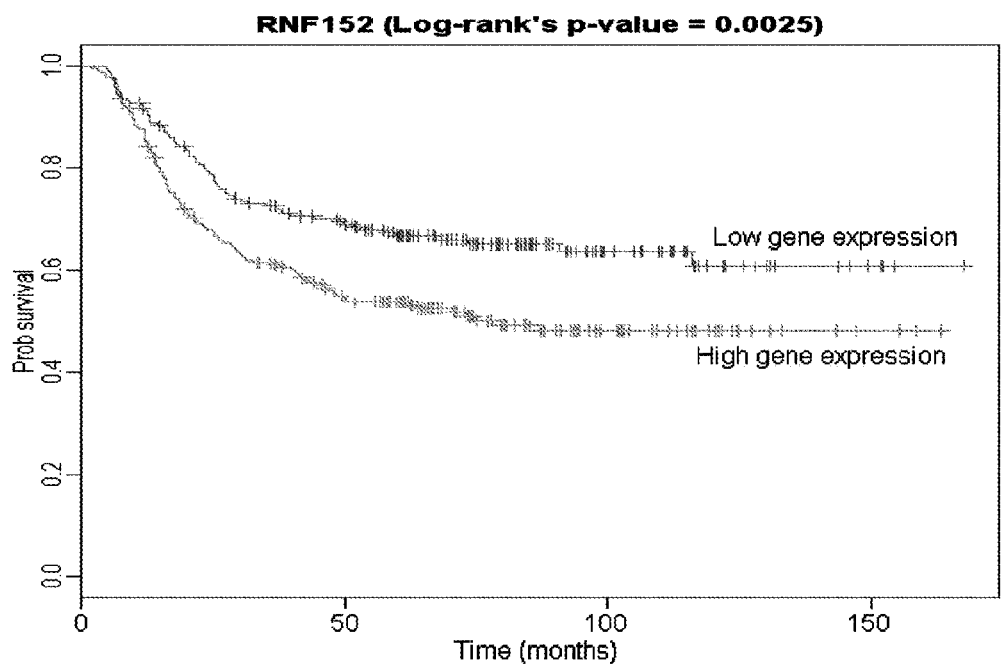
Figure 10A:
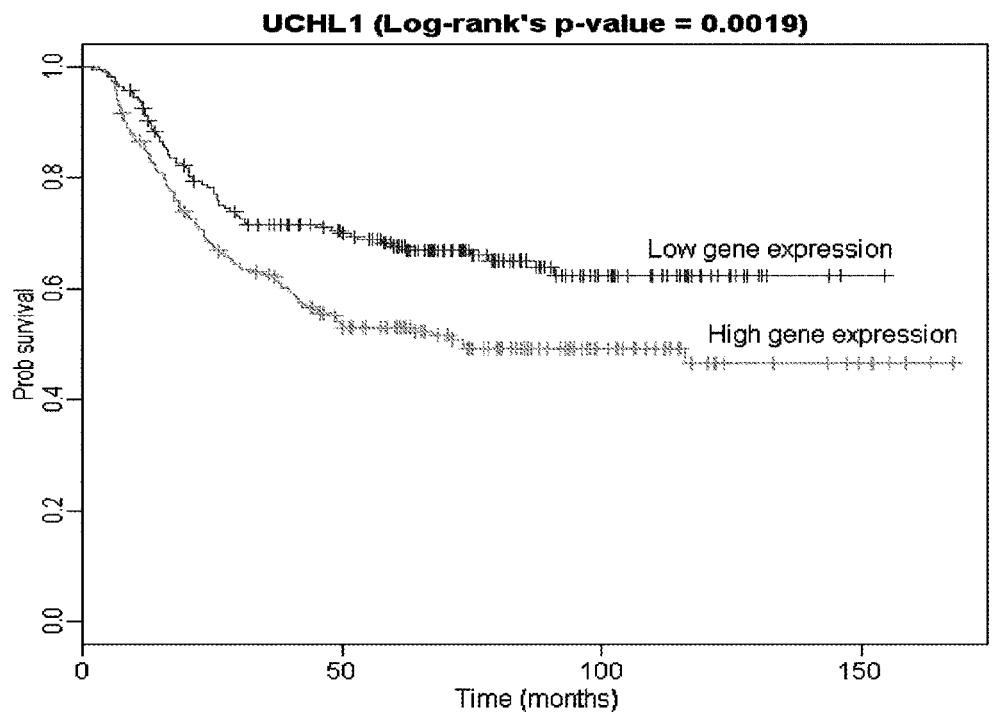
FIGS. 10a and 10b represent the Kaplan-Meierplot according to the expression level of UCHL1, ZBED5 genes.
Figure 10B:
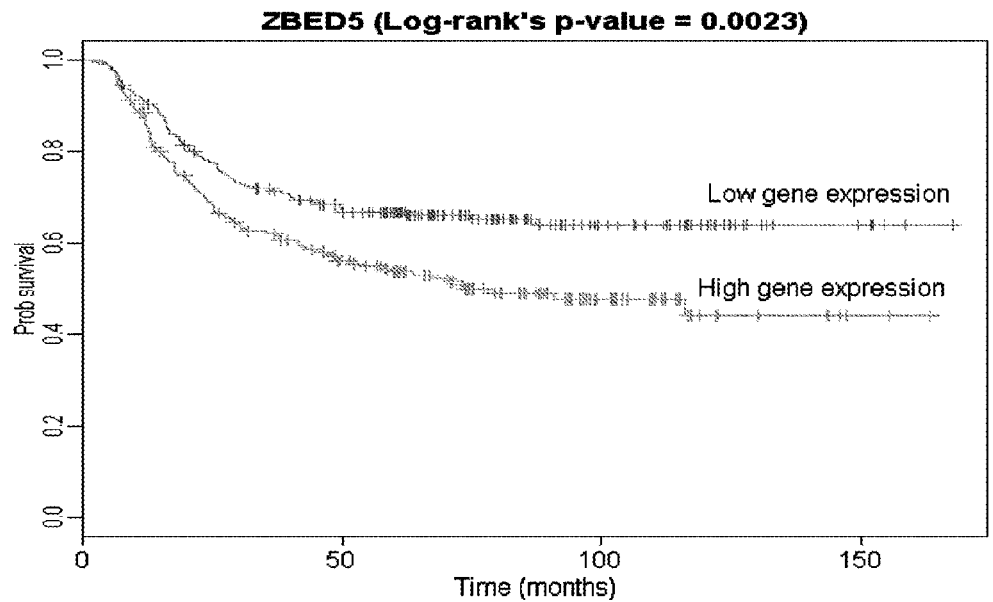
Figure 11A:
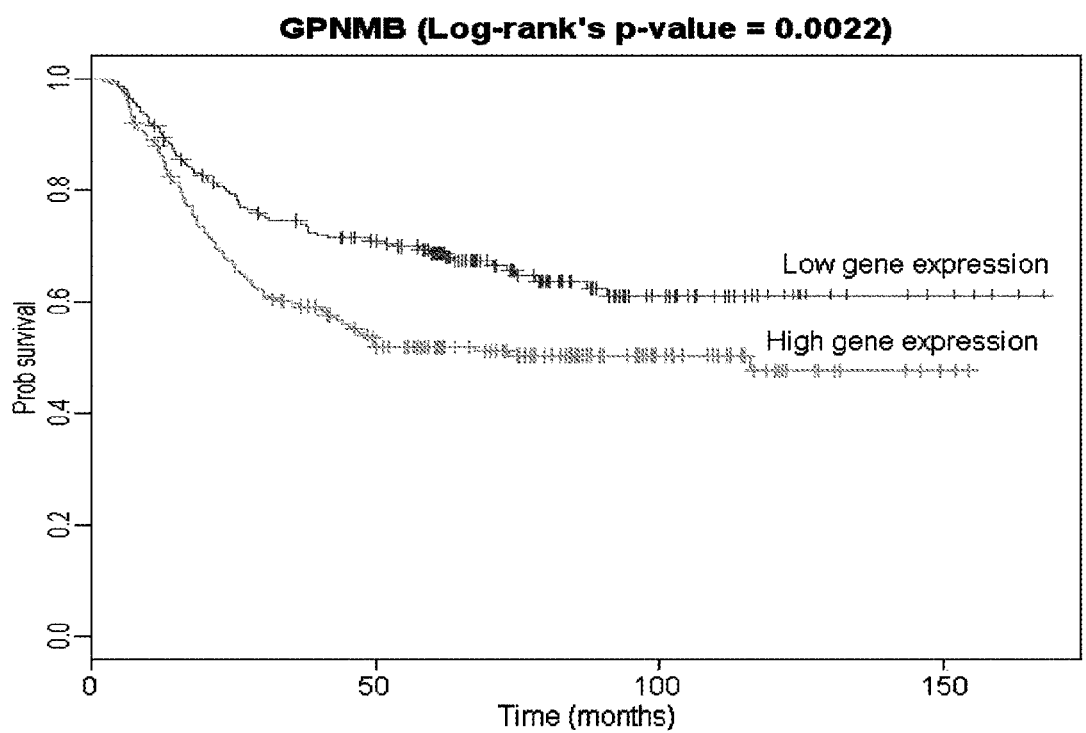
FIGS. 11a and 11b represent the Kaplan-Meier plot according to the expression level of GPNMB, H1ST1H2AJ genes.
Figure 11B:
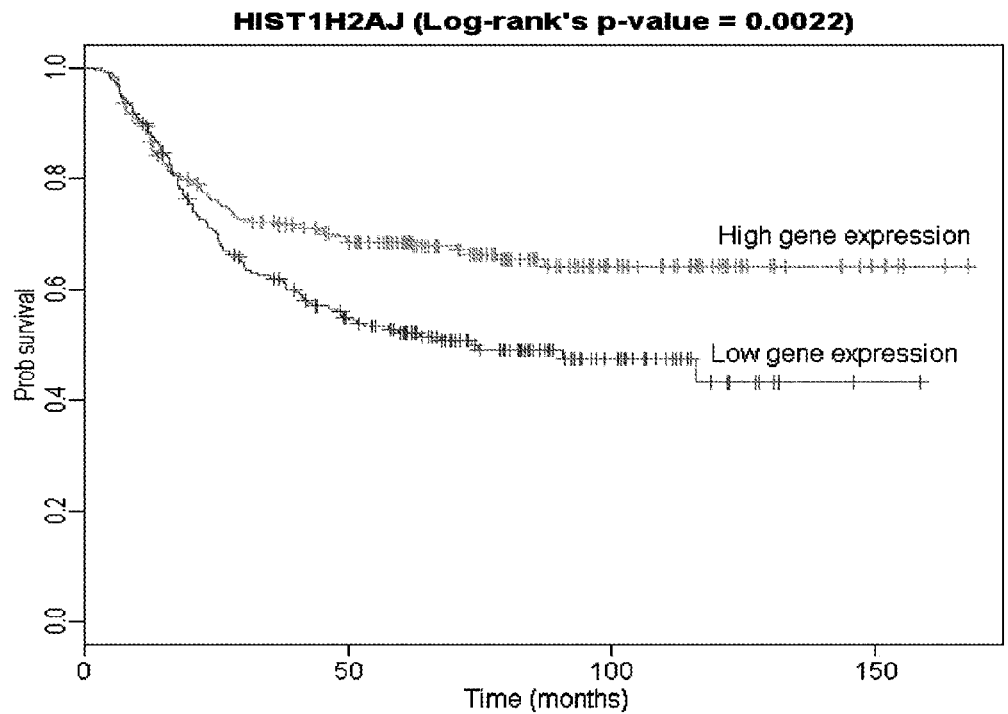
Figure 12A:
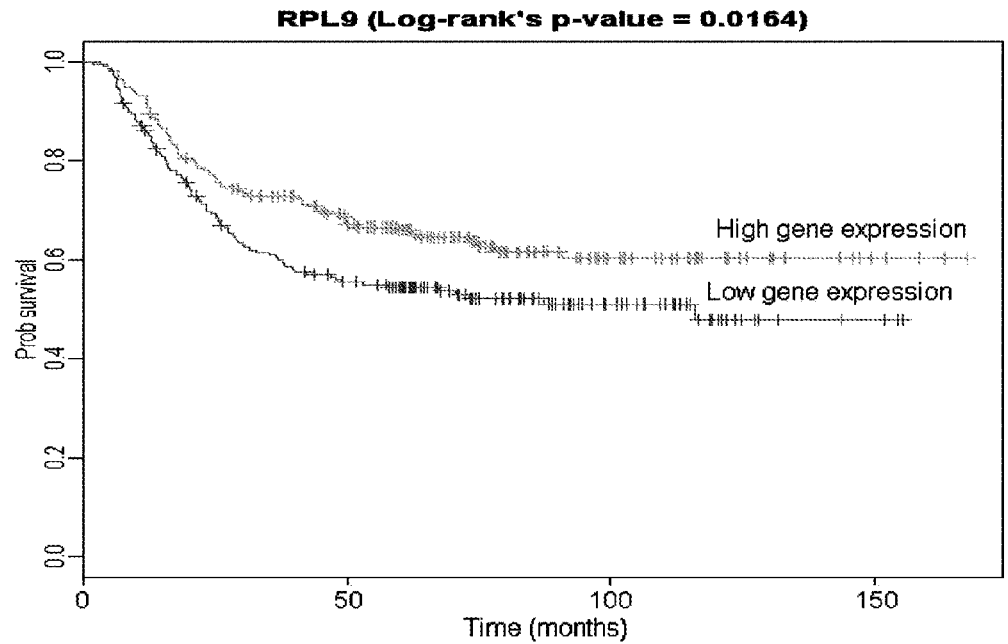
FIGS. 12a and 12b represent the Kaplan-Meier plot according to the expression level of RPL9, DPP6 genes.
Figure 12B:
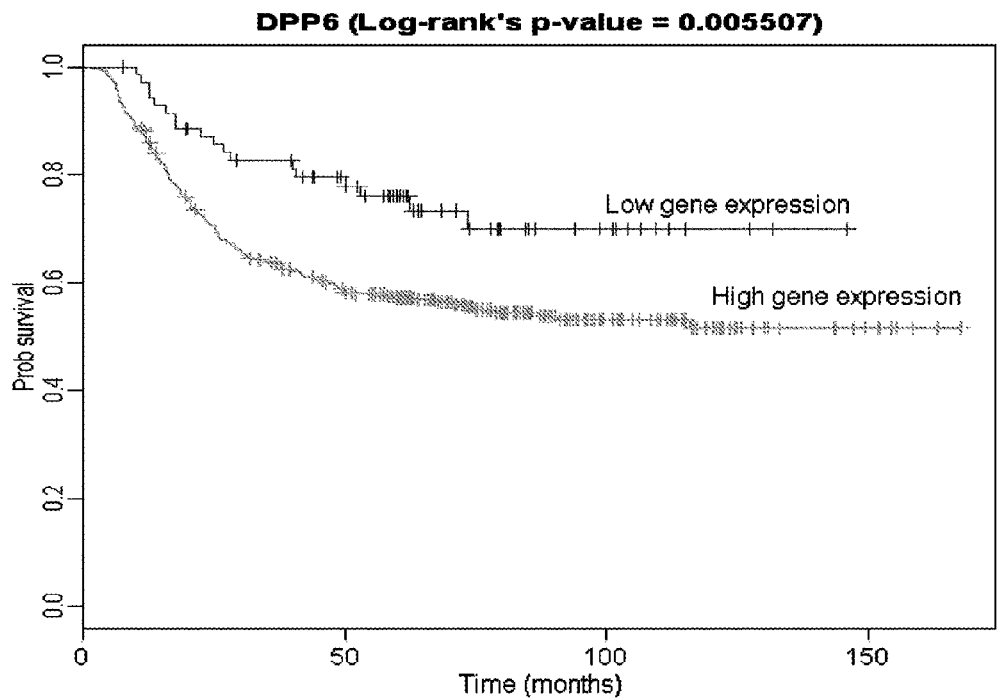
Figure 13A:
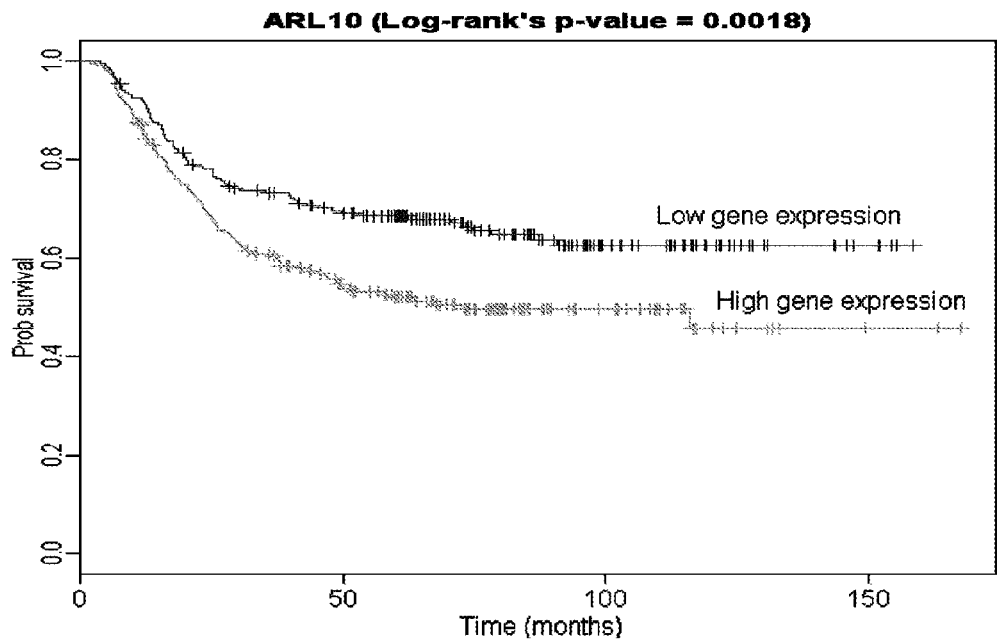
FIGS. 13a and 13b represent the Kaplan-Meier plot according to the expression level of ARL10, ISLR2 genes.
Figure 13B:
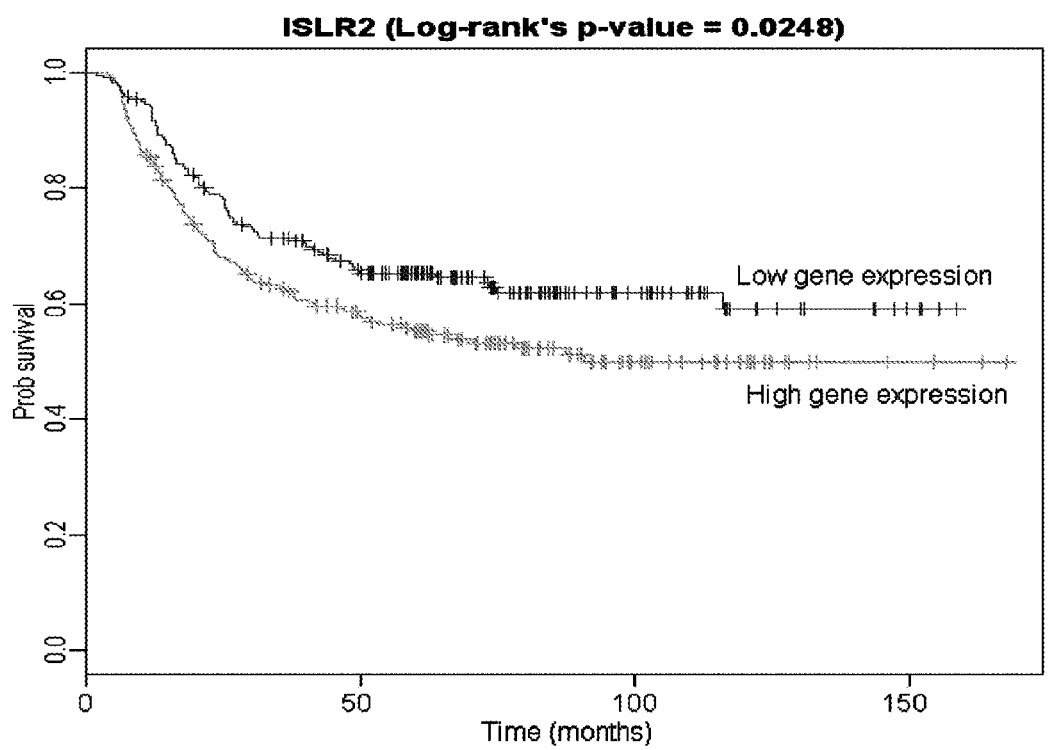
Figure 14A:
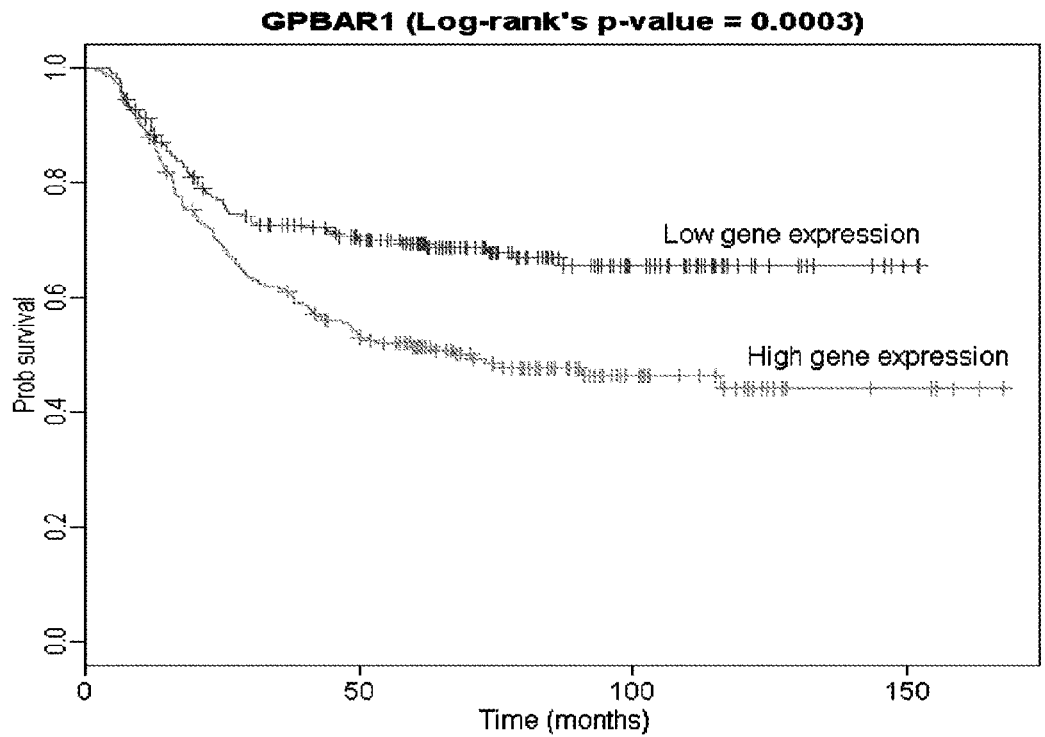
FIGS. 14a and 14b represent the Kaplan-Meier plot according to the expression level of GPBAR1, CPS1 genes.
Figure 14B:
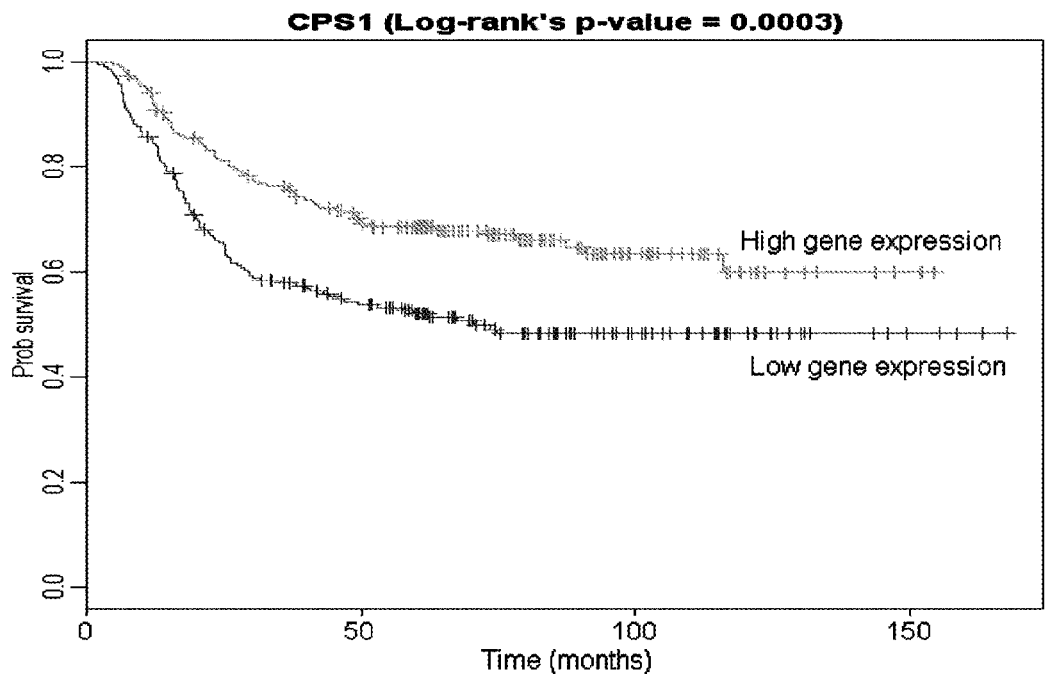
Figure 15A:
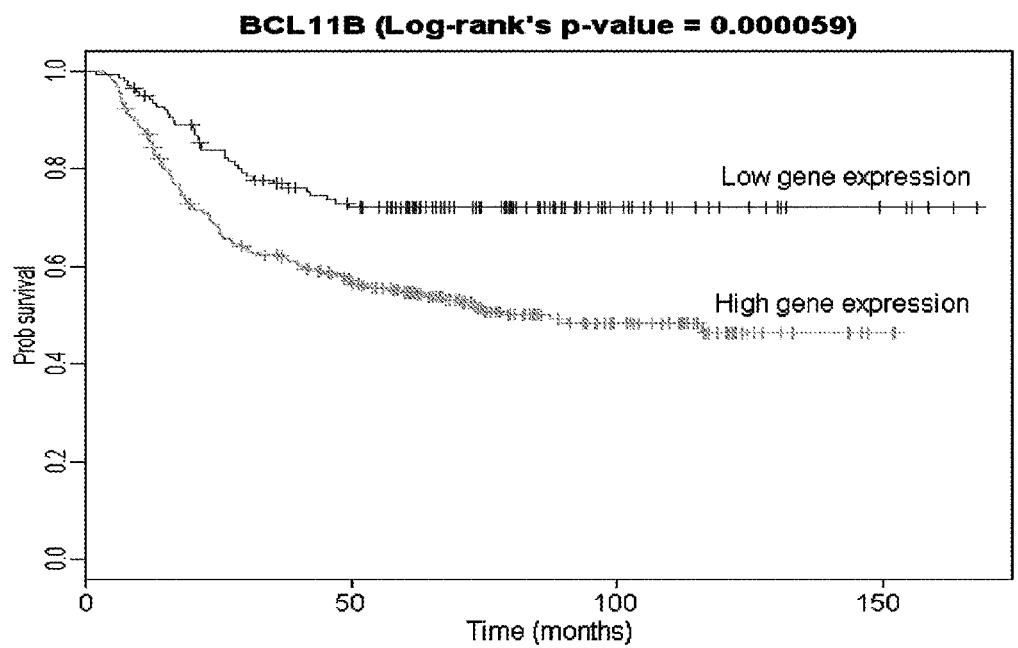
FIGS. 15a and 15b represent the Kaplan-Meier plot according to the expression level of BCL11B, PCDHGA8 genes.
Figure 15B:
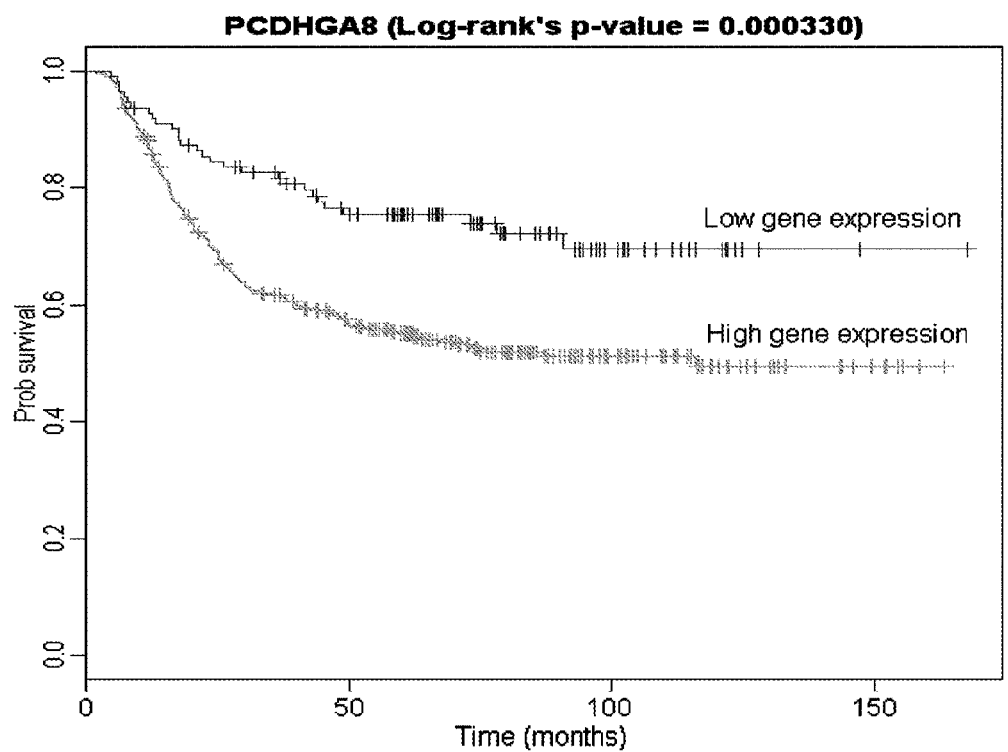

Subsequently, in order to confirm the validity of the self-normalization by reference genes, the correlation between quantile normalization for WG-DASL data and self-normalized data was investigated. The hazard ratios based on the two normalization methods are illustrated in FIG. 1. As a result, the close correlation between the quantile normalization and self-normalization method is identified (FIG. 1).

Example 7

Development and Evaluation of Prognosis Prediction Model Based on the Gastric Cancer Prognostic Genes—(1)

7-1: Prognosis Prediction Model Using Supervised Principal Component Analysis

In order to build the prognosis prediction model, revised Principal Component analysis (SuperPC) developed by Bair and Tibshirani was used (PLoS Biol. 2004 Apr.; 2(4):E108. Epub 2004 Apr. 13). In order to develop and evaluate the gastric cancer prognosis prediction model based on the SuperPC analysis, BRB Array Tools (Simon R et al., Cancer Inform 2007; 3:11-7) program developed by Richard Simon was used.

In SuperPC analysis, threshold p-value for predicting the prognosis at the desirable level can be determined, and in BRB array tools program, default p-value is 0.001. The cut-off p value may be less than 0.01 in any region, and SuperPC analysis may include the subset of prognostic genes listed in Table 2 and Table 3 by predefined p-value and calculation of active ingredient. In order to build the prognosis prediction model with acknowledged validity, 10-fold cross-validation and SuperPC analysis were combined with BRB Array tools. As an example of SuperPC analysis, in order to build a prognosis prediction model, cut-off p-value of 0.00001 and the two active ingredients were used, and SuperPC prognosis prediction model consists of 7 prognostic genes and the prediction model is illustrated in FIG. 16 (Table 5 and FIG. 16).

In addition, Kaplan-Meier plots representing the survival rate according to the expression level of the 7 selected prognostic genes is shown in FIGS. 2 to 5.

TABLE 5

|   | Gene Id | Gene Symbol | Weight ($w_i$) |
|---|---------|-------------|------------|
| 1 | ILMN_1713561 | C20orf103 | 0.152677 |
| 2 | ILMN_1672776 | COL10A1 | 0.038261 |
| 3 | ILMN_1663171 | MATN3 | 0.016428 |
| 4 | ILMN_1732158 | FMO2 | 0.08681 |
| 5 | ILMN_1811790 | FOXS1 | 0.068965 |
| 6 | ILMN_2402392 | COL8A1 | 0.060799 |
| 7 | ILMN_1736078 | THBS4 | 0.088377 |

FIGS. 2 to 5 identified that the patient cohort is classified into the positive prognosis group or negative prognosis group according to the expression level of each 7 gene listed in Table 5, and the survival rate of positive prognosis group appears high compared to the survival rate of negative prognosis group. The results represents clinically that the prognosis of gastric cancer patients can be accurately predicted by measuring the expression level of gastric cancer prognostic gene in the present invention.

In addition, according to FIG. 16, the results of building the prognosis prediction model of seven genes listed in Table 5 and classifying the patients according to the model showed that the survival rates of group classified into the positive prognosis group (low risk) is significantly higher compared to the survival rate of the negative prognosis group (high risk), corresponding to the actual clinical results (FIG. 16). The results show that the 7 prognostic genes listed in Table 5 can be useful in predicting the gastric cancer prognosis.

Also, the stage Ib/II gastric cancer patients among the patients who had been classified according to the prognosis prediction model were re-classified into the positive prognosis group or negative prognosis group, and the Kaplan-Meier plot representing the disease-free survival rate of the classified group is shown in FIG. 17. As the result, the survival rate of the stage Ib/II gastric cancer patients who were classified into the positive prognosis group according to SuperPC prognosis prediction model is significantly higher compared to the survival rate of the stage Ib/II gastric cancer patients who were classified into the negative prognosis group (FIG. 17).

In particular, in SuperPC prognosis prediction model (using the expression levels of seven genes in Table 5), the prognosis index can be calculated through the following formula. If prognosis index, which is calculated through the following formula, of the certain is greater than −0.077491, the patient whom the sample was collected from can be classified into negative prognosis group.

$\Sigma Iwixi - 4.51425$

[wi and xi represent the i-th weight and the logarithmic expression level of gene, respectively]

7-2: Comparative Evaluation with Conventional Prognosis Factors

The present inventors used multivariate Cox analysis as standard statistical analysis to determine whether the prognosis prediction based on the prognostic genes in the present invention provides more meaningful prognostic information than the conventional prognosis factor. Specifically, the multivariate Cox model showing the disease-free survival rate evaluated by SuperPC prognosis index (Table 5) and 10-fold cross-validation, depth of invasion of the tumor cells (pT stage), the number of lymph nodes metastasized by tumor cells (P Node) was investigated.

The results of multivariate analysis identified that 7 prognostic genes, independently from pT stage and P Node, are excellent predictors of disease-free survival rate of gastric cancer patients who received curative gastrectomy and adjuvant chemotherapy (HR=1.9232, 95% CI, 1.4066, 2.6294, P<0.0001, Table 6).

TABLE 6

| Covariate | b | SE | P | Exp (b) | 95% CI of Exp (b) |
|-----------|---|----|----|---------|-------------------|
| HER2 = positive | −0.3020 | 0.2510 | 0.2289 | 0.7393 | 0.4531 to 1.2062 |
| P NODE | 0.5548 | 0.08754 | <0.0001 | 1.7415 | 1.4683 to 2.0657 |
| Tstage | 0.7339 | 0.1696 | <0.0001 | 2.0831 | 1.4965 to 2.8997 |
| Precicted_risk = "high" | 0.6540 | 0.1604 | <0.0001 | 1.9232 | 1.4066 to 2.6294 |

Example 8

Development and Evaluation of Prognosis Prediction Model Based on the Gastric Cancer Prognostic Genes—(2)

8-1: Prognosis Prediction Model Using Gradient Lasso Method

The genes that can be useful in predicting the gastric cancer prognosis among the 369 gastric cancer prognostic genes identified in Example 5 were screened using the gradient lasso algorithm (Sohn I et al.: Bioinformatics 2009; 25:1775-81). In the gradient lasso prognostic model, the prognosis score can be calculatedusing the following formula, and if the prognosis score of a random sample is positive, the positive prognosis can be predicted.

$\hat{\beta}x$ [$\hat{\beta}$ is the regression coefficient estimated from a training set, X is the vector of gene expression level of a training set.]

After selecting the genes using gradient lass, it is necessary to verify the affectivity using the independent data set. For this, leave one out cross validation (LOOCV) was used. Specifically, leave one out cross validation is to use N-1 samples (training data), except for one sample (test data) from the patient group, in generating the prognosis prediction algorithm by gradient lasso and to classify the remnant one sample into positive prognosis group or negative prognosis group by applying the same to the prognostic algorithm. Such a process was performed repetitively for N samples of the patient group. After completing the classification of all the samples into positive prognosis group or negative prognosis group, the survival rates between positive prognosis group and negative prognosis group were compared through statistical analysis.

26 prognostic genes were screened by gradient lasso algorithm during performing the leave one out cross validation and the screened genes are listed in Table 7. In addition, the Kaplan-Meier plot representing the survival rate according to the expression levels of 26 screened prognostic genes are shown in FIGS. 5 to 15. According to FIGS. 5 to 15, it is identified that the patient group is classified into positive prognosis group or negative prognosis group according to the expression level of each of 26 gene listed in Table 7, and the survival rate of positive prognosis group appears higher compared to the survival rate of negative prognosis group. The results represent clinically that the prognosis of gastric cancer patients can be accurately predicted by measuring the expression level of gastric cancer prognostic gene in the present invention.

TABLE 7

| PROBE_ID | SYMBOL | P-value | Frequency | Chromosomal Location | Regression coefficient($\beta$) |
|---|---|---|---|---|---|
| ILMN_2385647 | ALAS1 | 0.005756 | 432 | 3p21.1 | −0.024715 |
| ILMN_1713561 | C20orf103 | 0.000000 | 432 | 20p12 | 0.008195 |
| ILMN_1787749 | CASP8 | 0.000365 | 432 | 2q33-q34 | −0.003561 |
| ILMN_1712088 | CLYBL | 0.000780 | 432 | 13q32 | 0.147852 |
| ILMN_1672776 | COL10A1 | 0.000001 | 432 | 6q21-q22 | −0.048568 |
| ILMN_1673843 | CST2 | 0.000026 | 432 | 20p11.21 | −0.054399 |
| ILMN_1732158 | FMO2 | 0.000001 | 432 | 1q23-q25 | 0.025852 |
| ILMN_1811790 | FOXS1 | 0.000000 | 432 | 20q11.21 | −0.004554 |
| ILMN_1673548 | HSPC159 | 0.000209 | 432 | 2p14 | 0.027885 |
| ILMN_1662824 | MADCAM1 | 0.000956 | 432 | 19p13.3 | −0.017717 |
| ILMN_1719543 | MAF | 0.000267 | 432 | 16q22-q23 | 0.074349 |
| ILMN_2382679 | REG3A | 0.000232 | 432 | 2p12 | 0.059214 |
| ILMN_2071826 | RNF152 | 0.000264 | 432 | 18q21.33 | 0.008419 |
| ILMN_1736078 | THBS4 | 0.000001 | 432 | 5q13 | 0.017118 |
| ILMN_1757387 | UCHL1 | 0.000201 | 432 | 4p14 | −0.021701 |
| ILMN_2093500 | ZBED5 | 0.000081 | 432 | 11p15.3 | −0.026228 |
| ILMN_1801205 | GPNMB | 0.000313 | 431 | 7p15 | 0.010272 |
| ILMN_1755318 | HIST1H2AJ | 0.000036 | 431 | 6p22-p21.3 | −0.019642 |
| ILMN_1729033 | RPL9 | 0.000901 | 431 | 4p13 | 0.018665 |
| ILMN_1712506 | DPP6 | 0.007555 | 428 | 7q36.2 | −0.003465 |
| ILMN_1769168 | ARL10 | 0.000235 | 421 | 5q35.2 | −0.052923 |
| ILMN_1692739 | ISLR2 | 0.001375 | 421 | 15q24.1 | 0.032727 |
| ILMN_2316386 | GPBAR1 | 0.000049 | 408 | 2q35 | −0.020300 |
| ILMN_1792748 | CPS1 | 0.001224 | 397 | 2q35 | 0.059843 |
| ILMN_1665761 | BCL11B | 0.007679 | 378 | 14q32.2 | 0.037040 |
| ILMN_1793965 | PCDHGA8 | 0.002196 | 373 | 5q31 | 0.032342 |

Subsequently, the patient group was classified into the positive prognosis group or negative prognosis group according to the prognosis prediction model using 26 selected genes (gradient lasso and leave one out cross validation). Furthermore, the patient group which had been classified into the positive prognosis group or negative prognosis group was re-classified according to the pathological stage so that the prognosis could be predicted according to the pathological stage.

8-2: Evaluation of the Prognosis Prediction Model Using Gradient Lasso Method

In order to determine whether the prognosis predicted using 26 prognostic genes coincide with the actual clinical results, the disease-free survival rates of the group classified into positive prognosis group and negative prognosis group were represented in the Kaplan-Meier plot (FIG. 18). As the result, the disease-free survival rate for 5 years of the positive prognosis group (low risk) is significantly higher compared to the disease-free survival rate for 5 years of the negative prognosis group (high risk) (71.7% vs 47.7%) and the results appears to correspond to the hazard ratio of recurrence rate of 2.12 (95% CI, 1.57, 2.88, P=0.04, FIG. 18). Therefore, it was identified that the prognosis of gastric cancer patients who were classified using 26 prognostic genes coincides with the actual clinical results.

In order to determine whether the results of prognosis predicted by re-classifying the patients who had been classified into positive prognosis group and negative prognosis group according to pathological stage so that the prognosis can predicted according to the pathological stage coincide with the actual clinical results, the Kaplan-Meier plot representing the disease-free survival rates of the classified group of patients in each pathological stage according to prognosis was shown in FIG. 19. As the result, the cohort consisting of total 432 patients was classified into 145 in low risk, stage Ib/II (5-year disease-free survival rate of 84.8%); 90 in high-risk, stage Ib/II (5-year disease-free survival rate of 61.1%); 83 in low-risk, stage III/IV (5-year disease-free survival rate of 48.9%), and 114 in high-risk, stage III/IV (5-year disease-free survival rate of 36.9%). Specifically, it was identified that in Ib/II stage, survival rate of the positive prognosis group (low risk Ib/II) is significantly higher compared to the survival rate of negative prognosis group (high risk Ib/II) and even in III/IV stage, survival rate of the positive prognosis group (low risk III/IV) is significantly higher compared to the survival rate of negative prognosis group (high risk III/IV) (FIG. 19).

The results represent that the patients in pathological stage can be classified accurately according to the prognosis by processing the expression levels of prognostic genes with algorithm for statistical analysis, and the survival rate of gastric cancer patient can be improved by selecting the appropriate treatment according to the predicted prognosis. For example, the expression level of prognostic gene is measured from the patient who was diagnosed with Ib/II stage, self-normalized by measuring relative expression level to the reference gene, and then if classified into the negative prognosis group Ib/II stage according to gradient lasso algorithm, the prognosis of the patient can be determined similar as the prognosis of III stage, and the survival of the patient can be prolonged by by using the treatment method for patients in stage III.

8-3: Comparative Evaluation with Conventional Prognosis Factors

As the known prognosis factors to predict gastric cancer prognosis, there are determination of depth of invasion of the tumor cells (pT stage) and the number of lymph nodes metastasized by tumor cells (P Node). The present inventors used multivariate Cox analysis as standard statistical analysis to determine whether the prognosis prediction based on the prognostic genes in the present invention provides a more meaningful prognostic information than the conventional prognosis factor. Specifically, the multivariate Cox model showing the disease-free survival rate evaluated by gradient lasso index (26 prognostic genes listed in Table 7) and leave one out cross-validation, depth of invasion of the tumor cells (pT stage), the number of lymph nodes metastasized by tumor cells (P Node) or pathological stage (ADCC 6-th edition) was investigated. In this case, pT stage was divided by pT1/T2 and T3, and logarithm of P Node was taken with replacing 0 by 0.1.

The results of multivariate analysis identified that 26 prognostic genes, independently from pT stage and P Node, are excellent predictors of disease-free survival rate of gastric cancer patients who received curative gastrectomy and adjuvant chemotherapy (HR=1.859, 95% CI, 1.367, 2.530, P=0.000078, Table 8). Likewise, as shown in Table 9, it was identified that the disease-free survival rate can be predicted independently in the last pathological stage by 26 prognostic genes (HR=1.773, 95% CI, 1.303, 2.413, P<0.00001, Pstage in Table 9 is the combination of pTstage and P Node).

TABLE 8

|  | Hazard ratio | 95% CI for hazard ratio | P-value |
| --- | --- | --- | --- |
| Tstage | 2.225 | (1.605, 3.085) | 0.000002 |
| Log(P NODE) | 2.129 | (1.612, 2.812) | 0.000000 |
| Risk level | 1.859 | (1.367, 2.530) | 0.000078 |

TABLE 9

|  | Hazard ratio | 95% CI for Hazard ratio | P-value |
| --- | --- | --- | --- |
| Pstage | 2.779 | (2.024, 3.816) | <0.000001 |
| Risk level | 1.773 | (1.303, 2.413) | 0.000265 |

Example 9

Development and Evaluation of Prognosis Prediction Model Based on the Gastric Cancer Prognostic Genes—(3)

9-1: Development and Evaluation of Gastric Cancer Prognostic Score for II Stage Gastric Cancer Patient Using nCounter Assay By applying gradient lasso algorithm to the tumor samples of stage II gastric cancer patients (N=186) obtained from a cohort used in WG-DASA assay, the combination of 8 gastric cancer prognostic genes to provide robust prognostic information was identified (Table 10). The gastric cancer prognostic score (GCPS) was developed by the normalized expression levels of the 8 genes and the linear combination of Cox regression estimate. The measurement of the expression level of gene was performed using an nCounter assay kit (system; NanoString Technologies).

TABLE 10

| Gene Symbol | Regression estimate |
| --- | --- |
| C20orf103 | 0.0636 |
| CDC25B | -0.0175 |
| CDK1 | -0.1005 |
| CLIP4 | 0.4822 |
| LTB4R2 | -0.3950 |
| MATN3 | 0.2982 |
| NOX4 | 0.0288 |
| TFDP1 | -0.2886 |

The GCPS to distribute the 25% of patients into negative prognosis group was identified as most robust by the analysis of the cut-off (FIG. 28). The cut-off was selected for the future verification in the independent validation cohort. As the result of applying the optimized cut-off to the cohort, as shown in FIG. 29, 5-year disease-free survival of high-risk group (bottom graph of 42.6% was identified by the expression level of gene based on the prediction model, compared to the 5-year disease-free survival rate low-risk group (top graph) of 84.3% (p<0.0001).

Due to the problem of overfitting, it is necessary to validate GCPS with fixed algorithms and cut-off with the independent patient cohort which is not used to identify the gene as the subject. To this end, cohort of patients for verification was first obtained. The GPS was applied to the independent validation cohort of 2 stage gastric cancer patients who received the same chemo-radiotherapy as which the patients (N=186, discovery cohort) used for identification of the gastric cancer prognostic gene of patients. As a result, the risk score distribution is very similar to FIG. 30, which represents the robust analytical performance of this assay.

The result of applying the predefined cut-off Of (0.2205 of GCPS obtained from the discovery cohort to the validation cohort and generating Kaplan-Meier plot based on the class distribution identified that the algorithm can accurately identify the patient with a higher risk of gastric cancer among the 2 stage gastric cancer patients who received chemo-radiotherapy (FIG. 31). As shown in FIG. 31, GPS of the 8 prognostic genes successfully predicted 216 patients with 2 stage gastric cancer in high-risk group (5-year DFS, 58.7%, the bottom graph) and low-risk group (5-year DFS, 86.3%, the top graph) (P=0.00004, HR=3.15).

9-2: Optimization of GCPS

According to the examples, after verifying that the high-risk patients can be identified among the stage 2 patients who received chemo-radiotherapy by the expression profiling of the gastric cancer prognostic genes, the discovery cohort and the validation cohort were combined as one cohort to develop the 2-nd generation GCPS. In order to develop the prediction model based on Cox proportional hazard model for the disease-free survival rate, gradient lasso (Least Absolute Shrinkage and Selection Operator) algorithm was used. Table 11 represents 13 genes (probes) composing the prediction model obtained using phase 2 data set (N=402) which is the combination of the discovery set and the validation set.

TABLE 11

| Gene Symbol | Regression estimate |
| --- | --- |
| ADRA2C | -0.0156 |
| C20orf103 | 0.1082 |
| CLIP4 | 0.3891 |
| CSK | -0.6654 |
| FZD9 | -0.0829 |
| GALR1 | -0.0509 |
| GRM6 | -0.0244 |
| INSR | 0.0251 |
| LPHN1 | -0.0126 |
| LYN | -0.0012 |
| MATN3 | 0.2134 |
| MRGPRX3 | -0.0009 |
| NOX4 | 0.0951 |

GCPS of the patient was calculated as $[S=\beta_1 x_1 + \ldots + \beta_n x_n]$. Wherein, $x_n$ is the quantified expression value of the n-th gene, $\beta_n$ is the regression estimate of the n-th gene listed in Tables 10 and 11, and S represents the gastric cancer prognostic score. Subsequently, the cut-offs for the first quartile and the third quartile of the distribution of the risk score were estimated from the phase 2 data set (Q1=-0.9842, Q3=-0.4478). By applying the cut-offs to 306 patients of the final validation set, the patients with GCPS lower than Q1, and the patients with GCPS greater than Q3 were distributed into the low-risk group and high-risk group, respectively. As the result, as shown in FIG. 24, the Kaplan-Meier plot identified that the survival rate of the patients who were predicted as high-risk group (the bottom graph) is significantly lower compared to the patients of other groups (FIG. 32).

9-3: Validation of the 2nd Generation GCPS in Stage II Gastric Cancer Patients Who Received Only the Surgery.

In order to test the performance of the GCPS for the patients who received only the surgery without chemo or radiation therapy, the cancer tissues of 306 patients diagnosed with 2 stage who received only the radical curative gastrectomy without adjuvant chemotherapy or post-operative radiation therapy in Samsung Medical Center were examined. The patients were selected according to the following criteria.

Among 476 gastric cancer patients diagnosed with the pathological stage 2 who received only the radical curative gastrectomy without adjuvant chemotherapy or post-operative radiation therapy in Samsung Medical Center from April of 1995 to September of 2006, 306 patients were selected according to the following criteria.

1) histological diagnosis of adenoma,
2) tumor resection without residual tumor,
3) D2 lymph node dissection,
4) over 18 years old,
5) the pathological stage II (T1N2, T2aN1, T2bN1 and T3N0) according to AJCC (American Joint Committee on Cancer) 6th edition,
6) complete preservation of surgical records and treatment records.

170 patients among the cohort of 476 patients were excluded from the analysis due to the reasons as follows:
1) patients without complete medical records (N=66),
2) death without disease or unexplained death (N=43),
3) corrected pathological stage (N=45)
4) no available paraffin block (N=15),
5) dual primary cancers (N=1).

As shown in FIG. 33, as the result of applying the second-generation GCPS to the cohort of the 2 stage gastric cancer patients who received surgery alone, the patients who were classified into high-risk group (the bottom graph) according to GCPS were identified to have poor prognosis compared to row-risk group although GCPS was developed using the patient cohort who received chemo-radiotherapy (p=0.00287). The results represent that the high-risk patients defined by GCPS essentially poor prognosis which is not improved by anticancer drugs and radiation therapy and new treatments for these patients need to be developed.

Effect of the Invention

According to the present invention, gastric cancer prognosis may be predicted promptly and accurately, and an appropriate treatment plan can be determined based on the predicted prognosis, which has an advantage of contributing to significant reduction of death caused by gastric cancer. Particularly, according to the present invention, the survival rate can be remarkably increased by using the targeted therapies developed for stage III gastric cancer, since a patient who has been predicted to have a negative prognosis among stage Ib/II gastric cancer patients shows the similar prognosis as stage III gastric cancer patient and is resistant to the existing standard chemotherapy.

What is claimed is:

1. A method for predicting gastric cancer prognosis, comprising:
   a) measuring an expression level of mRNA or protein of a marker for predicting gastric cancer prognosis in a sample collected from a gastric cancer patient to obtain a quantified expression value;
   b) applying the expression value obtained in step a) to a prognosis prediction model to obtain a gastric cancer prognostic score, wherein the prognosis prediction model is expressed as:

$$[S=\beta_1 x_1 + \ldots + \beta_n x_n]$$

wherein, $x_n$ is the quantified expression value of the n-th gene,
   $\beta_n$ is the Cox Regression estimate of n-th gene, and
   S represents the gastric cancer prognostic score; and
   c) comparing the gastric cancer prognostic score obtained in step b) with a reference value to determine prognosis of the patient,
   wherein the marker for predicting gastric cancer prognosis is a combination of C20orf103 (chromosome 20 open reading frame 103), MATN3 (matrilin 3), CLIP4 (CAP-GLY domain containing linker protein family, member 4), NOX4 (NADPH oxidase 4), ADRA2C (adrenergic, alpha-2C-, receptor), CSK (c-src tyrosine kinase), FZD9 (frizzled family receptor 9), GALR1 (galanin receptor 1), GRM6 (glutamate receptor, metabotropic 6), INSR (insulin receptor), LPHN1 (latrophilin 1), LYN (v-yes-1 Yamaguchi sarcoma viral related oncogene homolog) and MRG-PRX3 (MAS-related GPR, member X3) genes.

2. The method according to claim 1, wherein the case of the gastric cancer prognostic score obtained in the step b) same as or larger than the reference value is determined to have negative prognosis.

3. The method according to claim 1, wherein the reference value is −0.4478, and the case of the gastric cancer prognostic score obtained in the step b) same as or larger than the reference value is determined to have negative prognosis.

4. The method according to claim 1, wherein the gastric cancer is Ib or II stage gastric cancer.

* * * * *